US010278911B2

(12) United States Patent
Anzali et al.

(10) Patent No.: US 10,278,911 B2
(45) Date of Patent: May 7, 2019

(54) COMPOSITIONS CONTAINING CYCLIC PEPTIDES AND METHODS OF USE

(71) Applicant: Merck Patent GmbH, Darmstadt (DE)

(72) Inventors: Soheila Anzali, Gross-Zimmern (DE); Alfred Jonczyk, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 25 days.

(21) Appl. No.: 14/708,740

(22) Filed: May 11, 2015

(65) Prior Publication Data

US 2015/0265516 A1 Sep. 24, 2015

Related U.S. Application Data

(62) Division of application No. 12/936,761, filed as application No. PCT/EP2009/002619 on Apr. 8, 2009, now abandoned.

(30) Foreign Application Priority Data

Apr. 8, 2008 (EP) ..................................... 08006968

(51) Int. Cl.

| A61K 8/64 | (2006.01) |
|---|---|
| A61K 9/00 | (2006.01) |
| A61K 38/12 | (2006.01) |
| A61Q 19/00 | (2006.01) |
| A61Q 19/08 | (2006.01) |
| C07K 7/64 | (2006.01) |
| A61Q 5/00 | (2006.01) |
| A23L 33/18 | (2016.01) |
| A61K 9/02 | (2006.01) |
| A61K 9/06 | (2006.01) |
| A61K 9/08 | (2006.01) |
| A61K 9/107 | (2006.01) |
| A61K 9/127 | (2006.01) |
| A61K 9/19 | (2006.01) |
| A61K 9/20 | (2006.01) |
| A61K 9/28 | (2006.01) |
| A61K 9/48 | (2006.01) |
| A61Q 5/02 | (2006.01) |
| A61Q 5/06 | (2006.01) |
| A61Q 5/12 | (2006.01) |
| A61Q 7/00 | (2006.01) |
| A61Q 19/06 | (2006.01) |

(52) U.S. Cl.
CPC ............. *A61K 8/64* (2013.01); *A23L 33/18* (2016.08); *A61K 9/0014* (2013.01); *A61K 38/12* (2013.01); *A61Q 5/00* (2013.01); *A61Q 19/00* (2013.01); *A61Q 19/08* (2013.01); *C07K 7/64* (2013.01); *A61K 9/006* (2013.01); *A61K 9/0019* (2013.01); *A61K 9/0031* (2013.01); *A61K 9/0043* (2013.01); *A61K 9/0048* (2013.01); *A61K 9/02* (2013.01); *A61K 9/06* (2013.01); *A61K 9/08* (2013.01); *A61K 9/1075* (2013.01); *A61K 9/127* (2013.01); *A61K 9/19* (2013.01); *A61K 9/2018* (2013.01); *A61K 9/2054* (2013.01); *A61K 9/286* (2013.01); *A61K 9/2826* (2013.01); *A61K 9/4866* (2013.01); *A61Q 5/006* (2013.01); *A61Q 5/02* (2013.01); *A61Q 5/06* (2013.01); *A61Q 5/12* (2013.01); *A61Q 7/00* (2013.01); *A61Q 19/06* (2013.01)

(58) Field of Classification Search
None
See application file for complete search history.

(56) References Cited

U.S. PATENT DOCUMENTS

| 5,866,540 | A | 2/1999 | Jonczyk |
|---|---|---|---|
| 6,001,961 | A | 12/1999 | Jonczyk |
| 6,127,335 | A | 10/2000 | Jonczyk et al. |
| 6,143,723 | A | 11/2000 | Ramaiah |
| 6,169,072 | B1 | 1/2001 | jonczyk |
| 6,521,595 | B1 | 2/2003 | Kim et al. |
| 6,809,075 | B1 | 10/2004 | Mitts et al. |
| 6,995,238 | B2 | 2/2006 | Meyer et al. |
| 7,160,560 | B2 | 1/2007 | Pinnell |

FOREIGN PATENT DOCUMENTS

| CA | 2021951 A1 | 1/1991 |
|---|---|---|
| DE | 4310643 A1 | 10/1994 |
| DE | 19534016 A1 | 3/1997 |
| DE | 19534177 A1 | 3/1997 |
| EP | 0410540 A1 | 1/1991 |
| EP | 1864995 A1 | 12/2007 |
| WO | 9509611 A2 | 4/1995 |
| WO | 2004002440 A1 | 1/2004 |
| WO | 2004011487 A2 | 2/2004 |
| WO | WO 2008/143928 * | 11/2008 |
| WO | 2009002751 A2 | 12/2008 |
| WO | 2009040071 A2 | 4/2009 |
| ZA | 9607765 A | 3/1997 |

OTHER PUBLICATIONS

OneSkin.com, downloaded on Oct. 30, 2015 from URL:< http://dermatology.netfirms.com/SkinFAQs/FAQsOnAgeing.html >.*
Textured Talk, downloaded on Oct. 30, 2015 from URL:< http://www.texturedtalk.com/the-truth-about-preventing-reversing-gray-hair/>.*
Medical News Today (downloaded on Mar. 15, 2018 from URL: <https://www.medicalnewstoday.com/articles/312845.php>) (Year: 2018).*
Dermasweep (downloaded on Mar. 15, 2018 from URL: http://dermasweep.com/skin-health-treatments/laxity/) (Year: 2018).*
Fabi (Clinical, Cosmetic and Investigational Dermatology 2015:8 47-52) (Year: 2015).*

(Continued)

*Primary Examiner* — Sergio Coffa
(74) *Attorney, Agent, or Firm* — Millen White Zelano and Branigan, PC; Csaba Henter

(57) ABSTRACT

The invention relates generally to cyclic peptides and their use in compositions, especially topical, cosmetic and/or personal care compositions, and compositions containing said cyclic peptides.

23 Claims, 2 Drawing Sheets

(56) References Cited

OTHER PUBLICATIONS

Health Community (downloaded from URL:< http://obesity.ygoy.com/how-to-diminish-stretch-marks-due-to-obesity/>, Jan. 17, 2008) (Year: 2008).*
Nichols (downloaded on Mar. 19, 2018 fro URL: https://www.medicalnewstoday.com/articles/283651.php) (Year: 2018).*
World IP Organization. "International Search Report." PCT/EP2009/002619. Applicant: Merck Patent GmbH. dated Jul. 24, 2009.
Egbaria et al., Liposomes as a topical drug delivery system, Advanced Drug Delivery Reviews, 5 (1990) 287-300.

* cited by examiner

COMPOSITIONS CONTAINING CYCLIC PEPTIDES AND METHODS OF USE

The invention relates generally to cyclic peptides and their use in compositions, especially topical, cosmetic and/or personal care compositions, and compositions containing said cyclic peptides.

A variety of natural and synthetic peptides have found widespread use in cosmetic compositions. Typically, peptides are included in cosmetics for their functional attributes such as enzyme inhibition, antiviral and antibacterial activity.

General examples of the use of peptides in cosmetic applications are known in the literature, e.g. WO 2007/100874, and the literature cited therein.

All publications including patents and patent applications cited herein are hereby incorporated by reference in their entirety.

Despite the desirability of incorporating peptides in cosmetics, there are certain disadvantages associated with their use. For example, active peptide agents may suffer from poor efficacy of use due to, for instance, their conformational flexibility and/or the easy digestion of peptides by proteases at the sites of intended action. Further, efficacy may be hindered due to the difficultly with which peptides are transported across membranes such as skin and their poor solubility in many cosmetic vehicles. Additionally, the risk of immunogenic reaction to peptides also presents a concern in cosmetic formulation.

It is therefore an object of the invention to provide advantageous peptides for cosmetic applications which provide enhanced efficacy, to provide advantageous peptides for cosmetic applications which inter alia provide higher resistance to proteolytic degradation and/or to provide advantageous peptides for cosmetic applications which decrease the risk of immunogenic reaction. Moreover, it is an object of the instant invention to provide novel and preferably improved compositions that preferably have a better acting profile, a better side-effect profile and/or improved handling.

It is therefore a preferred object of the invention to provide novel compositions, preferably cosmetic and/or personal care compositions, comprising said advantageous peptides. The novel compositions show advantageous properties, preferably selected from the group consisting of enhanced efficacy, higher stability and/or less immunogenic reactions.

The cyclic peptides as described herein and the compositions containing them are preferably beneficial or advantageous with respect to cosmetic and personal care applications and medicinal products, preferably cosmetic and personal care applications, especially when applied topically. Topically in this respect preferably means that the cyclic peptides and the compositions containing them are generally applied on the surface of the human or animal body. The surface of the body in this regard preferably includes the skin, the hair, preferably including the hair roots, and/or at the mucous membranes, preferably the eyes and ears, more preferably the skin and/or the hair. Accordingly, the application of the compositions for topical use on the skin and/or hair of the human or animal body, preferably human body is generally preferred. Preferably. a topical application to a certain area of the skin is affecting only or mainly the area to which it is applied. Thus, topically preferably means the opposite of systemically.

The present invention thus relates to compositions comprising one or more cyclic peptides, preferably one or more cyclic peptides as described below, to the preparation and use thereof for the care, preservation or improvement of the general state of the skin or hair and for prophylaxis against time- and/or light-induced ageing processes of the human skin or human hair and for the prophylaxis and/or treatment of skin diseases. The invention furthermore relates to compositions having an effective content of said one or more cyclic peptides. Preferably, the invention also relates to the use of one or more cyclic peptides for the prophylaxis and/or treatment of disorders of the skin, inflammations, allergies, irritations and/or improvements of the wound healing of the skin. Preferably, the cyclic peptides for use according to the invention have integrin modulating properties, more preferably either integrin antagonistic activity (i.e. preferably integrin inhibitory activity) or integrin agonistic activity (i.e. preferably integrin stimulatory activity) and especially integrin antagonistic activity (i.e. preferably integrin inhibitory activity) as well as integrin agonistic activity (i.e. preferably integrin stimulatory activity). The respective kind of integrin modulating activity can preferably be controlled by the respective cyclic peptide employed and/or the applied amount/concentration thereof. It can be shown that cyclic peptides, preferably cyclic peptides according to the invention, exhibit integrin antagonistic activity in one concentration range, preferably in a high concentration range, and exhibit integrin antagonistic activity in another concentration range, preferably in a low concentration range, e.g. according to the method described in Legler et al. J Cell Sci. 2001 April; 114(Pt 8):1545-53) or analogous methods thereof. More preferably, the cyclic peptide use according to the invention ligands of integrins, selected from the group consisting of αvbeta3, αvβ5, αvβ1, αvβ6, αvβ8 and αvβ3 integrins, and especially selected from the group consisting of αvβ3 and αvβ5 integrins. These activities can be demonstrated, for example, according to the method described by J. W. Smith et al in J. Biol. Chem. 265, 12 to 67-1 to 271 (1990), or in an analogous manner thereof.

Integrins are heterodimer transmembrane receptors for the extracellular matrix composed of an alpha and beta subunit. Natural integrin ligands include laminin, fibronectin, and vitronectin, but they also include fibrinogen and fibrin, thrombospondin, MMP-2, and fibroblast growth factor 2. Integrins bind ligands by recognizing short amino acid stretches on exposed loops, particularly the arginine-glycine-aspartic acid (RGD) sequence. On ligation, integrins mediate complex signaling events, alone or in combination with growth factor receptors, regulating cell adhesion, proliferation, survival, and migration by activating canonical pathways, such as integrin-linked kinase (ILK), protein kinase B (PKB/Akt), mitogen-activated protein kinase (MAPK), Rac or nuclear factor kappa B (NF-κB). In resting vessels, integrins interact with the basal membrane, thereby maintaining vascular quiescence. [Stupp and Ruegg, Journal of Clinical Oncology, Vol 25, No 13 (May 1), 2007: pp 1637-1638].

αv integrins bind ligands in the extracellular matrix (ECM). These ligands include collagen, fibronectin, vitronectin, laminin, thrombospondin, and osteopontin. Collagens are a family of fibrous proteins and as a major component of skin and bone they are the most abundant proteins in mammals. Collagens serves as counter-receptors for some β1 and β3 integrins. Fibrinogen, which is a dimeric soluble plasma protein important in blood clotting, wound healing and inflammation, is a ligand for integrins including Mac-1, αXβ2, αIIbβ3, and αvβ3 (Berman et al., 2003; Springer and Wang, 2004).

The dependency of the development of angiogenesis on the interaction between vascular integrins and extra-cellular matrix proteins is described by P. C. Brooks, R. A. Clark and D. A. Cheresh in Science 264, 569-71 (1994).

The possibility of inhibiting this interaction and the associated initiation of apoptosis (programmed cell death) of angiogenic vascular cells by a cyclic peptide is described by P. C. Brooks, A. M. Montgomery, M. Rosenfeld, R. A. Reisfeld, T.-Hu, G. Klier and D. A. Cheresh in Cell 79, 1157-64 (1994).

RGD-binding integrins are requisite latent TGF-β1 activators during development and in the immune system (Yang, Zhiwei; Mu, Zhenyu; Dabovic, Branka; Jurukovski, Vladimir; Yu, Dawen; Sung, Joanne; Xiong, Xiaozhong; Munger, John S., Journal of Cell Biology (2007), 176(6), 787-793 Transforming growth factor (TGF)-β induces fibroblast contraction, which is implicated in wound healing and keloid formation. It has been suggested that an inhibitor of TGF-β type I receptor kinase activity may have therapeutic potential for excessive skin contraction as obsd. in keloid (Hasegawa, Toshio; Nakao, Atsuhito; Sumiyoshi, Koji; Tsuchihashi, Hitoshi; Ogawa, Hideoki, Journal of Dermatological Science (2005), 39(1), 33-38.). Therefore, RGD-binding intergrins inhibitors yield to less active TGF-61.

Okigami reported the use of tamoxifen and quercetin is disclosed for topical treatment of wrinkles in the skin. At concns. of 0.1-5% they prevent wrinkles by inhibiting fibronectin, TGF-β, and IGF-I (Okigami, Henry; Okigami, Paulo Takao. Braz. Pedido P I (2006), 9pp.)

Accumulating evidence indicates that endothelial cell integrins that bind to the matrix proteins assocd. with inflammation and wound healing are involved in the process of angiogenesis. The integrins contg. the αv subunit appear to be particularly important. To study the involvement of these receptors in human angiogenesis, a model of wound-associated human angiogenesis was established in human skin transplanted onto severe combined immunodeficient (SCID) mice. Using this model, they studied the expression of several αv integrins and tested the hypothesis that blockage of the αvβ3 integrin would inhibit human angiogenesis during human wound healing. These studies revealed that the αvβ3, αvβ5, and αvβ6 integrins are up-regulated briefly during wound angiogenesis with different patterns of expression and that inhibition of the αvβ3 integrin blocked new vessel formation during human wound healing (Christofidou-Solomidou, Melpo; Bridges, Mark; Murphy, George F.; Albelda, Steven M.; Delisser, Horace M. Pulmonary and Critical Care Division, Department of Medicine and Department of Dermatology, University of Pennsylvania Medical Center, Philadelphia, Pa., USA. American Journal of Pathology (1997), 151(4), 975-983.)

Skin damage, e.g. acute UVB-induced skin damage, can be reduced in a subject by administering to a subject having, or at risk for, acute UVB-induced skin damage, an agent that inhibits VEGF signalling (WO 2005/097187).

VEGF is an important growth factor for the microvascular and macrovascular endothelial cells that comprise the arteries, veins and lymphatics throughout the body (Leung D W et al., Science 1989; 246:1306-9). VEGF is produced by a wide variety of cell types. In the skin, keratinocytes appear to be an important source of VEGF (Ballaun C et al., J Invest Dermatol 1995; 104:7-10).

The human skin is subject to certain ageing processes, some of which are attributable to intrinsic processes (chronoageing) and some of which are attributable to exogenous factors (environmental, for example photoageing). In addition, temporary or even lasting changes to the skin picture can occur, such as acne, greasy or dry skin, keratoses, rosaceae, light-sensitive, inflammatory, erythematous, allergic or autoimmune-reactive reactions, such as dermatosis and photormatosis.

The exogenous factors include, in particular, sunlight or artificial radiation sources having a comparable spectrum, and compounds which can be formed by the radiation, such as undefined reactive photoproducts, which may also be free-radical or ionic. These factors also include cigarette smoke and the reactive compounds present therein, such as ozone, free radicals, for example the hydroxyl free radical, singlet oxygen and other reactive oxygen or nitrogen compounds which interfere with the natural physiology or morphology of the skin.

The influence of these factors can result, inter alia, in direct damage to the DNA of the skin cells and to the collagen, elastin or glycosaminoglycan molecules of the extracellular matrix, which are responsible for the strength of skin. In addition, the signal transduction chains, which are terminated by the activation of matrix-degrading enzymes, may be affected. Important representatives of these enzymes are the matrix metalloproteinases (MMPs, for example collagenases, gelatinases and stromelysins), whose activity is additionally regulated by TIMPs (tissue inhibitors of matrix metalloproteinases).

The consequences of the above-mentioned ageing processes are thinning of the skin, weaker interlacing of epidermis and dermis, and a reduction in the number of cells and the supplying blood vessels. These results in the formation of fine lines and wrinkles, the skin becomes leathery, and pigment defects can occur.

The same factors also act on hair, where damage can likewise occur. The hairs become brittle, less elastic and dull. The surface structure of the hairs is damaged.

Cosmetic or dermatological care products having properties which are claimed to counter the processes described or comparable processes or reduce or reverse the harmful consequences thereof are frequently distinguished by the following specific properties—free-radical-scavenging, anti-oxidative, inflammation-inhibiting or humectant. They prevent or reduce, inter alia, the activity of matrix-degrading enzymes or regulate the new synthesis of collagen, elastin or proteoglycans.

The above-mentioned ageing processes result in a thinning of the skin, the decrease of serration between epidermis and dermis, reduction of the cell number as well as the reduction of the supplying blood vessels. These processes are accompanied by the formation of lines and wrinkles, the skin becomes leather-like and/or shows pigmentary abnormalities.

Those factors also effect the status of the hair, resulting as well in a damage of the hair, especially damages in the surface of the hair that lead to brittleness and the loss of elasticity and gloss of the hair.

Care products and/or cosmetic products with properties that shall counteract against the described or similar processes and/or that shall reverse the damaging results often sure one or more of the following properties: free radical scavenging, anti-oxidative, anti-inflammatory and/or moisturising. Preferably, they block or reduce the activity of the matrix-disintegrating enzymes or control the denovo-synthesis of collagen, elastin and/or proteoglycans.

The use of antioxidants or free-radical scavengers in cosmetic compositions is adequately known per se. Thus, the use of the antioxidative vitamin E in sunscreen formulations is usual. Nevertheless, the effect achieved is even here well short of the hoped-for effect.

Vitamin A and vitamin-A derivatives, such as retinoic acid, retinol and retinol esters, act on the differentiation of epithelial cells and are therefore employed for the prophylaxis and treatment of numerous phenomena which impair the skin state, for example use against acne, psoriasis, senile keratosis, skin discoloration and wrinkles has been described (cf., for example, WO 93/19743 and WO 02/02074).

However, a skin-irritant effect of retinol and derivatives is also described in the literature (for example WO 94/07462). These side effects restrict the use of retinol to narrowly limited areas, it being necessary to avoid overdosing. There is therefore a demand for active ingredients which have a retinol-like spectrum of action, but do not have the side effects described or at least only do so in reduced form.

Owing to the constantly increasing demand for active ingredients for the preventative treatment of human skin and human hair against ageing processes and harmful environmental influences, the object of the present invention was to provide novel active ingredients which exhibit the effects already mentioned at the outset, are sufficiently oxidation- and photostable and can readily be formulated. The compositions prepared therewith should furthermore have as far as possible a low irritation potential for the skin, as far as possible have a positive influence on water binding in the skin, retain or increase skin elasticity and thus promote smoothing of the skin. In addition, they should preferably create a pleasant skin feeling on application to the skin. Preferably, new active ingredients preferably show one or more properties, selected from the group consisting of anti-ageing, anti-inflammatory, wrinkle preventing and wound healing properties. Preferably, they can be employed in products for capillary fragility treatment and/or prophylaxis, products for the treatment and/or prophylaxis of can, products for the treatment and/or prophylaxis of psoriasis, products for the treatment and/or prophylaxis of cellulite and/or Products for treatment and/or prophylaxis of grey hair.

The cyclic peptides for use according to the instant invention are novel active ingredients for the above discussed uses. Preferably, the cyclic peptides for use according to the invention have advantageous properties, such as improved handling properties, improved stability properties and/or an advantageous integrin modulating activity.

Linear peptides from extracts of natural sources or from synthesis are known as additives/ingredients/incipients in cosmetics, e.g. from Brewster Cosmetics & Toiletries magazine 121(11) 20-24 (2006), WO07/113356, WO07/100874, WO07/093839, WO07/068998, WO05/025505, Huang US 2005226839, US 2005050656 and DE102006046076.

However, backbone and terminal, heterodetic and homodetic, cyclization of linear peptides can improve the stability against degradation, peptidases, and metabolism (Bogdanowich-Knipp et al. J Pept Res. 1999 May; 53(5):530-41, Li et al. Current Topics in Medicinal Chemistry 2002, 2, 325-341, Hess J. Med. Chem. 2007, 50, 6201-6211, Matsoukas et al. J Med Chem. 2005 Mar. 10; 48(5)1470-80). In certain cases physicochemical stability even permitted sublimation of a cyclic pentapeptide (Bodanszky Int J Pept Protein Res. 1983 November; 22(5):590-6).

In addition, cyclization of RGD peptides can be worked out to enhance binding affinity to a certain target, such as an integrin, and to achieve selectivity for a group of targets, preferably a group of integrins (Samanen et al. J Med Chem. 1991 October; 34(10):3114-25, Dechantsreiter et al. J Med Chem. 1999 Aug. 12; 42(16):3033-40, Heckmann et al. Methods Enzymol. 2007; 426:463-503).

Integrins are a superfamily of more than 20 heterodimeric cell membrane spanning cell adhesion receptors that bind to ECM ligands, cell-surface ligands, and soluble ligands (Takada et al. Genome Biol. 2007; 8(5):215, ffrench-Constant et al. Trends Cell Biol. 14(12) 678-686 (2004), Akiyama Hum Cell. 1996 September; 9(3):181-6).

The RGD-ligand dependent integrin αvβ3 is known to be involved in several pathologies like tumor development, angiogenesis, restenosis, osteoporosis, and inflammatory diseases like arthritis (Le Tourneau Oncology (Williston Park). 2007 August; 21(9 Suppl 3):21-4, Ellis Am Surg. 2003 January; 69(1):3-10, Moussa et al. Curr Opin Investig Drugs. 2002 August; 3(8):1191-5, Hartmann et al. Exp. Opin. Invest. Drugs 9(6) 1281-1291 (2000), Tweti et al. Calcif Tissue Int. 2002 October; 71(4):293-9, Wilder Ann Rheum Dis. 2002 November; 61 Suppl 2: ii96-9).

Inhibitors of integrin αvβ3 known from clinical studies are the antibody vitaxin/MEDI-522 and the cyclic pentapeptide Cilengitide (Cai et al. Hum Cell. 1996 September; 9(3):181-6, Tucker Curr. Opin. Invest. Drugs 4(6) 722-731 (2003), Nemeth, et al. Cancer Investigation (2007), 25(7), 632-646).

Structure and function of integrin αvβ3 are known in some detail (Arnaout Annual Review of Cell and Developmental Biology 21: 381-410, 2005, J Cell Biol. 2005 Mar. 28; 168(7):1109-18, Xiong et al. Science. 2002 Apr. 5; 296(5565):151-5)

There are several soluble and matrix bound natural ligands binding to αv-integrins. Fibrinogen, vitronectin, fibronectin, osteopontin, and denatured collagen are examples (Ruoslahti et al. Cell 44, 517-518 (1986), Hynes Cell 69, 11-25 (1992), Lin et al. J Biol Chem. 1997 Sep. 19; 272(38):23912-20,). Many synthetic ones have been prepared (Cacciary et al. Curr. Med. Chem. 12, 51-70 (2005), Duggan Exp. Opin. Ther. Patents 10(9) 1367-1383 (2000))

One of the naturally occurring RGD ligands for αv-integrins is LAP, the ligating part of latent transforming growth factor LAP-TGFβ. Its role in activation and release of active TGFβ has been described (Sheppard Cancer and Metastasis Reviews 24: 395-402, 2005). In short, it is believed that TGFβ has to be activated to have its pleiotrophic activity. The activation results from splintering of the LAP peptide, which is locally triggered by integrins, including αvβ3 and/or αvβ6. Moreover, αvβ3 interacts with other receptors, such as receptors of growth factors (e.g. VEGF receptor, PDGF receptor and/or IGF1 receptor). Since TGFβ is associated with fibrosis, it is believed that fibrotic disorders and/or the signs of fibrotic disorders of the skin can be ameliorated by αvβ3 and/or αvβ6 active integrin modulators, preferably integrin inhibitors.

In addition to their inhibitory activity at sufficiently high concentration, RGD ligands at low concentration have been shown to be able to activate integrins (Legler et al. J Cell Sci. 2001 April; 114(Pt 8):1545-53). Therefore, activation of αv-integrin dependent cellular processes by cyclic RGD ligands, preferably selected from the cyclic peptides according to the invention, more preferably cyclic peptides according to the invention which comprise the Arg-Gly-Asp sequence (also referred to as "cyclic RGD peptides" or "cRGD peptides") at low concentration is feasible. For example, cRGD peptides formulated in a topical application may be adjusted in concentration and dose to modulate angiogenesis, or activation of TGFβ from its precursor, thereby ameliorating scars, wounds, inflammatory processes, aging, and/or wrinkle formation.

TGFβ is pleiotropic cytokine and growth factors involved manifold in physiological and pathological processes, which signal via their receptors, the TGFβ receptor tyrosine kinases and their substrate, the Smads. (Pennington Curr Opin Oncol. 2007 November; 19(6):579-85). It plays a critical role in suppression of the immune system in the periphery to prevent an autoimmune response. The family of TGFβs are regulatory molecules with numerous effects on cell proliferation, differentiation, migration and survival to affect multiple biological processes like development, tumorigenesis, fibrosis, wound healing and immune response.

Reduction of cutaneous scarring has been shown by use of an neutralizing antibody to TGFβ (Shah et al. J Cell Sci. 1994 May; 107 (Pt 5):1137-57), J Cell Sci. 1995 March; 108 (Pt 3):985-1002).

Roles of TGFβ in wound healing are known to the public (Martin Science. 1997 Apr. 4; 276(5309):75-81).

In addition, TGFβ is known for its function in the human hair cycle by suppression of proliferation of epithelial cells and stimulation of synthesis of caspases, and thereby being included in the catagen cascade in male pattern baldness. Modulation of TGFβ might therefore delay the premature entry of mens hair growth into their catagen phase. (Hibino et al. J Dermatol Sci. 2004 June; 35(1):9-18).

Angiogenesis, the formation of vasculature from existing blood vessels is described for decades (Folkman Nat Rev Drug Discov. 2007 April; 6(4):273-86, Annu Rev Med. 2006; 57:1-18, Curr Mol Med. 2003 November; 3(7):643-51, Semin Oncol. 2001 December; 28(6):536-42, Alghisi Endothelium. 2006 March-April; 13(2):113-35, Stupack et al. Curr Top Dev Biol. 2004; 64:207-38,).

It is a highly dynamic and complex process depending on growth factor receptors and adhesion receptors. Integrins are the principal adhesion receptors on endothelial cells to interact with their extracellular environment. Inhibition of αvβ3 and αvβ5-integrins was shown to disturb angiogenesis (Eliceiri et al. Curr Opin Cell Biol. 2001 October; 13(5): 563-8, Nisato et al. Angiogenesis. 2003; 6(2):105-19, Eliceiri et al. Cancer J. 2000 May; 6 Suppl 3: S245-9).

In skin, αv-integrins also play an important role in angiogenesis (Perruzzi et al. J Invest Dermatol. 2003 June; 120(6):1100-9).

Furthermore, it has been shown that several pathogens like viruses can use the interaction with integrins to populate cells. Therefore, it is feasible that integrin inhibitors can prevent infections with pathogens through skin lesions, when applied in a topical formulation. Stewart, Phoebe L.; Nemerow, Glen R. Cell integrins: commonly used receptors for diverse viral pathogens. Trends in Microbiology (2007), 15(11), 500-507. For example, herpes virus 8 envelope glycoprotein B mediates cell adhesion via its RGD sequence (Wang et al. J Virol. 2003 March; 77(5):3131-47.) Other examples are: human cytomegalovirus (Wang et al. Nat Med. 2005 May; 11(5):515-21), and hantavirus (Gavrilovskaya et al. Nat Med. 2005 May; 11(5):515-21).

Special reference is given to the publications of Simon L. Goodman, Horst Kessler et al., *J. Med. Chem.* 2002, 45, 1045-1051, Martin Pfaff, Horst Kessler et al., *THE JOURNAL OF BIOLOGICAL CHEMISTRY, Vol.* 269, No. 32, Issue of August 12, pp. 20233-20238, 1994, Sally J. DeNardo et al., *CANCER BIOTHERAPY & RADIOPHARMACEUTICALS*, Vol. 15, No. 1, 2000, and Wipff, P.-J., Hinz, B., Integrins and the activation of latent transforming growth factor β1—An intimate relationship, *Eur. J. Cell Biol.* (2008), the disclosure of which in their entirety is explicitly incorporated herein by reference.

The instant invention preferably relates to:

A composition, preferably a composition for non-therapeutic use, comprising one or more cyclic peptides and one or more vehicles.

A composition, preferably a composition for topical use comprising one or more cyclic peptides and one or more topically acceptable vehicles.

The meaning of the term "peptide" or "peptides" is known in the art. According to the invention, peptides are preferably defined as amides derived from two or more (the same or different) amino carboxylic acid molecules (i.e. amino acids) by formation of a covalent bond from the carbonyl carbon of one to the nitrogen atom of another with formal loss of water. The term is usually applied to structures formed from α-amino acids, but it preferably also includes those derived from any amino carboxylic acid or amino acid.

Cyclic peptides and methods for obtaining cyclic peptides are known in the art. According to the invention, cyclic peptides are preferably peptides in which a bridge or a link is formed between two amino acids that are part of the peptide or constitute the peptide. The bridge can be formed between amino acids having a reactive group (other than the amino and the carboxyl group that are essential for the respective amino acid), preferably, such as a sulphide group. Generally, peptides comprising two or more, preferably two amino acids having such a reactive group can be cyclised. For example, a peptide comprising two amino acids that have a sulphide group can be cyclised under conditions wherein a disulphite bridge between the sulphide groups of the two amino acids containing a sulphide group is formed. Examples of amino acids having a sulphide group and thus being capable of forming a bridge, i.e. a disulphite bridge include, but are not limited to penicillamine and cysteine. Peptides in which the bonds forming the ring are not solely peptide linkages (or eupeptide linkages according to the IUPAC) are preferably referred to as heterodetic cyclic peptides. In this case, the bonds between the reactive groups (other than the amino and the carboxyl group that are essential for the respective amino acid) forming the ring are preferably referred to as "bridge". Alternatively, peptides in which the bonds forming the ring are solely peptide linkages (or eupeptide linkages according to the IUPAC) are preferably referred to as homodetic cyclic peptides. According to the invention, both heterodetic cyclic peptides and homodetic cyclic peptides can be used. Generally, peptides comprised of three or more, preferably four or more amino acids can be cyclised. In principle, the number of amino acids in a cyclic peptide is not limited. However, the targeted or specific preparation of cyclic peptides being comprised of 30 or more amino acids is complex. Additionally, in many cases, the specific advantageous properties that are inherent to "smaller" cyclic peptides, such as cyclic peptides being comprised of four to 30 or preferably 4 to 20 amino acids, tend to disappear with increasing ring sizes and thus increasing numbers of amino acids constituting said cyclic peptides.

It is well within the skill in the art to prepare cyclic peptides, as well cyclic peptides being comprised of naturally occurring amino acids exclusively as cyclic peptides comprising non-natural amino acids. For example, conventional protection and activation chemistry can be used. Typically, the amino functionality of a first amino acid is protected with a removable amino protecting group and the carboxyl functionality of a second amino acid is protected with a removable carboxyl protecting group. Suitable amine protecting groups include, without limitation, benzoyloxycarbonyl (Cbz), tert-butoxycarbonyl (t-Boc), and 9-flourenylmethloxycarbonyl (FMOC). The carboxyl group may be protected protecting by forming an acid or base labile ester such as a methyl, ethyl, benzyl, or trimethylsilyl esters. After protection, the first and second amino acids are reacted in a suitable solvent such as water or DMF in the presence of an in situ activating agent such as N.N'-dicyclohexylcarbodiimide (DCCI), diisopropylcarbodiimide (DIPCDI), or 1-ethyl-3-(3'-dimethylaminopropyl)carbodiimide (EDCI) to effect peptide bond formation. Reactive moieties on the side chains of either amino acid are protected with protecting groups such as teff-butyl or benzyl for OH and SH; methyl, ethyl, tert-butyl or benzyl for carboxyl groups, 2,2,5,7,8-pentamethylchroman-6-sulphonyl for the —NHC(NH$_2$)═NH functionality of Arg, and trityl for the imidazole group of His. Following the coupling reaction, selective deprotection of the amino group of the first amino acid is accomplished by acid hydrolysis under conditions that do not remove the carboxyl protecting group of the second amino acid. The procedure is repeated with a additional amino protected amino acids. Solid phase synthesis, such as the well-known Merrifield method, is especially useful for synthesizing the peptides of the invention. Generally, the synthesis of the cyclic peptides is done by first synthesising a linear peptide of the desired sequence, for example as described above, followed by a cyclization step. Suitable methods and conditions for cyclizing a linear peptide into a cyclic peptide are known in the art.

The incorporation of non-natural amino acids into peptides is described in Hohsaka T, Sisido M "Incorporation of non-natural amino acids into proteins" Curr. Opin. Chem. Biol. 6: 809-815 (2002); Noren C J et al. "A general method for site-specific incorporation of unnatural amino acids into proteins" Science 244: 182-188 (1989); and Hodgson, David R. W., Sanderson, John M., "The Synthesis of Peptides and Proteins Containing Non-Natural Amino Acids", Chem. Soc. Rev., 2004, 33, 422-430, the disclosures of which are hereby incorporated by reference.

The instant invention preferably relates to:

A composition as described above/below, wherein said cyclic peptide is a homodetic cyclic peptide. The meaning of the terms "homodetic" and "homodetic cyclic peptide" is known in the art. According to the invention, a homodetic cyclic peptide preferably is a cyclic peptide in which the ring (or backbone of the cyclic peptide) consists solely of aminoacid residues in peptide linkage (or in eupeptide linkage according to the nomenclature of the IUPAC).

A composition as described above/below, wherein said cyclic peptide is comprised of 4 to 30 amino acids, preferably 4 to 20 amino acids, more preferably 4 to 15 amino acids, even more preferably 4 to 12 and especially 4 to 10 amino acids, selected from the group consisting of naturally occurring amino acids and non-naturally occurring amino acids. Examples of preferred cyclic peptides, preferably homodetic cyclic peptides, are comprised of 4 amino acids, 5 amino acids, 6 amino acids, 7 amino acids, 8 amino acids, 9 amino acids, 10 amino acids or 12 amino acids, selected from the group consisting of naturally occurring amino acids and non-naturally occurring amino acids. Examples of naturally occurring amino acids and non-naturally occurring amino acids are given below.

A composition as described above/below, wherein said cyclic peptide comprises one or more non-naturally occurring amino acids.

A composition according to one of the claims 1 to 4, wherein said cyclic peptide comprises the Arg-Gly-Asp sequence (or RGD sequence in the one letter code for amino acids). According to the invention, the Arg-Gly-Asp sequence is preferably comprised exclusively of the respective L-amino acids, i.e comprised of L-Arg, L-Gly and L-Asp.

As used herein, the term "amino acid" is preferably intended to include naturally occurring amino acids as well as non-naturally occurring amino acids and preferably also includes any small molecule having at least one carboxyl group and at least one primary or secondary amino group capable of forming a peptide bond. The term peptide" is preferably intended to include any molecule having at least one peptide bond. The term "peptide" is preferably also embraces structures as defined above having one or more linkers, spacers, terminal groups or side chain groups which are not amino acids.

The terms "naturally occurring amino acids" and "non-naturally occurring amino acids" are well understood in the art.

However, a non-exhausting list of non-naturally amino acids as well as naturally occurring amino acids can preferably be found in "The Peptides", Volume 5 (1983), Academic Press, Chapter VI, by D. C. Roberts and F. Vellacio.

According to the invention, the naturally occurring amino acids are preferably selected from the consisting of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, and more preferably exclusively selected from the L forms thereof.

According to the invention, the non-naturally occurring amino acids are preferably selected from the group consisting of:

i) the D forms of naturally occurring amino acids, i.e. the D forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, ii) the N-alkyl derivatives of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, preferably including both the D and L forms thereof, and iii) Lys(Ac), Lys(AcNH$_2$), Lys(AcSH), Tic, Asp(OR), Cha, Nal, 4-Hal-Phe, homo-Phe, Phg, Pya, Abu, Acha, Acpa, Aha, Ahds, Aib, Aos, N-Ac-Arg, Dab, Dap, Deg, hPro, Nhdg, homoPhe, 4-Hal-Phe, Phg, Sar, Tia, Tic and Tle, preferably including both the D and L forms thereof; wherein R is alkyl having 1-18 carbon atoms, Hal is F, Cl, Br, I Ac is alkanoyl having 1-10 carbon atoms, aroyl having 7-11 carbon atoms or aralkanoyl having 8-12 carbon atoms.

The term "dermatologically acceptable", as used herein, preferably means that the composition or components described suitable for use in contact with human skin without risk of toxicity, incompatibility instability, allergic response, and the like.

All terms such as "skin ageing", "signs of skin ageing", "topical application", and the like are preferably used in the sense in which they are generally and widely used in the art of developing, testing and marketing cosmetic and personal care products.

The term "cosmetic composition" or preferably more briefly just "composition" in accordance with the present invention preferably relates to a formulation that can be used for cosmetic purposes, purposes of hygiene and/or as a basis for delivery of one or more pharmaceutical ingredients. It is also possible that these formulations are used for two or more of these purposes at one time. Thus, the terms "cosmetics," "cosmetic composition" and/or "composition" as used herein, preferably include without limitation, lipstick, mascara, rouge, foundation, blush, eyeliner, lipliner, lip gloss, facial or body powder, sunscreens and blocks, nail polish, mousse, sprays, styling gels, nail conditioner, whether in the form of creams, lotions, gels, ointments, emulsions, colloids, solutions, suspensions, compacts, solids, pencils, spray-on formulations, brush-on formulations and the like. "Personal care products" preferably include, without limitation, bath and shower gels, shampoos, conditioners, cream rinses, hair dyes and coloring products, leave-on conditioners, sunscreens and sunblocks, lip balms, skin conditioners, cold creams, moisturizers, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, cleansers, skin gels, rinses, whether in solid, powder, liquid, cream, gel, ointment, lotion, emulsions, colloids, solutions, suspensions, or other form. "Pharmaceutical preparations" in accordance with the present invention preferably include, without limitation, carriers for dermatological purposes, including topical and transdermal application of pharmaceutically active ingredients. These can be in the form of gels, patches, creams, nose sprays, ointments, lotions, emulsions, colloids, solutions, suspensions, powders and the like. Compositions in accordance with the invention preferably include cosmetics, personal care products and pharmaceutical preparations.

The terms "skin ageing" or "signs of skin ageing" preferably include, but are not limited to, all outward visibly and tactilely perceptible manifestations as well as any other macro or micro effects due to skin ageing. Such signs may be induced or caused by intrinsic factors or extrinsic factors, e.g. chronological ageing and/or environmental damage. The signs may result from processes which preferably include, but are not limited to, the development of textural discontinuities, such as wrinkles and coarse deep wrinkles, skin lines, crevices, bumps, large pores (e.g. associated with adnexal structures such as sweat gland ducts, sebaceous glands, or hair follicles), or unevenness or roughness of the skin, loss of skin elasticity (loss and/or in activation of functional skin elastin), sagging (including puffiness in the eye area and jowls), loss of skin firmness, loss of skin tightness, loss of skin recoil from deformation, discoloration (including (black) under eye circles), blotching, sallowness, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin. Particularly preferred in accordance with the present invention, the signs of skin aging are wrinkles and the compositions of the present invention are, in certain preferred embodiments, useful in fighting, treating or preventing wrinkles.

As used herein, prophylactically regulating a skin condition preferably includes delaying, minimizing and/or preventing visible and/or tactile discontinuities in skin (e.g., texture irregularities in the skin which may be detected visually or by feel), including signs of skin aging.

As used herein, therapeutically regulating skin condition preferably includes ameliorating, e.g., diminishing, minimizing and/or effacing, discontinuities in skin, including signs of skin aging. Some of the products produced using the compositions of the present invention and indeed the compositions themselves may be used for prophylactically or therapeutically regulating a skin condition.

Some of the products and compositions of the present invention are useful for improving skin appearance and/or feel of skin exhibiting signs of skin aging. For example, preferred compositions of the present invention are useful for regulating the appearance of skin conditions by providing an immediate visual improvement in skin appearance following application of the composition to the skin. Generally speaking, compositions of the present invention which further contain particulate materials will be most useful for providing the immediate visual improvement.

Some of the compositions of the present invention may also provide additional benefits, including stability, absence of significant (consumer-unacceptable) skin irritation, anti-inflammatory activity and good aesthetics.

In certain preferred aspects, the present invention is useful for improving the physiological state and/or the physical appearance of human skin, in particular to reduce the signs of skin aging that are generated by sun exposure, physical and hormonal stress, abrasion, nutritional effects and other similar causes. The compositions may often be used to prevent the signs of aging and/or to treat them in order to afford the consumer who uses them, a more youthful appearance.

Preferred cyclic peptides according to the invention are the cyclic peptides according to formula I, $$\text{Cyclo-(Arg-Gly-Asp-}\Omega\text{)} \qquad \qquad \text{I,}$$

wherein $\Omega$ is an amino acid subsequence comprised of one or more amino acids selected from the group consisting of the L- and D-forms of:

hPro, Ahds, Aos, Nhdg, Acha, Aib, Acpa, Tle, Gly, Ala, β-Ala, Asn, Asp, Asp(OR), Arg, Cha, Cys, Gln, Glu, His, Ile, Leu, Lys, Lys(Ac), Lys(AcNH$_2$), Lys(AcSH), Met, Nal, Nle, Orn, Phe, 4-Hal-Phe, homo-Phe, Phg, Pro, Pya, Ser, Thr, Tia, Tic, Trp, Tyr or Val, and the N-alkyl derivatives thereof, wherein R is alkyl having 1-18 carbon atoms, Hal is F, Cl, Br, I, Ac is alkanoyl having 1-10 carbon atoms, aroyl having 7-11 carbon atoms or aralkanoyl having 8-12 carbon atoms, and the salts and solvates thereof.

In the cyclic peptide according to formula I, $\Omega$ is preferably comprised of 1 to 20 amino acids as defined above/below, more preferably comprised of 1 to 10 amino acids as defined above/below, even more preferably comprised of 1 to 6 amino acids as defined above/below, and especially comprised of 1, 2, 3 or 4 amino acids as defined above/below.

In the cyclic peptide according to formula I, $\Omega$ is especially preferably comprised of two amino acids as defined above/below.

Preferred cyclic peptides according to the invention are the cyclic peptides of the formula Ia $$\text{cyclo-(Arg-Gly-Asp-X-Y)} \qquad \qquad \text{Ia,}$$

in which

X is an amino acid selected from the group consisting of Cha, Nal, Phe, 2-R$^1$-Phe, 3-R$^1$-Phe, 4-R$^1$-Phe, homo-Phe, Phg, Thi, Trp, Tyr and derivatives of Tyr, wherein the OH group can be etherified by alkyl radicals having 1-18 carbon atoms, preferably including both the D and L forms thereof, more preferably consisting of the D or L forms thereof and especially consisting of the D forms thereof, R¹ is NH$_2$, NO$_2$, I, Br, Cl, F, alkyl having 1-18 carbon atoms, Ar, Ar—O or ³H, Ar is phenyl which can optionally be substituted once or twice by NH$_2$, NO$_2$, I, Br, Cl, F, alkyl having 1-6 carbon atoms or ³H, Y is an amino acid selected from the group consisting of Gly, derivatives of Gly wherein the α N-atom is substituted by R², derivatives of Gly wherein the α-C atom is substituted by R³ and/or R⁴, and derivatives of Gly wherein both the α N-atom is substituted by R² and the α C-atom is substituted by R³ and/or R⁴, with the proviso that Gly is substituted at least once in the manner indicated,
preferably including both the D and L forms thereof, more preferably consisting of the D or L forms thereof and especially consisting of the L forms thereof,

R², R³, or R⁴ are each independently of one another alkyl having 1-18 carbon atoms, or else R² and R³ or

R³ and R⁴ in each case together are otherwise a branched or unbranched alkylene chain having 3 to 18 carbon atoms, so that therein either the α N atom and the α C atom together with the alkylene chain, or the α C atom alone with the alkylene chain, forms a ring, and derivatives of said amino acids, preferably selected from the group consisting of N-alkyl derivatives of said amino acids, preferably N—C1-C4-alkyl derivatives of said amino acids, aspartic acid β-esters, and N-guanidine-acyl derivatives of arginine, and the physiologically acceptable salts and solvates thereof.

The abbreviations of amino acid residues shown above and below represent the residues of the following amino acids:

Abu 4-aminobutyric acid
Acha α-aminocyclohexanecarboxylic acid
Acpa α-aminocyclopentanecarboxylic acid
Aha 6-aminohexanoic acid
Ahds 16-aminohexadecanoic acid
Aib 3-aminoisobutyric acid
Ala alanine
Aos 8-aminooctanoic acid
Asn asparagine
Asp aspartic acid
Asp(OR) aspartic acid (β ester)
Arg arginine
N-Ac-Arg N-guanidinoacylarginine
Cha 3-cyclohexylalanine
Dab 2,4-diaminobutyric acid
Dap 2,3-diaminopropionic acid
Deg diethylglycine
Gln glutamine
Glu glutamic acid
Gly glycine
hPro homo proline=pipecolic acid
His histidine
Ile isoleucine
Leu leucine
Lys lysine
Nal 3-(2-naphthyl)alanine
Nhdg N-hexadecylglycine
Nle norleucine
Phe phenylalanine
homoPhe homophenylalanine
4-Hal-Phe 4-halophenylalanine
Phg phenylglycine
Pro proline
Sar sarcosine (N-methylglycine)
Tia 3-(2-thienyl)alanine
Tic tetrahydroisoquinoline-3-carboxylic acid
Thr threonine
Tle tert-leucine(C$_\alpha$-tert-butylglycine)
Trp tryptophan
Tyr tyrosine
Val valine.

In addition, the meaning of the following abbreviations is as follows:
BOC tert-butoxycarbonyl
Bzl benzyl
DCCI dicyclohexylcarbodiimide
DMF dimethylformamide
EDCI N-ethyl-N'-(3-dimethylaminopropyl)-carbodiimide× HCl
Et ethyl
Fmoc 9-fluorenylmethoxycarbonyl
HOBt 1-hydroxybenzotriazole
Me methyl
Mtr 4-methoxy-2,3,6-trimethylphenylsulfonyl
NMe N-methylated α-amino group
OBut tert-butyl ester
OMe methyl ester
OEt ethyl ester
POA phenoxyacetyl
TBTU 2-(1H-benzotriazol-1-yl)-1,1,3,3-tetramethyluronium tetrafluoroborate
TFA trifluoroacetic acid.

Where the abovementioned amino acids can occur in a number of enantiomeric forms, then all of these forms and also their mixtures (e.g. the DL forms) are included above and below, for example as constituents of the compounds of the formula I. The amino acids, for example as a constituent of compounds to the formula I, can also be provided with appropriate protecting groups which are known per se.

Above and below, the radicals X and Y have the meanings given in the case of the formulae Ia and Ib unless expressly stated otherwise. The letters used for said radicals X and Y preferably have nothing to do with the corresponding single-letter codes for amino acids.

With respect to the cyclic peptides according to the invention, the amino acids and/or amino acid derivatives, especially the N-alkyl derivatives of said amino acids, alkyl is preferably selected from methyl, ethyl, isopropyl, n-butyl, sec-butyl and tert-butyl. However, alkyl is furthermore also preferably selected from n-pentyl, isopentyl, neopentyl, n-hexyl, n-heptyl, n-octyl, n-nonyl, n-decyl and n-hexadecyl.

In the cyclic peptides according to formulae Ia-, X is preferably Phe, also preferably D-Phe, but also Phe(4-Hal), especially Phe(4-F) or Phe(4-Cl) and, homo-Phe or Phg, the D forms also being equally preferred.

In the cyclic peptides according to formulae Ia-Ie, Y is preferably a hydrophobic amino acid residue, preferably a hydrophobic amino acid residue selected from the group consisting of Gly, Ala, Val, Leu, Nle, Ile and Acha.

The invention relates in particular to those compounds of the formula I in which at least one of the radicals mentioned has one of the abovementioned preferred meanings.

A preferred group of cyclic peptides according the invention are the cyclic peptides of formula subformula Ib, cyclo-(Arg-Gly-Asp-X-Y)   Ib, in which
X is selected from the group consisting of D-Phe, Phe, D-homoPhe, homoPhe, D-Phg, Phg, Phe(4-F), D-Phe(4-F), D-Phe(4-Cl) and Phe(4-Cl); and
Y is selected from the group consisting of Nle, hPro, Ahds, Aos, Nhdg, Acha, Aib, Acpa, Tle, Ala, Leu or Ile, wherein the D and L forms are equally preferred,
and the salts and solvates thereof.

An even more preferred group of cyclic peptides according the invention are the cyclic peptides of formula subformula Ic,

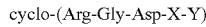

wherein
X is selected from consisting of D-Phe or Phe, and
Y is selected from the group consisting of Ahds, hPro, Aos, Nhdg, Acha, Aib, Acpa or Tle, the D and L forms being equally preferred,
and the salts and solvates thereof.

An additionally preferred group of cyclic peptides according the invention are the cyclic peptides of formula subformula Id,

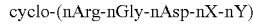

wherein
X and Y in each case independently of one another are:
Gly, Ala, β-Ala, Asn, Asp, Asp(OR), Arg, Cha, Cys, Gln, Glu, His, Ile, Leu, Lys, Lys(Ac), Lys(AcNH$_2$), Lys (AcSH), Met, Nal, Nle, Orn, Phe, 4-Hal-Phe, homo-Phe, Phg, Pro, Pya, Ser, Thr, Tia, Tic, Trp, Tyr or Val, which amino acid residues can also be derivatized,
R is alkyl having 1-18 carbon atoms,
Hal is F, Cl, Br, I,
Ac is alkanoyl having 1-10 carbon atoms, aroyl having 7-11 carbon atoms or aralkanoyl having 8-12 carbon atoms,
n denotes no substituent or is a substituent on the α-amino function of the respective amino acid residue, selected from the group consisting of alkyl radicals R, benzyl and aralkyl radicals having 7-18 carbon atoms, with the proviso that at least one amino acid residue has a substituent n and
with the further proviso that, where residues of optically active amino acids and amino acid derivatives are involved, both the D and the L forms are included,
and salts and solvates thereof.

A more preferred group of cyclic peptides according to formula Id are the cyclic peptides of formula Ie,

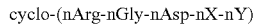

wherein
X and Y in each case independently of one another are Gly, Ala, β-Ala, Asn, Asp, Asp(OR), Arg, Cha, Cys, Gln, Glu, His, Ile, Leu, Lys, Lys(Ac), Lys(AcNH$_2$), Lys(AcSH), Met, Nal, Nle, Orn, Phe, 4-Hal-Phe, homo-Phe, Phg, Pro, Pya, Ser, Thr, Tia, Tic, Trp, Tyr or Val,
R is alkyl having 1-18 carbon atoms,
Hal is F, Cl, Br, I,
Ac is alkanoyl having 1-10 carbon atoms, aroyl having 7-11 carbon atoms or aralkanoyl having 8-12 carbon atoms,
n denotes a hydrogen atom or is a C1-C4-alkyl radical on the alpha-amino function of the respective amino acid residue,
with the proviso that on at least one amino acid residue, n is a C1-C4-alkyl radical and that, where residues of optically active amino acids and amino acid derivatives are involved, both the D and L forms are included;
and the salts and solvates thereof.

Preferably, the cyclic peptide of the formula I, Ia, Ib, Ic, Id and/or Ie is not cyclo-(Arg-Gly-Asp-NMe-Phe-Gly).

In the cyclic peptides according to the invention that comprise the Arg-Gly-Asp sequence, all the amino acid residues Arg, Gly and Asp are preferably present in the natural L configuration.

A further preferred group of compounds can be expressed by the formulae I, Ia, Ib, Ic, Id and/or Ie, more preferably by the formulae Ia, Ib, Ic, Id and/or Ie, in which only one of the amino acid residues X or Y is present in the D form, whereas all the others are in the L configuration.

Furthermore, particular preference is given to all physiologically compatible salts of the compounds which come under one or more of formulae I, Ia, Ib, Ic, Id and/or Ie.

A further preferred group of compounds can be expressed by the subformula Ic, which corresponds to the subformulae Ia and Ib and to the formula I but in which only one of the amino acid residues X or Y is present in the D form, whereas all the others are in the L configuration.

Furthermore, particular preference is given to all physiologically compatible salts of the compounds which come under the subformulae I, Ia, Ib, Ic, Id and/or Ie.

The cyclic peptides according the invention and especially the cyclic peptides according to I, Ia, Ib, Ic, Id and/or Ie and also the starting materials for their preparation are preferably prepared by known methods, preferably as described in the literature (for example in the standard works such as Houben-Weyl, Methoden der organischen Chemie [Methods of Organic Chemistry], Georg-Thieme-Verlag, Stuttgart), in particular under reaction conditions which are known and appropriate for the said reactions. In this context, use can also be made of known variants which are not mentioned in any greater detail here.

If desired, the starting substances can also be formed in situ, so that they are not isolated from the reaction mixture but are immediately reacted further to give the cyclic peptides according to the invention and especially the cyclic peptides according to formula I, Ia, Ib, Ic, Id and/or Ie. The cyclic peptides according to the invention and especially the cyclic peptides according to formula I, Ia, Ib, Ic, Id and/or Ie can be obtained by liberating them from their functional derivatives by solvolysis, in particular hydrolysis, or by hydrogenolysis.

Preferred starting materials for the solvolysis or hydrogenolysis are those which contain appropriate protected amino and/or hydroxyl groups instead of one or more free amino and/or hydroxyl groups, preferably those which carry an amino protecting group instead of a hydrogen atom which is attached to a nitrogen atom, examples being those which correspond to the formula I but which, instead of an NH$_2$ group, contain an NHR' group (where R' is an amino protecting group, e.g. BOC or CBZ).

Other preferred starting materials are those which carry a hydroxyl protecting group instead of the hydrogen atom of a hydroxyl group, for example those which correspond to the formula I but contain, instead of a hydroxyphenyl group, a R"O-phenyl group (where R" is a hydroxyl protecting group).

It is also possible for two or more—identical or different—protected amino and/or hydroxyl groups to be present in the molecule of the starting material. If the protecting groups present are different from one another, then in many cases they can be eliminated selectively.

The expression "amino protecting group" is generally known and relates to groups which are suitable for protecting (for blocking) an amino group from chemical reactions but which are readily removable after the desired chemical reaction has been carried out at other positions of the molecule. Typical of such groups are, in particular, unsubstituted or substituted acyl, aryl, aralkoxymethyl or arakyl groups. Since the amino protecting groups are removed after the desired reaction (or reaction sequence), their nature and size is otherwise not critical; however, preference is given to those having 1-20, in particular 1-8, carbon atoms. The term "acyl group" is to be interpreted in its widest sense in connection with the present process. It includes acyl groups derived from aliphatic, araliphatic, aromatic or heterocyclic carboxylic acids or sulfonic acids and, in particular, alkoxycarbonyl, aryloxycarbonyl and, above all, aralkoxycarbonyl groups. Examples of such acyl groups are alkanoyl such as acetyl, propionyl, butyryl; aralkanoyl such as phenylacetyl; aroyl such as benzoyl or toluoyl; aryloxyalkanoyl such as POA; alkoxycarbonyl such as methoxycarbonyl, ethoxycarbonyl, 2,2,2-trichlorethoxy-carbonyl, BOC, 2-iodoethoxycarbonyl; aralkyloxycarbonyl such as CBZ ("carbobenzoxy"), 4-methoxybenzyloxy-carbonyl, FMOC; and arylsulfonyl such as Mtr. Preferred amino protecting groups are BOC and Mtr, and also CBZ, Fmoc, benzyl and acetyl.

The expression "hydroxyl protecting group" is also generally known and relates to groups which are suitable for protecting a hydroxyl group from chemical reactions but which are readily removable after the desired chemical reaction has been carried out at other positions of the molecule. Typical of such groups are the abovementioned unsubstituted or substituted aryl, aralkyl or acyl groups, and also alkyl groups. The nature and size of the hydroxyl protecting groups is not critical, since they are removed again after the desired chemical reaction or reaction sequence; preference is given to groups having 1-20, especially 1-10, carbon atoms. Examples of hydroxyl protecting groups include benzyl, p-nitrobenzoyl, p-toluenesulf-onyl, tert-butyl and acetyl, with particular preference being given to benzyl and tert-butyl. The COOH groups in aspartic acid and glutamic acid are preferably protected in the form of their tert-butyl esters (e.g. Asp(OBut)).

The functional derivatives of the cyclic peptides according to the invention and especially of the cyclic peptides according to formula I, Ia, Ib, Ic, Id and/or Ie which are to be used as starting materials can be prepared by customary methods of amino acid and peptide synthesis, as are described, for example, in the patent applications and standard works mentioned, including for example by the solid-phase method according to Merrifield (B. F. Gysin and R. B. Merrifield, J. Am. Chem. Soc. 94, 3102 ff. (1972)).

The liberation of the compounds of the cyclic peptides according to the invention and especially of the cyclic peptides according to formula I, Ia, Ib, Ic, Id and/or Ie from their functional derivatives is preferably carried out-depending on the protecting group used—with, for example, strong acids, expediently with TFA or perchloric acid, but also with other strong inorganic acids, such as hydrochloric acid or sulfuric acid, strong organic carboxylic acids, such as trichloroacetic acid, or sulfonic acids such as benzene- or p-toluenesulfonic acid. The presence of an additional inert solvent is possible but not always necessary. Suitable inert solvents are preferably organic, for example carboxylic, acids such as acetic acid, ether such as tetrahydrofuran or dioxane, amides such as DMF, halogenated hydrocarbons such as dichloromethane, and also alcohols such as methanol, ethanol or isopropanol, and water. Also suitable are mixtures of the abovementioned solvents. TFA is preferably used in excess without the addition of a further solvent, perchloric acid in the form of a mixture of acetic acid and 70% perchloric acid in a ratio of 9:1. The reaction temperatures for the cleavage are expediently between about 0 and about 50°; it is preferably carried out between 15 and 30° (room temperature).

The groups BOC, OBut and Mtr can be removed, for example, preferably using TFA in dichloromethane or with about 3 to 5 N HCl in dioxane at 15-30°, while the FMOC group can be eliminated with an approximately 5 to 50% solution of dimethylamine, diethylamine or piperidine in DMF at 15-30°.

Protecting groups which can be removed by hydrogenolysis (e.g. CBZ or benzyl) can be eliminated, for example, by treatment with hydrogen in the presence of a catalyst (e.g. a noble metal catalyst such as palladium, preferably on a support such as charcoal). Suitable solvents in this context are those mentioned above, especially, for example, alcohols such as methanol or ethanol or amides such as DMF. The hydrogenolysis is carried out, as a rule, at temperatures between about 0 and 100° and at pressures of between about 1 and 200 bar, preferably at 20-30° and 1-10 bar. Hydrogenolysis of the CBZ group, for example, takes place readily on 5 to 10% Pd—C in methanol or using ammonium formate (instead of $H_2$) on Pd—C in methanol/DMF at 20-30°.

The cyclic peptides according to the invention and especially the cyclic peptides according to formula I, Ia, Ib, Ic, Id and/or Ie can also be obtained by cyclization of linear peptides having the same amino acid sequence as the desired cyclic peptide, preferably under the conditions of a peptide synthesis. In this case, the reaction is expediently carried out in accordance with customary methods of peptide synthesis as described, for example, in Houben-Weyl, l.c., Volume 15/11, Pages 1 to 806 (1974).

The reaction is preferably carried out in the presence of a dehydrating agent, for example a carbodiimide such as DCCI or EDCI, and additionally propanephosphonic anhydride (cf. Angew. Chem. 92, 129 (1980)), diphenyl phosphoryl azide or 2-ethoxy-N-ethoxycarbonyl-1,2-dihydroquinoline, in an inert solvent, for example a halogenated hydrocarbon such as dichloromethane, an ether such as tetrahydrofuran or dioxane, an amide such as DMF or dimethylacetamide, a nitrile such as acetonitrile, or in mixtures of these solvents, at temperatures between about −10 and 40°, preferably between 0 and 30°. In order to promote intramolecular cyclization over intermolecular peptide bonding, it is expedient to work in dilute solutions (dilution principle).

Instead of linear peptides having the same amino acid sequence as the desired cyclic peptide, suitable reactive derivatives of said linear peptides can also be employed in the reaction, for example those in which reactive groups are intermediately blocked by protecting groups. Said linear peptides can be used, for example, in the form of their activated esters which are expediently formed in situ, for example by addition of HOBt or N-hydroxysuccinimide.

The starting materials for the manufacture of the cyclic peptides are either novel, commercially available or they are readily available by methods known in the art. In any case, they can preferably be prepared by known methods, for example the abovementioned methods of peptide synthesis and of elimination of protecting groups.

The derivatization of a cyclopeptide which corresponds per se to a compound of the formula I, Ia, Ib, Ic, Id and/or Ie is preferably likewise effected by methods known per se, as are known for the alkylation of amines, the esterification of carboxylic acids or nucleophilic substitution at aliphatic carbon atoms and are described in any textbook of organic chemistry, for example J. March, Adv. Org. Chem., John Wiley & Sons N.Y. (1985).

A base of a cyclic peptide according to the invention and especially the days of a cyclic peptide according to formula I, Ia, Ib, Ic, Id and/or Ie can be converted into the associated acid addition salt using an acid. Suitable acids for this reaction are, in particular, those which yield physiologically acceptable salts. Thus inorganic acids can be used, examples being sulfuric acid, nitric acid, hydrohalic acids such as hydrochloric acid or hydrobromic acid, phosphoric acid such as orthophosphoric acid, sulfamic acid, and also organic acids, especially aliphatic, alicyclic, araliphatic, aromatic or heterocyclic mono- or polybasic carboxylic, sulfonic or sulfuric acids, for example formic acid, acetic acid, propionic acid, pivalic acid, diethyl-acetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, laurylsulfuric acid. Salts with physiologically unacceptable acids, for example picrates, can be used for isolating and/or purifying the compounds of the formula I.

Alternatively, an acid of a cyclic peptide according to the invention and especially an acid of a cyclic peptide according to formula I, Ia, Ib, Ic, Id and/or Ie can be converted into one of its physiologically acceptable metal or ammonium salts by reaction with a base. Particularly suitable salts in this context are the sodium, potassium, magnesium, calcium and ammonium salts, and also substituted ammonium salts, for example the dimethyl-, diethyl- or diisopropylammonium salts, monoethanol-, diethanol- or triethanolammonium salts, cyclohexylammonium salts, dicyclohexylammonium salts, dibenzylethylenediammonium salts, and also, for example, salts with N-methyl-D-glucamine or with arginine or lysine.

Preferred cyclic peptides for all aspects of the instant invention are preferably selected from the group consisting of the cyclic peptides according to formula I, Ia, Ib, Ic, Id and/or Ie, more preferably selected from consisting of the cyclic peptides according to formula Ia, Ib, Ic and/or Id, even more preferably selected from the group consisting of the cyclic peptides according to formula Ib, Ic and/or Ie, and especially preferred selected from the group consisting of the cyclic peptides according to formula Ic.

A preferred cyclic peptide for all aspects of the instant invention is Cyclo-(Arg-Gly-Asp-DPhe-Acha), and/or a salt or solvate thereof.

The cyclic peptides according to the invention and especially the cyclic peptides according to formula I, Ia, Ib, Ic, Id and/or Ie possess very valuable properties. In particular, they act as integrin inhibitors, in which context they preferably modulate and especially preferably inhibit the interactions of $\beta_3$- or $\beta_5$-integrin receptors with ligands. The compounds are preferably particularly active in the case of the integrins $a_V\beta_3$, $a_V\beta_5$ and/or $a_{IIb}\beta_3$, but also relative to $a_V\beta_1$-, $a_V\beta_6$- and/or $a_V\beta_8$ receptors. These actions can be demonstrated, for example, according to the method described by J. W. Smith et al. in J. Biol. Chem. 265, 12267-12271 (1990). In addition, there are anti-inflammatory effects.

The dependency of the development of angiogenesis on the interaction between vascular integrins and extra-cellular matrix proteins is described by P. C. Brooks, R. A. Clark and D. A. Cheresh in Science 264, 569-71 (1994).

The possibility of inhibiting this interaction is described by P. C. Brooks, A. M. Montgomery, M. Rosenfeld, R. A. Reisfeld, T.-Hu, G. Klier and D. A. Cheresh in Cell 79, 1157-64 (1994).

Pro-angiogenic activity, preferably mediated by integrins, of the cyclic peptides according to the invention preferably leads to a reduction of wrinkle on skin, to darkening of hair and/or acceleration of wound healing. Preferably, the cyclic peptides may also be used to treat dermatological conditions such as hyperkeratosis, photo-aging, burns, donor site wounds from skin transplants, ulcers (cutaneous, decubitus, venous stasis and diabetic), psoriasis, skin rashes and sunburn photoreactive processes.

Induction of hair growth by modulating vascular endothelial growth factor (VEGF) and/or vascular endothelial growth factor receptor (VEGFR) has been described in WO 2003/072049 by Waugh and Dake. Since integrins interact with VEGF and/or VEGFR, cyclic peptides according to the invention can preferably used as modulators in this respect, thus inducing hair growth.

Due to their above/below described valuable properties, the cyclic peptides according to the invention and especially the cyclic peptides according to formula I, Ia, Ib, Ic, Id and/or Ie, can preferably also be employed as antimicrobial substances. The effectiveness of the antimicrobial activity can be demonstrated by the method described by P. Valentin-Weigund et al., in Infection and Immunity, 2851-2855 (1988).

The compounds therefore have the property of inhibiting the binding of natural or synthetic ligands to integrins, especially the integrins $a_V\beta_3$, $a_V\beta_5$ and $a_{IIb}\beta_3$, but also of $a_V\beta_1$, $a_V\beta_6$ and $a_V\beta_8$.

Moreover, in the compounds according to formula I, Ia, Ib, Ic, Id and/or Ie, the preferred α-N-alkylation or α-C-alkylation of one or more amino acids, preferably the Y-amino acid, brings about metabolic stabilization and increased fat-solubility. Through the reduction in possible hydrogen bridges, since N-alkyl, for example, cannot be an H donor for C=O, the capacity to penetrate membranes is improved, so that it is possible to obtain increased oral absorbability; moreover, increased plasma protein binding may occur. The α-N-alkylation or α-C-alkylation of one or more amino acids, preferably the Y-amino acid unit, increases the inhibitory potency of the compounds and raises the selectivity of the inhibition in respect of specific integrins. The selectivity can be influenced in particular by the N-alkyl groups.

It is believed that the advantageous property profile of the cyclic peptides according to the invention and especially of the cyclic peptides according to formula I, Ia, Ib, Ic, Id and/or Ie for all uses according to the invention is attributed at least to a significant part to the above discussed integrin modulating activity of said compounds.

Accordingly, the instant invention more preferably relates to:

A composition, preferably a non-therapeutic composition, as described above/below, wherein said cyclic peptide is selected from the group consisting of the cyclic peptides according to formula I, Ia, Ib, Ic, Id and/or Ie, more preferably selected from consisting of the cyclic peptides according to formula Ia, Ib, Ic and/or Id, even more preferably selected from the group consisting of the cyclic peptides according to formula Ib, Ic and/or Ie, and especially preferred selected from the group consisting of the cyclic peptides according to formula Ic.

A composition, preferably a non-therapeutic composition, as described above/below, wherein said one or more cyclic peptides comprise Cyclo-(Arg-Gly-Asp-DPhe-Acha), and/or a salt or solvate thereof.

A composition, preferably a composition for topical use, comprising
i) one or more cyclic peptides as described above/below, preferably one or more cyclic peptides selected from the group consisting of the cyclic peptides according to formula I, Ia, Ib, Ic, Id and/or Ie, more preferably selected from consisting of the cyclic peptides according to formula Ia, Ib, Ic and/or Id, even more preferably selected from the group consisting of the cyclic peptides according to formula Ib, Ic and/or Ie, and especially preferred selected from the group consisting of the cyclic peptides according to formula I,
ii) one or more skin-tolerated vehicles, and optionally
iii) one or more further active compounds having a skin-care, hair-care and/or inflammation-inhibiting action, preferably having a skin-care and/or inflammation-inhibiting action.

A composition, preferably a composition for topical use, comprising
i) one or more cyclic peptides as described above/below, preferably one or more cyclic peptides selected from the group consisting of the cyclic peptides according to formula I, Ia, Ib, Ic, Id and/or Ie, more preferably selected from consisting of the cyclic peptides according to formula Ia, Ib, Ic and/or Id, even more preferably selected from the group consisting of the cyclic peptides according to formula Ib, Ic and/or Ie, and especially preferred selected from the group consisting of the cyclic peptides according to formula Ic,
ii) one or more skin-tolerated vehicles, and optionally
iii) one or more further active compounds having a skin-care, hair-care and/or inflammation-inhibiting action, preferably having a skin-care and/or inflammation-inhibiting action.

A composition, preferably a composition for topical use, comprising
i) the Cyclo-(Arg-Gly-Asp-DPhe-Acha), and/or a salt or solvate thereof,
ii) one or more skin-tolerated vehicles, and optionally
iii) one or more further active compounds having a skin-care, hair-care and/or inflammation-inhibiting action, preferably having a skin-care and/or inflammation-inhibiting action.

A composition as described above/below, wherein said one or more cyclic peptides are contained in said composition in an amount of 0.00001 percent by weight to 10 percent by weight, preferably in an amount of 0.001 percent by weight to 10 percent by weight, more preferably in an amount of 0.1 percent by weight to 10 percent by weight, even more preferably 0.001 percent by weight to 5 percent per weight and especially 0.1 percent by weight to 5 percent by weight.

A composition comprising one or more cyclic peptides as described above/below, and at least one further skin-care ingredient and at least one carrier which is suitable for topical applications.

Use of one or more cyclic peptides as described above/below for the manufacture of a composition, preferably a non-therapeutic composition and especially preferably a cosmetic composition or topical composition.

Use of one or more cyclic peptides as described above/below for the preparation of a composition which is suitable for the prophylaxis and/or treatment of skin diseases which are associated with defective keratinisation relating to differentiation and cell proliferation, in particular for the treatment of acne vulgaris, acne comedonica, polymorphic acne, acne rosaceae, nodular acne, acne conglobata, age-related acne, acne occurring as a side effect, such as acne solaris, medicament-related acne or acne professionalis, for the treatment of other defects of keratinisation, in particular ichthyosis, ichthyosiform states, Darier's disease, keratosis palmoplantaris, leukoplakia, leukoplakiform states, skin and mucosal (buccal) eczema (lichen), for the treatment of other skin diseases which are associated with defective keratinisation and have an inflammatory and/or immunoallergic component, and in particular all forms of psoriasis relating to the skin, mucous membranes and finger- and toenails, and psoriatic rheumatism and skin atopy, such as eczema, or respiratory atopy, or also hypertrophy of the gums.

Use of a one or more cyclic peptides as described above/below for the care, preservation or improvement of the general state of the skin or hair.

Use of a one or more cyclic peptides as described above/below for the prophylaxis against or reduction of skin unevenness, such as wrinkles, fine lines, rough skin or large-pored skin.

Use of one or more cyclic peptides as described in one or more of the claims 1 to 7 for the prophylaxis against time- and/or light-induced ageing processes of the human skin or human hair, in particular for prophylaxis against dry skin, wrinkle formation and/or pigment defects, and/or for the reduction or prevention of the harmful effects of UV rays on the skin.

Preferably, the cyclic peptides according to the invention and the compositions containing them preferably appear to have a benefit in tissue regeneration. This is believed to be due to their ability to modulate and preferably stimulate the production of certain advantageous biomolecules, including, but not limited to, collagen I, fibronectin, collagen IV and/or hyaluronic acid, in skin cells.

Thus, the cyclic peptides according to the invention and the compositions containing them can preferably be used to improve the visible signs of ageing in human skin, including fine lines, wrinkles, enlarged pores, roughness, dryness, and other skin texture defects such as the stretchmarks (as caused by pregnancy, trauma or other influences) bags under the eyes, also called "puffy eyes" and dark (under eye) circles, both preferably caused by thinning of the skin, insufficient blood circulation and/or slack tissue, especially on repeated topical application.

Thus, further subjects of the instant invention preferably comprise:
A method and/or a composition for reducing the visible signs of ageing, preferably for reducing the visible signs of ageing of the skin and/or hair, in an animal, preferably the human animal comprising:
applying to the animal showing signs of ageing, preferably to the portion of the skin and/or hair showing signs of ageing, a composition comprising one or more cyclic peptides, more preferably a composition as described above/below comprising one or more cyclic peptides as described above/below, at least once a day for a period of time at least sufficient to provide a reduction of the visible signs of ageing, preferably the visible signs of ageing of the skin and/or hair. The period of time at least sufficient to provide the reduction of the visible signs of ageing generally is between one day and 12 months, preferably three days and six months, more preferably between two weeks and two months.

A method and/or a composition for reducing stretch marks of the skin, comprising:
applying to the skin, preferably at least to the portion of the skin showing stretchmarks, a composition comprising one or more cyclic peptides, more preferably a composition as described above/below comprising one or more cyclic peptides as described above/below, at least once a day for a period of time at least sufficient to provide a reduction of the visible signs of stretch marks. The period of time at least sufficient to provide the reduction of the visible signs of stretch marks generally is between one day and 12 months, preferably three days and six months, more preferably between two weeks and two months.

A method and/or a composition for reducing stretch marks of the skin, comprising:
applying to the skin, preferably at least to the portion of the skin showing stretch marks, a composition comprising one or more cyclic peptides, more preferably a composition as described above/below comprising one or more cyclic peptides as described above/below, at least once a day for a period of time at least sufficient to provide a reduction of the visible signs of stretch marks. The period of time at least sufficient to provide the reduction of the visible signs of stretch marks generally is between one day and 12 months, preferably three days and six months, more preferably between two weeks and two months.

A method and/or a composition for reducing dark circles under the eyes, comprising:
applying to the skin, preferably at least to the portion of the skin showing the dark circles, a composition comprising one or more cyclic peptides, more preferably a composition as described above/below comprising one or more cyclic peptides as described above/below, at least once a day for a period of time at least sufficient to provide a reduction of the dark circles of the portion of human skin. The period of time at least sufficient to provide the reduction of the dark circles generally is between one day and 12 months, preferably three days and six months, more preferably between two weeks and two months.

One aspect of the present invention relates to the use of cyclic peptides for the protection of the skin against hair treatment agents, especially for the protection of the skin of the head against pigments, dyestuffs, dyes and/or colouring agents which are commonly used for colouring of the hair. During the treatment of the hair with cosmetic compositions the contact of the head treatment composition with the underlying skin is normally not completely avoidable. The contact of the head treatment composition with the underlying skin is especially disadvantageous in the case of hair colouring compositions, since the resulting colouration of the parts of the skin around the hair line and/or the roots of the hair is generally regarded as unesthetic and thus undesirous.

Thus, it is desirous to protect the skin from the negative effects of the hair treatment compositions. It is known in the art to use a variety compositions, such as emulsions, or other agents, such as vaseline, to achieve such a protection of the skin. However, the compositions and agents of prior art show only limited efficacy and/or have two be removed after the application of the head treatment composition. For example, vaseline is hard to remove from the skin and/or a hair due to its unsolubility in water. For a sufficient removal thereof, the use of strong detergents and/or organic solvents can become necessary, thereby affecting the intended result of the application of the hair treatment composition and/or having negative effect on the condition of the skin and/or hair.

According to the instant invention, the cyclic peptides as defined above/below can be advantageously applied to protect the skin against hair treatment agents and especially to protect the skin of the head against adverse effects of pigments, dyestuffs, dyes and/or colouring agents, or hair colouring compositions in general.

Thus, a further subject of the instant invention is:
The use of one or more of the cyclic peptides as described above/below for the protection of the skin against hair treatment agents, especially for the protection of the skin of the head against pigments, dyestuffs, dyes and/or colouring agents, or hair colouring compositions in general.

The use of one or more of the cyclic peptides as described above/below in a composition for the protection of the skin against hair treatment agents, especially for the protection of the skin of the head against pigments, dyestuffs, dyes and/or colouring agents, or hair colouring compositions in general.

The use of one or more of the cyclic peptides as described above/below for producing a preparation to protect the skin against hair-treatment compositions, preferably compositions which can dye, tint, shape, harden, condition, soften, repair or style hair, and especially compositions which can colour or tint the hair.

The use of one or more of the cyclic peptides as described above/below for the simultaneous protection of the skin against hair-treatment compositions and additionally for the care of the skin.

The compositions of the invention generally comprise one or more cyclic peptides, preferably one or more cyclic peptides as described herein, and one or more vehicle or carrier, preferably one or more cosmetically acceptable vehicle or carrier. The one or more vehicles or carriers may be independently selected from the group of hydrophobic and hydrophilic vehicles or carriers. Suitable, hydrophobic vehicles or carriers include, for example, waxy non-ionic substances, preferably waxy non-ionic substances commonly used in cosmetics, including, but not limited to esters and ethers of fatty alcohols and of fatty acids, with carbon chain length from C4 to C22, preferably from C8 to C18, and most preferably from C-12 to C18- Examples of a fatty hydrophobic carriers or vehicles are preferably selected from the group consisting of isopropyl myristate, isopropyl palmitate, octyl palmitate, isopropyl lanolate, acetylated lanolin alcohol, the benzoate of C12-C15 alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate, and isopropyl isostearate, and the like. Examples of hydrophilic carrier or vehicles, especially for solutions, are preferably selected from the group consisting of glycols and alkoxylated glycols, preferably glycols and alkoxylated glycols commonly used in cosmetics, including, but not limited to, ethylene glycol, diethylene glycol, triethylene glycol, propylene glycol, dipropylene glycol, and the like.

The compositions according to the invention, especially the cosmetic compositions according to the invention may be formulated as creams, lotions, serums, sprays, sticks and other forms known to those skilled in the art. Creams and lotions are the currently preferred product forms.

Preferably, the concentration of peptides in the cosmetically acceptable vehicle may range from 1 ppb to 10,000 ppm, preferably from 10 ppb to 1,000 ppm, more preferably from 100 ppb to 100 ppm, and most preferably from 1 ppm to 100 ppm.

Preferably, cosmetic compositions can typically comprise the carrier solution described above at levels between about 0.01% and about 90% by weight, preferably between about 0.1% and about 50%, more preferably between about 0.1% and about 20%, and more preferred still between about 1% and about 10% by weight.

Preferably, the concentration of cyclic peptides in the composition for application, preferably application to the skin and/or hair, may range from 1 ppb to 10,000 ppm, preferably from 10 ppb to 1,000 ppm, more preferably from 100 ppb to 100 ppm, even more preferably from 0.5 ppm to 150 ppm and most preferably 1 ppm to 100 ppm, for example about 0.5 ppm, about 1 ppm, about 1.5 ppm, about 5 ppm, about 10 ppm, about 25 ppm, about 50 ppm, about 75 ppm, about 100 ppm or about 125 ppm.

If applicable, ppb and ppm preferably are to be regarded to be based on the respective weights, such as of the weight of the respective components (e.g. cyclic peptide, vehicle) and/or the weight of the respective component and the total weight of the composition. Accordingly, 1 ppm is preferably regarded as 1 mg/kg or $10^{-4}$% by weight.

Optionally, the compositions according to the invention may optionally comprise additional active and inactive ingredients other than the cyclic peptides according to the invention, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 and/or or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. In addition to the foregoing, the personal care products of the invention may contain any other compound for the treatment of skin disorders.

The invention also provides a method for ameliorating and/or preventing signs of human skin photo- and intrinsic aging comprising topically applying the cosmetic compositions of the invention. The cosmetic compositions of the invention are preferably applied to affected skin areas once or twice daily for as long as is necessary to achieve desired anti-aging results.

The present invention furthermore relates to compositions, preferably non-therapeutic compositions, comprising one or more of the cyclic peptides according to the invention, especially one or more of the cyclic peptides according to formulae I, Ia, Ib, Ic, Id and/or Ie, and at least one further skin-care ingredient and at least one carrier which is suitable for topical applications, and to the use of the above-mentioned compounds for the care, preservation or improvement of the general state of the skin or hair.

Uses which are preferred in accordance with the invention
i) of the cyclic peptides according to the invention, especially the cyclic peptides according to formulae I, Ia, Ib, Ic, Id and/or Ie, and/or
ii) of compositions, preferably non-therapeutic compositions, topical compositions and/or cosmetic compositions comprising one or more cyclic peptides according to the invention, especially one or more of the cyclic peptides according to formulae I, Ia, Ib, Ic, Id and/or Ie,
are, in particular, the use for prophylaxis against time- and/or light-induced ageing processes of the human skin or human hair, in particular for prophylaxis against dry skin, wrinkle formation and/or pigment defects, and/or for the reduction or prevention of the harmful effects of UV rays on the skin, and for prophylaxis against or reduction of skin unevenness, such as wrinkles, fine lines, rough skin or large-pored skin.

Uses which are preferred in accordance with the invention
i) of the cyclic peptides according to the invention, especially the cyclic peptides according to formulae I, Ia, Ib, Ic, Id and/or Ie, and/or
ii) of compositions, preferably non-therapeutic compositions, topical compositions and/or cosmetic compositions comprising one or more cyclic peptides according to the invention, especially one or more of the cyclic peptides according to formulae I, Ia, Ib, Ic, Id and/or Ie,
are furthermore the use for the prophylaxis and/or prevention of premature skin ageing, in particular for the prophylaxis and/or prevention of light- or ageing-induced wrinkling of the skin, for the reduction of pigmentation and keratosis actinica, and for the prophylaxis and/or treatment of all diseases which are associated with normal skin ageing or light-induced ageing of the skin, and for the prophylaxis and/or treatment of skin diseases which are associated with defective keratinisation relating to differentiation and cell proliferation, in particular for the treatment of acne vulgaris, acne comedonica, polymorphic acne, acne rosaceae, nodular acne, acne conglobata, age-related acne, acne occurring as a side effect, such as acne solaris, medicament-related acne or acne professionalis, for the treatment of other defects of keratinisation, in particular ichthyosis, ichthyosiform states, Darier's disease, keratosis palmoplantaris, leukoplakia, leukoplakiform states, skin and mucosal (buccal) eczema (lichen), for the treatment of other skin diseases which are associated with defective keratinisation and have an inflammatory and/or immunoallergic component, and in particular all forms of psoriasis relating to the skin, mucous membranes and finger- and toenails, and psoriatic rheumatism and skin atopy, such as eczema, or respiratory atopy, or also hypertrophy of the gums, and for the prophylaxis and/or treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare.

The present invention also relates to the use of one or more of the cyclic peptides according to the invention, especially one or more of the cyclic peptides according to formulae I, Ia, Ib, Ic, Id and/or Ie, for the preparation of compositions which are suitable for the above-mentioned uses.

The cyclic peptides for use according to the invention are preferably applied and/or formulated in the presence of surface active or amphiphilic compounds, preferably surface active or amphiphilic compounds that are capable of forming self assembled structures, such as vesicles or sacs. Such vesicles or sacs are generally produced from amphiphilic compounds (compounds having both a hydrophobic portion and a hydrophilic (polar) portion), with such vesicles or sacs being most commonly produced from lipids, in particular, phospholipids. When the vesicles or sacs are produced from lipids or lipidlike materials they are most often referred to as liposomes. Additionally, such lipids or lipidlike materials can form nanosomes and/or nanoemulsions.

Advantagously, liposomes, nanosomes and/or nanoemulsions, preferably liposomes and/or nanosomes and especially liposomes, can be formed in a manner such as to encapsulate a material, including e.g. one or more of the cyclic peptides according to the invention, in the interior of said liposome, nanosome and/or nanoemulsion. Thus, for example, such liposomes have been used to encapsulate biologically active materials; for example, a therapeutic drug. According to this invention, liposomes, nanosomes and/or nanoemulsions can advantageously be applied to interact with the cyclic ceptides as described herein. For example, cyclic ceptides as described herein can be encapsulated or entrapped into liposomes, nanosomes and/or nanoemulsions, preferably liposomes and/or nanosomes and especially liposomes; or otherwise associated to them.

Liposomes, nanosomes and/or nanoemulsions may be prepared from a wide variety of lipids, including phospholipids, glycol lipids, and as representative examples there may be mentioned lecithin, spingomyelin, dipalmitoyl lecithin, distearoylphosphatidylcholine, etc. The amphiphilic lipids employed for producing liposomes generally have a hydrophilic group, such as a phosphoryl, carboxylic, sulfonyl, or amino group, and a hydrophobic group, such as saturated and unsaturated aliphatic hydrocarbons, and aliphatic hydrocarbon groups substituted by one or more aromatic or cycloaliphatic groups. However, the compounds for producing liposomes, nanosomes and/or nanoemulsions are generally known in the art, and no further details in this respect are deemed necessary for a complete understanding of the present invention. The wall forming compounds for producing the liposomes may further optionally include a steroid component such as cholesterol, cholestanol, and the like.

Phosphatidylcholine, a purified fraction of lecithin, can be advantageously used for preparation of highly dispersed systems. These systems preferably comprise nanoemulsions and/or liposomes and are preferably capable of absorbing or encapsulating a great variety of active substances through their membrane lipids. By means of their outstanding penetrative qualities, these membranes are capable of transferring said active substances quickly and effectively into the skin and/or hair. For example, this preferably results in the fusion of the lipids, preferable skin-identical lipids, of said nanoemulsions and/or liposomes with the membrane lipids of the skin.

Since the liposomal and the nanosomal systems' structures differ, they preferably make it possible to load different actives into each. Nonetheless, the transport properties of both systems are preferably very similar. In some cases, a fine dispersion and size can enhance their function.

Liposomes:

Liposomes are preferably small, sphere-like vesicles formed by amphiphilic lipids enclosing a hydrophilic core. They are typical carrier vehicles that preferably embed actives into their bilayer membrane and/or hydrophilic core. The positioning of the active depends on its hydrophilic properties. As they are skin related, Liposomes preferably improve the penetration of actives into cosmetically relevant areas, such as various layers of the epidermis and/or into the hair. Thus, the desired fixation of actives, e.g. in the upper layer of the epidermis, is preferably supported. Liposomes preferably show a beneficial dispersity within the skin and create active depots in the subcorneous.

Nanoemulsions:

Nanoemulsions are preferably characterised by a lipophilic core which is demarcated by a lipid monolyer, preferably a lecithin monolayer, from the external water phase. These nanoemulsions are preferably suitable as vehicles for lipophilic components. Similar to the liposomes, they preferably support penetration of actives into the skin. By penetrating the skin in this way, the active's bioavailability and efficacy, for instance, can be optimised. Stable, low viscosity and therefore sprayable emulsions can be developed which preferably leave no sticky and/or oily residues on the skin. Nanoemulsions, especially nanoemulsions based on lecithin, preferably show excellent disparity inside the skin and/or create active depots in the subcorneous.

The pH value of the liposomes, nanosomes and/or nanoemulsions largely depends on the selection of the respective lipids and/or other ingredients. If desired, the pH value can be adapted by the additions of bases, acids and/or buffers. Generally, for use according to the invention, a pH value that is acceptable to the skin and/or hair is preferred. Thus, a pH in the range of 4.5 to 8.5, preferably 5 to 8, and especially 5.5. to 7.5, e.g. a pH of about 5.5, about 6, about 7 or about 7.5 and especially about 6, is generally preferred.

Thus, a preferred subject of the instant invention relates to a composition, preferably a liposome, nanosome and/or nanoemulsion composition, comprising i) one or more cyclic peptides as described above/below, preferably one or more cyclic peptides selected from the group consisting of the cyclic peptides according to formula I, Ia, Ib, Ic, Id and/or Ie, more preferably selected from consisting of the cyclic peptides according to formula Ia, Ib, Ic and/or Id, even more preferably selected from the group consisting of the cyclic peptides according to formula Ib, Ic and/or Ie, and especially preferred selected from the group consisting of the cyclic peptides according to formula Ic, ii) one or more lipids, iii) one or more physiologically acceptable solvents, and optionally one or more further active compounds having a skin-care, hair-care and/or inflammation-inhibiting action.

Thus, a preferred subject of the instant invention relates to a composition, preferably a liposome, nanosome and/or nanoemulsion composition, comprising i) 0.00001 to 20% by weight, preferably 0.0001 to 10% by weight and especially 0.001 to 1% by weight, of one or more cyclic peptides as described above/below, preferably one or more cyclic peptides selected from the group consisting of the cyclic peptides according to formula I, Ia, Ib, Ic, Id and/or Ie, more preferably selected from consisting of the cyclic peptides according to formula Ia, Ib, Ic and/or Id, even more preferably selected from the group consisting of the cyclic peptides according to formula Ib, Ic and/or Ie, and especially preferred selected from the group consisting of the cyclic peptides according to formula Ic, ii) 0.001 to 50% by weight, preferably 0.01 to 20% by weight and especially 0.01 to 10% by weight, of one or more lipids, iii) 50 to 99.999% by weight, preferably 60 to 99.99% by weight and especially 70 to 99% by weight, of one or more physiologically acceptable solvents, and optionally iv) 0.00001 to 30% by weight, preferably 0.0001 to 20% by weight and especially 0.001 to 10% by weight, of one or more further ingredients, selected from the group consisting of α) further active compounds having a skin-care, hair-care and/or inflammation-inhibiting action, and β) further cosmetically acceptable excipients.

In this respect, the one or more cyclic peptides preferably cyclic peptides Cyclo-(Arg-Gly-Asp-DPhe-Acha), and/or a salt or solvate thereof.

In this respect, the one or more lipids preferably comprise one or more of the following:
a) phospholipids,
b) glycosphingolipids,
c) lecithin,
d) spingomyelin,
e) dipalmitoyl lecithin,
f) distearoylphosphatidylcholine,
g) phosphatidylcholine,
h) saturated phosphatidylcholine,
i) unsaturated phosphatidylcholine,
j) polystyrene,
k) octyldodecanol, optionally in combination with Silica,
l) octyldodecanol, optionally in combination with phospholipids, cholesterol and/or glycospingolipids,
and the salts thereof, preferably the alkali salts and/or ammonium salts thereof.

In this respect, the one or more lipids are especially preferably selected from the group consisting of:
c) lecithin,
d) spingomyelin,
e) dipalmitoyl lecithin,
f) distearoylphosphatidylcholine,
g) phosphatidylcholine,
h) saturated phosphatidylcholine,
i) unsaturated phosphatidylcholine,
j) and mixtures thereof,
and the salts thereof, preferably the alkali salts and/or ammonium salts thereof.

In this respect, the one or more physiologically acceptable solvents are especially preferably selected from the group consisting of:
a) water,
b) alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products,
c) alcohols having 2 to 6 and especially 2 to carbon atoms, for example ethanol, isopropanol, 1,2-propanediol or glycerol, preferably ethanol or isopropanol, and/or
d) alcohol (ethanol), glycerin, propylene glycol (1,2-propylene glycol), butylene glycol (1,4-butanediol), pentylene glycol, pentylene glycol in combination with ethanol, sorbitol, preferably ethanol, glycerin, 1,2-propylene glycol, 1,4-butanediol, pentylene glycol, sorbitol, and mixtures thereof, more preferably ethanol and pentylene glycol, and mixtures thereof, and especially ethanol.

In this respect, one or more physiologically acceptable solvents preferably comprise water, preferably in an amount in the range between 10 to 99.9 by weight, more preferably 20 to 99% by weight, even more preferably 30 to 95% by weight, even more preferably 50 to 90% by weight and especially 60 to 80% by weight, for example about 65% by weight, about 70% by weight, about 75% by weight, about 80% by weight or about 85% by weight, based on the total weight of said composition.

In this respect, one or more physiologically acceptable solvents preferably comprise an alcohol, preferably an alcohol having 2 to 5 carbon atoms, more preferably selected from ethanol, isopropanol, glycerin, 1,2-propylene glycol, 1,4-butanediol, pentylene glycol, sorbitol, and mixtures thereof, more preferably ethanol and pentylene glycol, and mixtures thereof, and especially ethanol ethanol, preferably in an amount in the range between 0.1 to 50% by weight, more preferably 1 to 40% by weight, even more preferably 5 to 30% by weight, even more preferably 10 to 25% by weight and especially 15 to 20% by weight, for example about 8% by weight, about 12% by weight, about 15% by weight, about 17% by weight or about 20% by weight, based on the total weight of said composition. Said alcohols, preferably in said amounts, preferably have a preserving effect on the compositions. There inclusion, preferably in the given amounts, may help to omit or reduce the need to add preservatives as described herein to said compositions.

In this respect, the further active compounds having a skin-care, hair-care and/or inflammation-inhibiting action (a) preferably comprise Ectoin, preferably in an amount in the range of 0.1 to 30% by weight, more preferably 1 to 20% by weight, even more preferably 3 to 15% by weight and especially about 5% by weight, about 8% by weight, about 10% by weight or about 12% by weight, based on the total weight of said composition.

In this respect, the further cosmetically acceptable excipients (β) include compounds that are regarded as preservatives. Examples of such compounds that are suitable for use in the compositions according to the invention are one or more compounds, preferably selected from the group consisting of:
a) Phenoxyethanol, Methylparaben, Ethylparaben, Propylparaben and/or Butylparaben, and combinations thereof;
b) Alcohol, Phenoxyethanol, Methylparaben, Butylparaben, Ethylparaben, Isopropylparaben, Propylparaben, and combinations thereof;
c) Chlorphenesin;
d) Benzoic acid
e) Dehydroacetic acid, Benzoic acid and/or Phenoxyethanol, and combinations thereof.

If the further cosmetically acceptable excipients (β) include compounds that are regarded as preservatives, preferably preservatives as described above, they preferably contain an amount thereof in the range of 0.01 to 5% by weight, more preferably 0.05 to 3% by weight, even more preferably 0.1 to 2% by weight and especially 0.2 to 1.5% by weight.

Thus, the compositions described herein, especially the lipid containing compositions described herein optionally comprise, preferably based on the total weight of the composition, one or more compounds selected from the group consisting of:
f) Phenoxyethanol, Methylparaben, Ethylparaben, Propylparaben and/or Butylparaben, and combinations thereof;
g) Alcohol, Phenoxyethanol, Methylparaben, Butylparaben, Ethylparaben, Isopropylparaben, Propylparaben, and combinations thereof;
h) Chlorphenesin;
i) Benzoic acid
Dehydroacetic acid, Benzoic acid and/or Phenoxyethanol, and combinations thereof, preferably in a total amount in the range of 0.01 to 5% by weight, more preferably 0.05 to 3% by weight, even more preferably 0.1 to 2% by weight and especially 0.2 to 1.5% by weight.

Thus, a preferred subject of the instant invention relates to a composition, preferably a liposome, nanosome and/or nanoemulsion composition, comprising
i) 0.00001 to 20% by weight, preferably 0.0001 to 10% by weight and especially 0.001 to 1% by weight, of Cyclo-(Arg-Gly-Asp-DPhe-Acha), and/or a salt or solvate thereof,
ii) i0.001 to 50% by weight, preferably 0.01 to 20% by weight and especially 0.01 to 10% by weight, of one or more lipids, selected from the group consisting of lecithin, spingomyelin, dipalmitoyl lecithin, distearoylphosphatidylcholine, phosphatidylcholine, saturated phosphatidylcholine and unsaturated phosphatidylcholine, and especially from the group consisting of phosphatidylcholine, saturated phosphatidylcholine and unsaturated phosphatidylcholine, and the mixtures and salts thereof, iii) 50 to 99.999% by weight, preferably 60 to 99.99% by weight and especially 70 to 99% by weight, of one or more physiologically acceptable solvents preferably selected from water, and optionally iv) 0.00001 to 30% by weight, preferably 0.0001 to 20% by weight and especially 0.001 to 10% by weight, of one or more further ingredients, selected from the group consisting of
  α) further active compounds having a skin-care, hair-care and/or inflammation-inhibiting action, and
  β) further cosmetically acceptable excipients.

Preferably, in the compositions described above and/or below, more preferably the liposome, nanosome and/or nanoemulsion compositions as described above and/or below and especially in the liposome and/or nanosome compositions as described above and/or below, at least a part of the one or more cyclic peptides is entrapped into liposomes, nanosomes and/or nanoemulsion particles, more preferably liposomes and/or nanosomes and especially liposomes, that are formed by the one or more lipids contained in said composition. Typically, the part of the one or more cyclic peptides entrapped into said liposomes, nanosomes and/or nanoemulsion particles is preferably in the range between 1% and 99.99%, more preferably between 10% and 99.9%, even more preferably between 20% and 99% and especially between 50% and 95%, based on the total amount of said one or more cyclic peptides contained in said composition.

In liposomal compositions as described herein, the particle size of the liposomes preferably lies in the range of 1 to 1000 nanometers (nm), more preferably 5 to 500 nm, even more preferably 10 to 400 nm and especially in the range of 50 to 200 nm.

In liposomal compositions as described herein, the mean particle size, preferably the mean particle size D50 and/or D90, of the liposomes preferably lies in the range of 1 to 1000 nanometers (nm), more preferably 5 to 500 nm, even more preferably 10 to 400 nm and especially in the range of 50 to 200 nm.

In liposomal compositions as described herein, the mean particle size, is especially preferably 90 nm+/−80 nm and even more preferably 70 nm+/−50 nm, preferably using Photon Correlation Spectroscopiy (PCS), preferably at Angle 90°, and preferably using a Helium-Neon laser.

Preferably, particle sizes and/or mean particle sizes are preferably determined at Room temperature (20° C.).

Thus, an especially preferred subject of the instant invention relates to a composition, preferably a liposome, nanosome and/or nanoemulsion and especially a liposome or liposomal composition, comprising i) 0.001 to 10% by weight, preferably 0.001 to 5% by weight and especially 0.005 to 1% by weight, for example about 0.005% by weight, about 0.01% % by weight, about 0.05% by weight or about 0.5% by weight, of Cyclo-(Arg-Gly-Asp-DPhe-Acha), and/or a salt or solvate thereof, ii) 0.1 to 20% by weight, preferably 1 to 15% by weight and especially 2 to 10% by weight, for example about 3% by weight, about 5% by weight, about 7% by weight or about 10% by weight, of one or more lipids, selected from the group consisting of lecithin, phosphatidylcholine, saturated phosphatidylcholine and unsaturated phosphatidylcholine and mixtures and salts thereof, and especially from the group consisting of phosphatidylcholine, saturated phosphatidylcholine and unsaturated phosphatidylcholine and mixtures and salts thereof, iii) 50 to 95% by weight, preferably 60 to 90% by weight and especially 70 to 85% by weight, of water, iv) 0 to 40% by weight, preferably 5 to 30% by weight, and especially 10 to 20% by weight, of one or more physiologically acceptable solvents other than water, preferably selected from alcohols having 2 to 4 carbon atoms and more preferably selected from ethanol and isopropanol, v) 0 to 25% by weight, preferably 1 to 15% by weight, and especially 2 to 10% by weight, of Ectoin and/or a salt thereof, and optionally vi) 0 to 25% by weight, preferably 0.1 to 15% by weight, and especially 0.5 to 10% by weight, of one or more further ingredients, selected from the group consisting of
  α) further active compounds having a skin-care, hair-care and/or inflammation-inhibiting action other than ectoin, and
  β) further cosmetically acceptable excipients.

Thus, an especially preferred subject of the instant invention relates to a composition, preferably a liposome, nanosome and/or nanoemulsion and especially a liposome or liposomal composition, comprising or essentially consisting of i) 0.001 to 0.1% by weight, preferably 0.005 to 0.05% by weight and especially about 0.01% by weight, of Cyclo-(Arg-Gly-Asp-DPhe-Acha), and/or a salt or solvate thereof, ii) 1 to 10% by weight, preferably 3 to 8% by weight and especially about 5% by weight, of one or more lipids, selected from the group consisting of lecithin, phosphatidylcholine, saturated phosphatidylcholine and unsaturated phosphatidylcholine and mixtures and salts thereof, and especially from the group consisting of phosphatidylcholine, saturated phosphatidylcholine and unsaturated phosphatidylcholine and mixtures and salts thereof, iii) 5 to 25% by weight, preferably 10 to 20% by weight, and especially about 15, about 17 or about 20% by weight, of one or more physiologically acceptable solvents other than water, selected from ethanol and isopropanol, iv) 0 to 10% by weight, preferably 0.5 to 10% by weight, and especially 0 or about 5% by weight, of ectoin and/or a salt thereof, preferably ectoin, and optionally v) 0 to 10% by weight, preferably 0.1 to 5% by weight, and especially 0.5 to 5% by weight, of one or more further ingredients, selected from the group consisting of
  α) further active compounds having a skin-care, hair-care and/or inflammation-inhibiting action other than ectoin, and
  β) further cosmetically acceptable excipients, preferably further cosmetically acceptable excipients as described herein, preservatives, preferably preservatives as described herein, and acids, bases or buffers, preferably acids, bases or buffers as described herein.

Thus, an especially preferred subject of the instant invention relates to a composition, preferably a liposome, nanosome and/or nanoemulsion and especially a liposome or liposomal composition, essentially consisting of i) about 0.01% by weight Cyclo-(Arg-Gly-Asp-DPhe-Acha), and/or a salt or solvate thereof, preferably Cyclo-(Arg-Gly-Asp-DPhe-Acha), ii) about 5% by weight, of one or more lipids, selected from the group consisting of lecithin, phosphatidylcholine, saturated phosphatidylcholine and especially from the group consisting of phosphatidylcholine, saturated phosphatidylcholine and unsaturated phosphatidylcholine and mixtures thereof,
iii) 15 to 20% by weight and especially about 17% by weight of ethanol and/or isopropanol,
iv) 5 to 10% by weight about 5% by weight, of ectoin and/or a salt thereof, preferably ectoin,
v) optionally 0 to 10% by weight, preferably 0.1 to 5% by weight, and especially 0.5 to 5% by weight, of one or more further ingredients, selected from the group consisting of
α) further active compounds having a skin-care, hair-care and/or inflammation-inhibiting action other than ectoin, and
β) further cosmetically acceptable excipients, preferably further cosmetically acceptable excipients as described herein, preservatives, preferably preservatives as described herein, and acids, bases or buffers, preferably acids, bases or buffers as described herein,
vi) and water ad 100% weight to the total weight of the composition.

Thus, an especially preferred subject of the instant invention relates to a composition, preferably a liposome, nanosome and/or nanoemulsion and especially a liposome or liposomal composition, essentially consisting of
i) about 0.01% by weight Cyclo-(Arg-Gly-Asp-DPhe-Acha), and/or a salt or solvate thereof, preferably Cyclo-(Arg-Gly-Asp-DPhe-Acha),
ii) about 5% by weight, of one or more lipids, selected from the group consisting of lecithin, phosphatidylcholine, saturated phosphatidylcholine and especially from the group consisting of phosphatidylcholine, saturated phosphatidylcholine and unsaturated phosphatidylcholine and mixtures thereof,
iii) 15 to 20% by weight and especially about 17% by weight of ethanol and/or isopropanol, preferably ethanol,
iv) optionally 0 to 10% by weight, preferably 0.1 to 5% by weight, and especially 0.5 to 5% by weight, of one or more further ingredients other than ection, selected from the group consisting of
α) further active compounds having a skin-care, hair-care and/or inflammation-inhibiting action other than ectoin, and
β) further cosmetically acceptable excipients, preferably further cosmetically acceptable excipients as described herein, preservatives, preferably preservatives as described herein, and acids, bases or buffers, preferably acids, bases or buffers as described herein,
v) and water ad 100% by weight to the total weight of the composition.

The liposomes, nanosomes and/or nanoemulsions may be produced by procedures generally available in the art. For example, the compositions of the invention can be produced in accordance with any method for the preparation of liposome suspensions known to the person skilled in the art, for instance those in the book "Liposomes—a practical approach" published by R. C. New (Oxford University Press, 1990). Those compositions of the invention which contain alcohol can for example be produced by dissolving the phospholipids in alcohol, then adding any-other alcohol-soluble actives and stirring until these have dissolved. The resulting lipid solution is slowly added to water in which any other actives have been dissolved, and the mixture is then stirred. The liposomes which develop spontaneously are then reduced in size by applying energy supply, e.g. by stirring at high speed, highpressure filtration, ultrasound, extrusion or homogenisation, until the desired particle size is arrived at. If oxygen-sensitive phospholipids are being used, the production process can be carried out partially or entirely under protective gas or at reduced pressure.

The liposomes may be alternatively produced by a reverse phase evaporation technique wherein the compound or compounds used in producing liposomes are initially dissolved in an organic phase, followed by addition of an aqueous phase and forming of a homogeneous emulsion. After forming the emulsion, the organic solvent is evaporated to form a gel like material, and such gel may be converted to a liposome by agitation or dispersion in an aqueous media, such as water, water/alcohol mixtures and/or buffer solutions.

Additional procedures for producing liposomes are described, for example, in U.S. Pat. Nos. 4,241,046; 4,342,826 and PCT International Publication No. WO 80-01515, the disclosure of which is included into this application by reference in their entirety.

If a material is to be encapsulated in the liposome, such material may be encapsulated in the liposome by including the material in the aqueous solution in which the liposome is formed. Alternatively, the material may be encapsulated into a previously formed empty liposome (without material to be encapsulated) by the procedure described in U.S. application Ser. No. 659,200, filed on Sep. 13, 1984, the disclosure of which is included into this application by reference in their entirety.

The liposomes may also be produced by the procedures disclosed in U.S. Pat. No. 4,522,803, the disclosure of which is included into this application by reference in their entirety.

The material which is entrapped or encapsulated within the liposome (the material is within the aqueous compartment or within the membrane bilayer of the liposome) may be any one of a wide variety of materials, including the cyclic peptides as described herein, and/or ectoin, but also dyes, various cosmetic and/or therapeutic agents; and the like. Liposomes having a material entrapped therein are generally known in the art Further description of such liposomes is not deemed necessary for a complete understanding of the present invention.

Thus, an especially preferred subject of the invention, preferably comprising preferred compositions and their uses, is given below:
A composition, comprising
i) 0.0001 to 20% by weight, preferably 0.001 to 10% by weight and especially 0.01 to 1% by weight, of Cyclo-(Arg-Gly-Asp-DPhe-Acha), and/or a salt thereof, preferably Cyclo-(Arg-Gly-Asp-DPhe-Acha),
ii) 0.001 to 50% by weight, preferably 0.01 to 20% by weight and especially 0.01 to 10% by weight, of one or more lipids.

A composition, comprising
i) 0.0001 to 20% by weight, preferably 0.001 to 10% by weight and especially 0.01 to 1% by weight, of Cyclo-(Arg-Gly-Asp-DPhe-Acha), and/or a salt thereof, preferably Cyclo-(Arg-Gly-Asp-DPhe-Acha),
ii) 0.001 to 50% by weight, preferably 0.01 to 20% by weight and especially 0.01 to 10% by weight, of one or more lipids, and
iii) 30 to 99.9989% by weight, preferably 40 to 99.9% by weight, more preferably 50 to 98% by weight, even more preferably 60 to 95% by weight and especially 70 to 90% by weight, of water.

A composition, comprising
i) 0.0001 to 20% by weight, preferably 0.001 to 10% by weight and especially 0.01 to 1% by weight, of Cyclo- (Arg-Gly-Asp-DPhe-Acha), and/or a salt thereof, preferably Cyclo-(Arg-Gly-Asp-DPhe-Acha), ii) 0.001 to 50% by weight, preferably 0.01 to 20% by weight and especially 0.01 to 10% by weight, of one or more lipids, and iii) 10 to 99.9979% by weight, preferably 40 to 99.9% by weight, more preferably 50 to 98% by weight, even more preferably 60 to 95% by weight and especially 70 to 90% by weight, of water, iv) 0.001 to 20% by weight, preferably 0.01 to 15% by weight, more preferably 0.1 to 10% by weight, even more preferably 1 to 10% by weight and especially 2 to 5% by weight, of et least one further ingredient, preferably selected from ectoin, biotin, taurine, caffeine, taurine, purine, and/or derivatives thereof.

In the above and/or below compositions, the lipid is preferably selected from the group consisting of lecithin, spingomyelin, dipalmitoyl lecithin, distearoylphosphatidylcholine, phosphatidylcholine, phosphatidylcholine, saturated phosphatidylcholine and unsaturated phosphatidylcholine, more preferably selected from lecithin, phosphatidylcholine, saturated phosphatidylcholine and unsaturated phosphatidylcholine, and especially from the group consisting of phosphatidylcholine, saturated phosphatidylcholine and unsaturated phosphatidylcholine.

A composition, comprising i) 0.0001 to 20% by weight, preferably 0.001 to 10% by weight and especially 0.01 to 1% by weight, of Cyclo-(Arg-Gly-Asp-DPhe-Acha), and/or a salt thereof, preferably Cyclo-(Arg-Gly-Asp-DPhe-Acha), ii) 0.001 to 50% by weight, preferably 0.01 to 20% by weight and especially 0.01 to 10% by weight, of one or more lipids, selected from the group consisting of lecithin, spingomyelin, dipalmitoyl lecithin, distearoylphosphatidylcholine, phosphatidylcholine, saturated phosphatidylcholine and unsaturated phosphatidylcholine, more preferably selected from lecithin, phosphatidylcholine, saturated phosphatidylcholine and unsaturated phosphatidylcholine, and especially from the group consisting of phosphatidylcholine, saturated phosphatidylcholine and unsaturated phosphatidylcholine, and the mixtures and salts thereof, and iii) 30 to 99.9989% by weight, preferably 40 to 99.9% by weight, more preferably 50 to 98% by weight, even more preferably 60 to 95% by weight and especially 70 to 90% by weight, of water.

In the above and/or below described compositions, the one or more lipids preferably form liposomes, nanosomes and/or nanoemulsions, preferably liposomes. More preferably, at least 20%, more preferably at least 50% and especially at least 70%, but typically 100% or less, 95% or less, or 85% or less of the one or more lipids, based on the total amount of the one or more lipids that are present in said compositions, are present in the form of liposomes.

In the above and/or below described compositions, at least a part of the Cyclo-(Arg-Gly-Asp-DPhe-Acha) and/or the salts thereof is entrapped in said liposomes, nanosomes and/or nanoemulsions, preferably liposomes. Preferably, at least 5%, more preferably at least 10%, even more preferably at least 25%, even more preferably at least 50% and especially at least 75% of the Cyclo-(Arg-Gly-Asp-DPhe-Acha) and/or the salts thereof is entrapped in said liposomes, nanosomes and/or nanoemulsions, preferably liposomes, based on the total amount of Cyclo-(Arg-Gly-Asp-DPhe-Acha) and/or the salts thereof contained in said compositions, preferably determined at Room temperature (20° C.).

Preferably, the amount of the Cyclo-(Arg-Gly-Asp-DPhe-Acha) and/or the salts thereof entrapped in said liposomes, nanosomes and/or nanoemulsions, is preferably not less than 25%, more preferably not less than 50%, even more preferably not less than 75 percent and especially not less than 95%, based on the total amount of Cyclo-(Arg-Gly-Asp-DPhe-Acha) and/or the salts thereof contained in said compositions, preferably determined at Room temperature (20° C.).

Thus, the amount of the Cyclo-(Arg-Gly-Asp-DPhe-Acha) and/or the salts thereof entrapped in said liposomes, nanosomes and/or nanoemulsions, preferably lies in the range between 25 and 100%, more preferably in the range between 50 and 99.9%, even more preferably in the range between 60 and 99% and especially in the range between 70 and 95%, based on the total amount of Cyclo-(Arg-Gly-Asp-DPhe-Acha) and/or the salts thereof contained in said compositions, preferably determined at Room temperature (20° C.).

Thus, a further preferred subject of the instant invention is a liposomal composition, comprising i) 0.0001 to 20% by weight, preferably 0.001 to 10% by weight and especially 0.01 to 1% by weight, of Cyclo-(Arg-Gly-Asp-DPhe-Acha), and/or a salt thereof, preferably Cyclo-(Arg-Gly-Asp-DPhe-Acha), ii) 0.001 to 50% by weight, preferably 0.01 to 20% by weight and especially 0.01 to 10% by weight, of one or more lipids, selected from the group consisting of lecithin, phosphatidylcholine, saturated phosphatidylcholine and unsaturated phosphatidylcholine, and the mixtures and salts thereof, and iii) 30 to 99.9989% by weight, preferably 40 to 99.9% by weight, more preferably 50 to 98% by weight, even more preferably 60 to 95% by weight and especially 70 to 90% by weight, of water, iv) preferably wherein
  a) at least 20% of the one or more lipids, based on the total amount of the one or more lipids that are present in said composition, are present in the form of liposomes, and
  b) at least at least 20% of Cyclo-(Arg-Gly-Asp-DPhe-Acha), and/or a salt thereof, preferably Cyclo-(Arg-Gly-Asp-DPhe-Acha), based on the total amount of the Cyclo-(Arg-Gly-Asp-DPhe-Acha), and/or a salt thereof, preferably Cyclo-(Arg-Gly-Asp-DPhe-Acha) present in said composition, is entrapped in said liposomes.

Preferably, the amount or ratio of one or more compounds inside the liposomes, nanosomes and/or nanoemulsions, preferably liposomes, is determined at Room temperature (20° C.)

Composition, comprising i) 0.0001 to 20% by weight of Cyclo-(Arg-Gly-Asp-DPhe-Acha), and/or a salt thereof, ii) 0.001 to 50% by weight of one or more lipids, iii) 10 to 99.9979% by weight of water, and iv) 0.001 to 20% by weight of et least one further ingredient, selected from the group consisting of ectoin, biotin, taurine, caffeine, taurine, purine, and/or derivatives thereof.

In the compositions according to the invention as described above and/or below, the one or more lipids are preferably selected from the group consisting of lecithin, spingomyelin, dipalmitoyl lecithin, distearoylphosphatidylcholine, phosphatidylcholine, saturated phosphatidylcholine and unsaturated phosphatidylcholine, and mixtures and salts thereof.

A subject of the instant invention is a composition comprising
i) one or more cyclic peptides as described herein,
ii) one or more lipids,
iii) one or more physiologically acceptable solvents, and optionally
iv) one or more further active compounds having a skin-care, hair-care and/or inflammation-inhibiting action.

The above described compositions can be advantageously applied as such as topical compositions, cosmetic compositions, pharmaceutical compositions and/or medicinal products, preferably as topical, cosmetical or pharmaceutical compositions and especially as topical or cosmetic compositions.

Alternatively, they can advantageously be applied as an additive, an active ingredient and/or an active ingredient system in topical compositions, cosmetic compositions, pharmaceutical compositions and/or medicinal products, preferably in topical, cosmetical or pharmaceutical compositions and especially in topical or cosmetic compositions, preferably conventional topical compositions, cosmetic compositions, pharmaceutical compositions and/or medicinal products, preferably topical, cosmetical or pharmaceutical compositions and especially, topical or cosmetic compositions.

Accordingly, another preferred subject of the instant invention is the use of the compositions as described above and especially the liposomal compositions as described above, for the manufacture of one or more compositions, selected from the group consisting of compositions for topical use as described herein, topical compositions, cosmetic compositions, pharmaceutical compositions and medicinal products, preferably selected from the group consisting of topical, cosmetical or pharmaceutical compositions and especially preferably selected from topical or cosmetic compositions. For example, the compositions as described above, and especially the liposomal compositions as described above, can be advantageously added, as a further additive or ingredient, to already existing or other typical or conventional compositions, preferably selected from topical compositions, cosmetic compositions, pharmaceutical compositions and medicinal products, preferably topical, cosmetical or pharmaceutical compositions and especially topical or cosmetic compositions. In said use, the composition according to invention as described above and leisure below are preferably applied in said manufacture in an amount of 0.0001 to 50% by weight, preferably 0.001 to 40% by weight, more preferably 0.01 to 30% by weight, even more preferably 0.5 to 20% by weight and especially 2 to 10% by weight, based on the total weight of the topical composition, cosmetic composition, pharmaceutical composition and/or medicinal product.

Thus, another preferred subject of the instant invention is a composition for topical use as described herein, a topical composition, a cosmetic composition, a pharmaceutical composition and/or a medicinal product, comprising 0.0001 to 50% by weight, preferably 0.001 to 40% by weight, more preferably 0.01 to 30% by weight, even more preferably 0.5 to 20% by weight and especially 2 to 10% by weight of a composition according to the invention as described above and/or below, based on the total weight of said topical composition, cosmetic composition, pharmaceutical composition and/or medicinal product.

A method for the manufacture of a composition for topical use as described herein, comprising
a) providing a composition according to one or more of the claims 18 to 21,
b) providing one or more topically acceptable vehicles, and optionally
c) providing one or more further active compounds having a skin-care, hair-care and/or inflammation-inhibiting action,
d) and blending, mixing and/or homogenising a) and b), and optionally c), in any order.

Methods and devices for blending, mixing and/or homogenising a) and b), and optionally c) are known in the art and described herein. Further reference to the methods and devices described in the examples is made.

Subject of the instant invention is also a composition for topical use obtainable or preferably obtained according to the method described above.

Subject of the instant invention is also a composition for topical use as described herein, characterized in that it contains 0.0001 to 50% by weight, based on the total weight of said composition for topical use, of a cyclic peptide and a lipid containing composition as described above, and more preferably of a. composition, comprising
i) 0.0001 to 20% by weight of Cyclo-(Arg-Gly-Asp-DPhe-Acha), and/or a salt thereof,
ii) 0.001 to 50% by weight of one or more lipids; and especially of a composition, comprising
i) 0.0001 to 20% by weight of Cyclo-(Arg-Gly-Asp-DPhe-Acha), and/or a salt thereof,
ii) 0.001 to 50% by weight of one or more lipids, and
iii) 10 to 99.9979% by weight of water, and optionally
iv) 0.001 to 20% by weight of et least one further ingredient, preferably selected from the group consisting of ectoin, biotin, taurine, caffeine, taurine, purine, and/or derivatives thereof.

Especially preferred in this regards is the use of the above and/or below described compositions according to the invention for the prophylaxis against time- and/or light-induced ageing processes of the human skin or human hair, in particular for prophylaxis against dry skin, wrinkle formation and/or pigment defects, and/or for the reduction or prevention of the harmful effects of UV rays on the skin.

Especially preferred in this regard is the use of the compositions according to the invention as described above and/or below
a) as hair care, skin care, hair-growth, anti-ageing and/or or anti-wrinkle compositions; and/or
b) as the ingredient or active agent in hair care, skincare, hair growth, anti-ageing and/or or anti-wrinkle compositions, preferably conventional hair care, skincare, hair growth, anti-ageing and/or or anti-wrinkle compositions.

Another subject of the invention is a medicinal product, comprising one or more cyclic peptides as described above and/or below and especially comprising 0.0001 to 50% by weight, preferably 0.001 to 40% by weight, more preferably 0.01 to 30% by weight, even more preferably 0.5 to 20% by weight and especially 2 to 10% by weight, of a composition according to the invention as described above and/or below, based on the total weight of said medicinal product, and one or more carriers and/or excipients.

The compositions here are preferably non-therapeutical, more preferably either compositions which can be used topically, for example cosmetic or dermatological formulations, or foods or food supplements. In this case, the compositions comprise a cosmetically or dermatologically or food-suitable carrier and, depending on the desired property profile, optionally further suitable ingredients.

The use according to the invention of cyclic peptides according to the invention, especially the cyclic peptides according to formulae I, Ia, Ib, Ic, Id and/or Ie, in compositions offers, inter alia, protection against damage caused directly or indirectly by UV radiation or by processes caused by reactive compounds, such as, for example, skin ageing, loss of skin moisture, loss of skin elasticity, formation of wrinkles or lines or of pigment defects or age spots.

The present invention furthermore relates to the use of the above-mentioned compositions for the prevention of undesired changes in the skin picture, such as, for example, acne or greasy skin, keratoses, light-sensitive, inflammatory, erythematous, allergic or autoimmune-reactive reactions.

However, the compounds and compositions according to the invention preferably also serve for calming sensitive and irritated skin, for the preventative regulation of collagen, hyaluronic acid and elastin synthesis, stimulation of DNA synthesis, in particular in the case of deficient or hypoactive skin states, regulation of the transcription and translation of matrix-degrading enzymes, in particular of MMPs, increasing cell regeneration and regeneration of the skin, increasing the skin's own protective and repair mechanisms for DNA, lipids and/or proteins.

In addition, compounds which are preferred in accordance with the invention have advantages on incorporation into the compositions:
mono- and/or oligoglycosyl radicals improve the water solubility of the compounds to be employed in accordance with the invention;
straight-chain or branched $C_1$- to $C_{20}$-alkoxy groups, in particular the long-chain alkoxy functions, such as ethylhexyloxy groups, increase the oil solubility of the compounds;
i.e. the hydrophilicity or lipophilicity of the compounds according to the invention can be increased through a suitable choice of the substituents.

Glycosidic radicals which can be employed are in particular mono- or oligosaccharide radicals. Preference is given here to hexosyl radicals, in particular ramnosyl radicals and glucosyl radicals. However, other hexosyl radicals, for example allosyl, altrosyl, galactosyl, gulosyl, idosyl, mannosyl and talosyl, may also advantageously be used. It may also be advantageous to use pentosyl radicals. The glycosyl radicals may be linked to the basic structure by means of an α- or β-glycosidic link. A preferred disaccharide is, for example, 6-O-(6-deoxy-α-L-mannopyranosyl)-β-D-glucopyranoside.

However, in likewise preferred embodiments of the invention, the compositions according to the invention may also comprise cyclic peptides according to the invention, especially the cyclic peptides according to formulae I, Ia, Ib, Ic, Id and/or Ie, which are sparingly soluble or insoluble in the composition matrix. In this case, the compounds are preferably dispersed in finely divided form in the cosmetic composition.

The cyclic peptides according to the invention, especially the cyclic peptides according to formulae I, Ia, Ib, Ic, Id and/or Ie, are typically employed in accordance with the invention in amounts of from 0.01 to 20% by weight, preferably in amounts of from 0.1% by weight to 10% by weight and particularly preferably in amounts of from 1 to 8% by weight. The person skilled in the art has absolutely no difficulties in selecting the amount correspondingly depending on the intended action of the composition.

The protective action against oxidative stress or against the effect of free radicals can thus be further improved if the compositions comprise one or more further antioxidants, where the person skilled in the art has absolutely no difficulties in selecting antioxidants having a suitably fast or time-delayed action.

In a preferred embodiment of the present invention, at least one further skin-care ingredient is one or more antioxidants and/or vitamins.

For the above-mentioned reasons, it is particularly preferred here for the composition to comprise no retinol derivative.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), furthermore (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are furthermore described in WO 2006/111233 and WO 2006/111234.

Suitable antioxidants are also compounds of the general formula and/or B

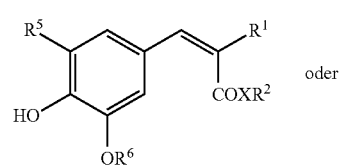

A oder

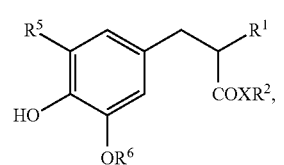

B wherein
R¹ is selected from the group consisting of —C(O)CH₃, —CO₂R³, —C(O)NH₂ and —C(O)N(R⁴)₂,
X is O or NH,
R² is linear or branched Alkyl having 1 to 30 C-atoms,
R³ is linear or branched Alkyl having 1 to 20 C-atoms,
R⁴ is in each case independently selected from the group consisting of H and linear or branched Alkyl having 1 to 8 C-atoms,
R⁵ is selected from the group consisting of linear or branched Alkyl having 1 to 8 C-atoms and linear or branched Alkoxy having 1 to 8 C-atoms and
R⁶ is selected from the group consisting of linear or branched Alkyl mit 1 to 8 C-atoms bedeutet, preferably selected from derivatives of the 2-(4-Hydroxy-3,5-dimethoxybenzyliden)-malonic acid and/or 2-(4-Hydroxy-3,5-dimethoxybenzyl)-malonic acid, and especially preferably selected from 2-(4-Hydroxy-3,5-dimethoxybenzyliden)-malonic acid-bis-(2-ethylhexyl) ester (z.B. Oxynex® ST Liquid) and/or 2-(4-Hydroxy-3,5-dimethoxybenzyl)-malonic acid-bis-(2-ethylhexyl)ester (z.B. RonaCare® AP).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed with cyclic peptides according to the invention, especially the cyclic peptides according to formulae I, Ia, Ib, Ic, Id and/or Ie, in compositions of this type in ratios in the range from 1000:1 to 1:1000, preferably in amounts of from 100:1 to 1:100.

The compositions according to the invention may comprise vitamins as further ingredients. The cosmetic compositions according to the invention preferably comprise vitamins and vitamin derivatives selected from vitamin B, thiamine chloride hydrochloride (vitamin B₁), riboflavin (vitamin B₂), nicotinamide, vitamin C (ascorbic acid), vitamin D, ergocalciferol (vitamin D₂), vitamin E, DL-α-tocopherol, tocopherol E acetate, tocopherol hydro-gensuccinate, vitamin K₁, esculin (vitamin P active ingredient), thiamine (vitamin B₁), nicotinic acid (niacin), pyridoxine, pyridoxal, pyridoxamine (vitamin B₆), pantothenic acid, biotin, folic acid and cobalamine (vitamin B₁₂), particularly preferably vitamin C and derivatives thereof, DL-α-tocopherol, tocopherol E acetate, nicotinic acid, pantothenic acid and biotin. Vitamins are usually employed here with cyclic peptides according to the invention, especially the cyclic peptides according to formulae I, Ia, Ib, Ic, Id and/or Ie, in ratios in the range from 1000:1 to 1:1000, preferably in amounts of from 100:1 to 1:100.

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101- 108, are concerned with effects of the substitution pattern of mono- and dihydroxyflavones. It is observed therein that dihydroxyflavones containing an OH group adjacent to the keto function or OH groups in the 3',4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers, I. M. C. M. Rietjens; Free Radical Biology & Medicine 2001, 31(7), 869-881, have investigated the pH dependence of the antioxidant action of hydroxyflavones. Quercetin exhibits the greatest activity amongst the structures investigated over the entire pH range.

Suitable antioxidants are furthermore compounds of the formula II

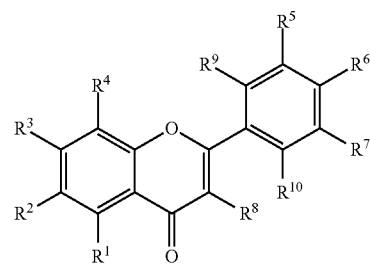

II where R¹ to R¹⁰ may be identical or different and are selected from
H
OR¹¹
straight-chain or branched C₁- to C₂₀-alkyl groups,
straight-chain or branched C₃- to C₂₀-alkenyl groups,
straight-chain or branched C₁- to C₂₀-hydroxyalkyl groups, where the hydroxyl group may be bonded to a primary or secondary carbon atom of the chain and furthermore the alkyl chain may also be interrupted by oxygen, and/or
C₃- to C₁₀-cycloalkyl groups and/or C₃- to C₁₂-cycloalkenyl groups, where the rings may each also be bridged by —(CH₂)ₙ— groups, where n=1 to 3,
where all OR¹¹ are, independently of one another,
OH
straight-chain or branched C₁- to C₂₀-alkoxy groups,
straight-chain or branched C₃- to C₂₀-alkenyloxy groups,
straight-chain or branched C₁- to C₂₀-hydroxyalkoxy groups, where the hydroxyl group(s) may be bonded to a primary or secondary carbon atom of the chain and furthermore the alkyl chain may also be interrupted by oxygen, and/or
C₃- to C₁₀-cycloalkoxy groups and/or C₃- to C₁₂-cycloalkenyl-oxy groups, where the rings may each also be bridged by —(CH₂)ₙ— groups, where n=1 to 3, and/or
mono- and/or oligoglycosyl radicals, with the proviso that at least 4 radicals from R¹ to R⁷ are OH and that the molecule contains at least two pairs of adjacent —OH groups, or $R^2$, $R^5$ and $R^6$ are OH and the radicals $R^1$, $R^3$, $R^4$ and $R^{7-10}$ are H, as described in the earlier German patent application DE 10244282.7.

Besides the advantages mentioned above, the advantages of the compositions according to the invention comprising at least one antioxidant here are, in particular, the antioxidant action and the good skin tolerability. In addition, the compounds described here are preferably colourless or have only a weak colour and thus only result in slight discoloration of the compositions, or none at all. Of particular advantage is preferably the particular action profile of the cyclic peptides according to the invention, especially the cyclic peptides according to formulae I, Ia, Ib, Ic, Id and/or Ie, which can preferably be shown in a DPPH assay in a high capacity for scavenging free radicals ($EC_{50}$), a time-delayed action ($T_{EC50}$>120 min) and thus a morate to high anti-free-radical efficiency (AE). In addition, the cyclic peptides according to the invention, especially the cyclic peptides according to formulae I, Ia, Ib, Ic, Id and/or Ie, preferably can combine antioxidative properties with UV absorption in the UV-A and/or UV-B region in the molecule. Preference is therefore also given to compositions, preferably non-therapeutic compositions, comprising at least one compound of the formula II which is characterised in that at least two adjacent radicals of the radicals $R^1$ to $R^4$ are OH and at least two adjacent radicals of the radicals $R^5$ to $R^7$ are OH. Particularly preferred compositions comprise at least one compound of the formula II which is characterised in that at least three adjacent radicals of the radicals $R^1$ to $R^4$ are OH, preferably with the radicals $R^1$ to $R^3$ being OH.

In order that the cyclic peptides according to the invention, especially the cyclic peptides according to formulae I, Ia, Ib, Ic, Id and/or Ie, are preferably able to develop their positive action as free-radical scavengers on the skin particularly well, it may be preferred to allow the cyclic peptides according to the invention, especially the cyclic peptides according to formulae I, Ia, Ib, Ic, Id and/or Ie, to penetrate into deeper skin layers. Several possibilities are available for this purpose. Firstly, the cyclic peptides according to the invention, especially the cyclic peptides according to formulae I, Ia, Ib, Ic, Id and/or Ie, can have an adequate lipophilicity in order to be able to penetrate through the outer skin layer into epidermal layers. As a further possibility, corresponding transport agents, for example liposomes, which enable transport of the cyclic peptides according to the invention, especially the cyclic peptides according to formulae I, Ia, Ib, Ic, Id and/or Ie, through the outer skin layers may also be provided in the composition. Finally, systemic transport of the cyclic peptides according to the invention, especially the cyclic peptides according to formulae I, Ia, Ib, Ic, Id and/or Ie, is preferably also conceivable. The composition is then designed, for example, in such a way that it is suitable for oral administration.

It is also advantageous to administer the compounds of the formula II in encapsulated form, for example as cellulose or chitin capsules, in gelatine or wax matrices or encapsulated with cyclodextrins.

It is assumed that the preferred cyclic peptides according to the invention, especially the cyclic peptides according to formulae I, Ia, Ib, Ic, Id and/or Ie, also act as enzyme inhibitors. They presumably inhibit protein kinases, elastase, aldose reductase and hyaluronidase, and therefore enable the intactness of the basic substance of vascular sheaths to be maintained. Furthermore, they presumably inhibit non-specifically catechol O-methyl transferase, causing the amount of available catecholamine and thus the vascular strength to be increased. Furthermore, they are thought to inhibit AMP phosphodiesterase, giving the substances potential for inhibiting thrombocyte aggregation.

Owing to these properties, the compositions according to the invention are, in general, suitable for immune protection and for the protection of DNA and RNA. In particular, the compositions are suitable for the protection of DNA and RNA against oxidative attack, against free radicals and against damage due to radiation, in particular UV radiation. A further advantage of the compositions according to the invention is cell protection, in particular protection of Langerhans cells against damage due to the above-mentioned influences. All these uses and the use of the cyclic peptides according to the invention, especially the cyclic peptides according to formulae I, Ia, Ib, Ic, Id and/or Ie, for the preparation of compositions which can be employed correspondingly are expressly also a subject-matter of the present invention. In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leucoplasia, leucoplasiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammations which are not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in tallow production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, and for the treatment of skin problems caused by UV radiation.

Compositions which are particularly preferred in accordance with the invention also comprise UV filters besides the one or more cyclic peptides according to the invention, especially the one or more cyclic peptides according to formulae I, Ia, Ib, Ic, Id and/or Ie.

Use of the dibenzoylmethane derivatives, which are particularly preferred as UV-A filters, in combination with the one or more cyclic peptides according to the invention, especially the one or more cyclic peptides according to formulae I, Ia, Ib, Ic, Id and/or Ie, gives rise to a further additional advantage: the UV-sensitive dibenzoylmethane derivatives are preferably additionally stabilised by the presence of the cyclic peptides according to the invention, especially the cyclic peptides according to formulae I, Ia, Ib, Ic, Id and/or Ie. The present invention therefore preferably furthermore relates to the use of one or more cyclic peptides according to the invention, especially the one or more cyclic peptides according to formulae I, Ia, Ib, Ic, Id and/or Ie, for the stabilisation of dibenzoylmethane derivatives in compositions.

In principle, all UV filters are suitable for combination with the one or more cyclic peptides according to the invention, especially the one or more cyclic peptides according to formulae I, Ia, Ib, Ic, Id and/or Ie. Particular preference is given to UV filters whose physiological acceptability has already been demonstrated. Both for UVA and UVB filters, there are many proven substances which are known from the specialist literature, for example:

benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N, N, N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL), benzoyl- or dibenzoylmethanes, such as 1-(4-tert-butylphenyl)-3-(4-methoxy-phenyl)propane-1,3-dione (for example Eusolex® 9020) or 4-isopropyldibenzoylmethane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex® 2292) or isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol) or 3,3,5-trimethylcyclohexyl salicylate (for example Eusolex® HMS), 4-aminobenzoic acid and derivatives, such as 4-aminobenzoic acid, 2-ethylhexyl 4-(dimethylamino)benzoate (for example Eusolex® 6007) or ethoxylated ethyl 4-aminobenzoate (for example Uvinul® P25), phenylbenzimidazolesulfonic acids, such as 2-phenylbenzimidazole-5-sulfonic acid and potassium, sodium and triethanolamine salts thereof (for example Eusolex® 232), 2,2'-(1,4-phenylene)bisbenzimidazole-4,6-disulfonic acid and salts thereof (for example Neoheliopan® AP) or 2,2-(1,4-phenylene)-bisbenzimidazole-6-sulfonic acid;

and further substances, such as
2-ethylhexyl 2-cyano-3,3-diphenylacrylate (for example Eusolex® OCR),
3,3'-(1,4-phenylenedimethylene)bis(7,7-dimethyl-2-oxobicyclo[2.2.1]hept-1-ylmethanesulfonic acid and salts thereof (for example Mexoryl® SX),
2,4,6-trianilino-(p-carbo-2'-ethylhexyl-1'-oxy)-1,3,5-triazine (for example Uvinul® T 150) and
hexyl 2-(4-diethylamino-2-hydroxybenzoyl)benzoate (for example Uvinul® UVA Plus, BASF).

The compounds mentioned in the list should only be regarded as examples. It is of course also possible to use other UV filters.

These organic UV filters are generally incorporated into cosmetic formulations in an amount of from 0.5 to 10 percent by weight, preferably 1-8%.

Further suitable organic UV filters are, for example, 2-(2H-benzotriazol-2-yl)-4-methyl-6-(2-methyl-3-(1,3,3,3-tetramethyl-1-(tri-methylsilyloxy)disiloxanyl)propyl) phenol (for example Silatrizole),
2-ethylhexyl 4,4'-[(6-[4-((1,1-dimethylethyl)aminocarbonyl)phenylamino]-1,3,5-triazine-2,4-diyl)diimino]bis (benzoate) (for example Uvasorb® HEB),
α-(trimethylsilyl)-ω-[trimethylsilyl)oxy]poly[oxy(dimethyl [and about 6% of methyl[2-[p-[2,2-bis(ethoxycarbonyl) vinyl]phenoxy]-1-methyleneethyl] and approximately 1.5% of methyl[3-[p-[2,2-bis(ethoxycarbonyl)vinyl]phenoxy]-propenyl] and from 0.1 to 0.4% of (methylhydrogen]silylene]] (n≈60) (CAS No. 207 574-74-1)
2,2'-methylenebis(6-(2H-benzotriazol-2-yl)-4-(1,1,3,3-tetramethylbutyl)-phenol) (CAS No. 103 597-45-1)
2,2'-(1,4-phenylene)bis(1H-benzimidazole-4,6-disulfonic acid, mono-sodium salt) (CAS No. 180 898-37-7),
2,4-bis{[4-(2-ethylhexyloxy)-2-hydroxy]phenyl}-6-(4-methoxyphenyl)-1,3,5-triazine (CAS No. 103 597-45-, 187 393-00-6) and
2-ethylhexyl 4,4''-[(6-[4-((1,1-dimethylethyl)aminocarbonyl)phenylamino]-1,3,5-triazine-2,4-diyl)diimino]bis (benzoate) (for example Uvasorb® HEB).

Further suitable UV filters are also methoxyflavones corresponding to the earlier German patent application DE 10232595.2.

Organic UV filters are generally incorporated into cosmetic formulations in an amount of from 0.5 to 20 percent by weight, preferably 1-15%.

Conceivable inorganic UV filters are those from the group consisting of titanium dioxides, such as, for example, coated titanium dioxide (for example Eusolex® T-2000, Eusolex® T-AQUA), zinc oxides (for example Sachtotec), iron oxides and also cerium oxides. These inorganic UV filters are generally incorporated into cosmetic compositions in an amount of from 0.5 to 20 percent by weight, preferably 2-10%.

Preferred compounds having UV-filtering properties are 3-(4'-methylbenzyl-idene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and its potassium, sodium and triethanolamine salts.

Through combination of one or more cyclic peptides according to the invention, especially the one or more cyclic peptides according to formulae I, la, Ib, Ic, Id and/or Ie, with further UV filters, the protective action against harmful influences of UV radiation can be optimised.

Optimised compositions may comprise, for example, the combination of the organic UV filters 4'-methoxy-6-hydroxyflavone with 1-(4-tert-butylphenyl)-3-(4-methoxyphenyl)propane-1,3-dione and 3-(4'-methylbenzylidene)-dl-camphor. This combination gives rise to broad-band protection, which can be supplemented by the addition of inorganic UV filters, such as titanium dioxide microparticles.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in compositions according to the invention in amounts which ensure that the encapsulated UV filters are present in the composition in the above-indicated amounts.

The skin-protecting or skin-care active ingredients can in principle be any active ingredients known to the person skilled in the art.

In an embodiment of the present invention, particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., Eur. J. Biochem., 149 (1985) pages 135-139). Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid) and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacteria cells. Pharmaceutical products, such as non-glycosylated, pharmaceutically active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lipsticks, rouge, make-ups, care creams and sunscreen compositions.

Preference is given here to the use of a pyrimidinecarboxylic acid of the following formula III

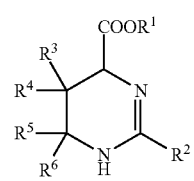

in which
$R^1$ is a radical H or C1-8-alkyl,
$R^2$ is a radical H or C1-4-alkyl,
and
$R^3$, $R^4$, $R^5$ and $R^6$ are each, independently of one another, a radical from the group consisting of H, OH, $NH_2$ and C1-4-alkyl. Preference is given to the use of pyrimidinecarboxylic acids in which $R^2$ is a methyl or ethyl group, and $R^1$ or $R^5$ and $R^6$ are H.

Particular preference is given to the use of the pyrimidinecarboxylic acids ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of from 100:1 to 1:100 with respect to the compounds of the formula one or more of the cyclic peptides according to the invention, especially one or more of the cyclic peptides according to formulae I, Ia, Ib, Ic, Id and/or Ie, with ratios in the range from 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and integumentary appendages. Compositions according to the invention which, in addition to the one or more of the cyclic peptides according to the invention, especially one or more of the cyclic peptides according to formulae I, Ia, Ib, Ic, Id and/or Ie, additionally comprise an aryl oxime, preferably 2-hydroxy-5-methyllaurophenone oxime, exhibit surprising antiinflammatory suitability. The compositions here preferably comprise from 0.01 to 10% by weight of the aryl oxime, it being particularly preferred for the composition to comprise from 0.05 to 5% by weight of aryl oxime.

All compounds or components which can be used in the compositions are either known or commercially available or can be synthesised by known processes. The preparation of the novel cyclic peptides is described below.

The one or more of the cyclic peptides according to the invention, especially one or more of the cyclic peptides according to formulae I, Ia, Ib, Ic, Id and/or Ie, can be incorporated into cosmetic or dermatological compositions in the customary manner. Suitable compositions are those for external use, for example in the form of a cream, lotion or gel or as a solution which can be sprayed onto the skin. Suitable for internal use are administration forms such as capsules, coated tablets, powders, tablet solutions or solutions.

Use forms of the compositions according to the invention that may be mentioned are, for example, solutions, suspensions, emulsions, PIT emulsions, pastes, ointments, gels, creams, lotions, powders, soaps, surfactant-containing cleansing preparations, oils, aerosols and sprays. Examples of other use forms are sticks, shampoos and shower compositions. Any desired customary carriers, assistants and, if desired, further active ingredients may be added to the composition.

Preferred assistants originate from the group consisting of preservatives, antioxidants, stabilisers, solubilisers, vitamins, colorants and odour improvers.

Ointments, pastes, creams and gels may comprise the customary carriers, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary carriers, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary carriers, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium meta-hydroxide, bentonite, agar-agar and tragacanth, or mixtures of these substances.

Soaps may comprise the customary carriers, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary carriers, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary carriers, such as synthetic oils, such as fatty acid esters, fatty alcohols, silicone oils, natural oils, such as vegetable oils and oily plant extracts, paraffin oils or lanolin oils, or mixtures of these substances.

Further typical cosmetic use forms are also lipsticks, lip-care sticks, mascara, eyeliner, eye-shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
  mineral oils, mineral waxes;
  oils, such as triglycerides of capric or caprylic acid, furthermore natural oils, such as, for example, castor oil;
  fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
  silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group consisting of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, or from the group consisting of esters of aromatic carboxylic acids and saturated and/or unsaturated, branched and/or unbranched alcohols having a chain length of from 3 to 30 carbon atoms. Ester oils of this type can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group consisting of branched and unbranched hydrocarbons and waxes, silicone oils, dialkyl ethers, or the group consisting of saturated and unsaturated, branched and unbranched alcohols, and fatty acid triglycerides, specifically the triglycerol esters of saturated and/or unsaturated, branched and/or unbranched alkanecarboxylic acids having a chain length of from 8 to 24, in particular 12-18, carbon atoms. The fatty acid triglycerides may advantageously be selected, for example, from the group consisting of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group consisting of 2-ethylhexyl isostearate, octyldodecanol, isotridecyl isononanoate, iso-eicosane, 2-ethylhexyl cocoate, $C_{12-15}$-alkyl benzoate, caprylic/capric acid tri-glyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane).

Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol or glycerol, and, in particular, one or more thickeners, which may advantageously be selected from the group consisting of silicon dioxide, aluminium silicates, polysaccharides and derivatives thereof, for example hyaluronic acid, xanthan gum, hydroxypropylmethylcellulose, particularly advantageously from the group consisting of the polyacrylates, preferably a polyacrylate from the group consisting of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group consisting of the alkylglucosides, acyl lactylates, betaines and coconut amphoacetates.

The alkylglucosides are themselves advantageously selected from the group consisting of the alkylglucosides which are distinguished by the structural formula

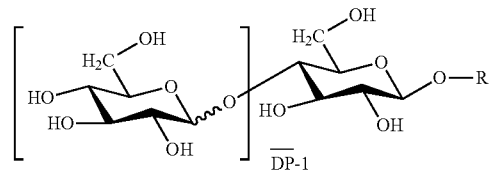

where R is a branched or unbranched alkyl radical having from 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \Sigma \frac{p_i}{100} \cdot i$$

in which $p_1, p_2, p_3 \ldots p_i$ represent the proportion of mono-, di-, tri- ... i-fold glucosylated products in percent by weight. Products which are advantageous according to the invention are those having degrees of glucosylation of 1-2, particularly advantageously of from 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used for the purposes of the invention are selected from the group consisting of octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and assistants or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group consisting of the substances which are distinguished by the structural formula

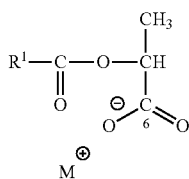

where $R^1$ is a branched or unbranched alkyl radical having from 1 to 30 carbon atoms, and $M^+$ is selected from the group consisting of the alkali metal ions and the group consisting of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group consisting of the substances which are distinguished by the structural formulae

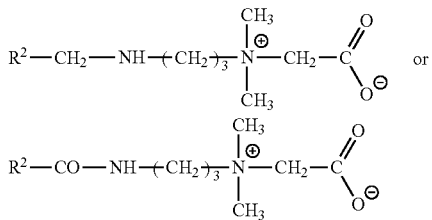

where $R^2$ is a branched or unbranched alkyl radical having from 1 to 30 carbon atoms.

$R^2$ is particularly advantageously a branched or unbranched alkyl radical having from 6 to 12 carbon atoms.

For example, capramidopropylbetaine, for example the product Tego Betain 810 from Th. Goldschmidt AG, is advantageous.

A coconut amphoacetate which is advantageous for the purposes of the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions are applied in sufficient amount to the skin and/or hair in the usual manner for cosmetics.

Cosmetic and dermatological compositions according to the invention may exist in various forms. Thus, they may be, for example, a solution, a water-free composition, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous according to the invention are, for example, O/W emulsifiers, principally from the group consisting of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following:

polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group consisting of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageous for the purposes of the invention can be the following:

fatty alcohols having from 8 to 30 carbon atoms, monoglycerol esters of saturated and/or unsaturated, branched and/or unbranched alkanecarboxylic acids having a chain length of from 8 to 24 carbon atoms, in particular 12-18 carbon atoms, diglycerol esters of saturated and/or unsaturated, branched and/or unbranched alkanecarboxylic acids having a chain length of from 8 to 24 carbon atoms, in particular 12-18 carbon atoms, monoglycerol ethers of saturated and/or unsaturated, branched and/or unbranched alcohols having a chain length of from 8 to 24 carbon atoms, in particular 12-18 carbon atoms, diglycerol ethers of saturated and/or unsaturated, branched and/or unbranched alcohols having a chain length of from 8 to 24 carbon atoms, in particular 12-18 carbon atoms, propylene glycol esters of saturated and/or unsaturated, branched and/or unbranched alkanecarboxylic acids having a chain length of from 8 to 24 carbon atoms, in particular 12-18 carbon atoms, and sorbitan esters of saturated and/or unsaturated, branched and/or unbranched alkanecarboxylic acids having a chain length of from 8 to 24 carbon atoms, in particular 12-18 carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate and glyceryl monocaprylate.

Preferred compositions according to the invention are particularly suitable for protecting human skin against ageing processes and against oxidative stress, i.e. against damage by free radicals, as are produced, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surfactants, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from one or more of the cyclic peptides according to the invention, especially one or more of the cyclic peptides according to formulae I, Ia, Ib, Ic, Id and/or Ie, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent changes of colour shade, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling or treating the hair, in the form of a lotion or gel for brushing or blow-waving, in the form of a hair lacquer, permanent waving composition, colorant or bleach for the hair. Besides the one or more of the cyclic peptides according to the invention, especially one or more of the cyclic peptides according to formulae I, Ia, Ib, Ic, Id and/or Ie, the composition having light-protection properties may comprise various adjuvants used in this type of composition, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The present invention furthermore relates to a process for the preparation of a composition which is characterised in that one or more of the cyclic peptides according to the invention, especially one or more of the cyclic peptides according to formulae I, Ia, Ib, Ic, Id and/or Ie, is mixed with a cosmetically or dermatologically or food-suitable carrier, and to the use of one or more of the cyclic peptides according to the invention, especially one or more of the cyclic peptides according to formulae I, Ia, Ib, Ic, Id and/or Ie, for the preparation of a composition.

The compositions according to the invention can be prepared here with the aid of techniques which are well known to the person skilled in the art.

The mixing can result in dissolution, emulsification or dispersal one or more of the cyclic peptides according to the invention, especially one or more of the cyclic peptides according to formulae I, Ia, Ib, Ic, Id and/or Ie, in the carrier.

It has also been noted that the cyclic peptides according to the invention, especially the cyclic peptides according to formulae I, Ia, Ib, Ic, Id and/or Ie, can have a stabilising effect on the composition. When used in corresponding products, the latter are thus also stable for longer and do not change their appearance. In particular, the effectiveness of the ingredients, for example vitamins, is retained even in the case of application over extended periods or extended storage. This is, inter alia, particularly advantageous in the case of compositions for protecting the skin against the effect of UV rays since these cosmetics are exposed to particularly high stresses by UV radiation.

The positive effects of the cyclic peptides according to the invention, especially o the cyclic peptides according to formulae I, Ia, Ib, Ic, Id and/or Ie, give rise to their particular suitability for use in cosmetic compositions, pharmaceutical compositions and/or medicinal products, and preferably in cosmetic or pharmaceutical compositions.

According to one aspect of the invention, the compositions contain one or more topically acceptable vehicles, one or more skin-tolerated and/or hair tolerated vehicles, and/or one or more compounds having skin-care, hair-care and/or inflammation-inhibiting action, preferably selected from the group consisting of:

UREA, DISODIUM PHOSPHATE, BIOTIN, CITRIC ACID, NIACINAMIDE, HYDROXYPROPYL GUAR, SODIUM COCOAMPHOACETATE, PROPYLENE GLYCOL, 5-BROMO-5-NITRO-1,3-DIOXANE, CAFFEINE, ETHOXYDIGLYCOL, PROPYLENE GLYCOL, BUTYLENE GLYCOL, SODIUM BENZOATE, POTASSIUM SORBATE, PANTHENOL, ALCOHOL, TOCOPHERYL ACETATE, MENTHOL, PEG-40 HYDROGENATED CASTOR OIL, SALICYLIC ACID, ISOPROPYL ALCOHOL, ISOQUERCETIN, PROPYLENE GLYCOL, ACRYLATES/C10-30 ALKYL ACRYLATE, CROSSPOLYMER, SUCROSE STEARATE, DECYL OLEATE, DIMETHICONE, SODIUM HYDROXIDE, CETEARYL ALCOHOL, CETEARETH-20, DISODIUM RUTINYL DISULPHATE, OLEYL ERUCATE, PROPYLPARABEN, METHYLPARABEN, CETEARYL ALCOHOL, BEHENTRIMONIUM CHLORIDE (Incroquat Behenyl TMC), CYCLOPENTASILOXANE, CYCLOHEXASILOXANE, PROPYLENE GLYCOL, DIAZOLIDINYL UREA, METHYLPARABEN/PROPYLPARABEN (Germaben II), ECTOIN, BENZOPHENONE-3, POLYVINYPYRROLIDONE (PVP), PVP/VA/VINYL PROPIONATE COPOLYMER, ETHANOL, ACRYLATES/C10-30 ALKYL ACRYLATE, CROSSPOLYMER (Carbopol Ultrez 21), PROPYLENE GLYCOL, DIAZOLIDINYL UREA, METHYLPARABEN, PROPYLPARABEN, CETRIMONIUM CHLORIDE, AQUA (WATER), ETHYLHEXYL, METHOXYCINNAMATE, SILICA, CHLORPHENESIN, BHT (Eusolex UV-Pearls 2292), AMMONIUM THIOGLYCOLATE, AMMONIUM BICARBONATE, POTASSIUM COCOYL HYDROLYZED COLLAGEN, NONOXYNOL-14, TOCOPHERYL ACETATE;

biotin, taurine, purine and/or derivatives thereof, melatonin, agomelatine, and/or salts thereof, L-carnitine and/or a salt thereof, pantolactone, taurine and/or a salt thereof;

vitamins, in particular, niacinamide, biotin, pantothenic acid and tocopherol and/or derivatives thereof, ubiquinone, ectoin, allantoin, plant extracts of echinacea or moringa plants;

xanthines, in particular caffeine, theophylline and theobromine;

flavonoids, flavonols, bisabolol and creatine, coumarin, and/or 3H-1,2-dithiole-3-thione (I), anethole dithiolethione, sulforaphane, phenethyl isothiocyanate, 6-(methylsulphinyl)hexyl isothiocyanate and allyl isothiocyanate, preferably in the treatment of of canitis;

more preferably selected from taurine, caffeine, theophylline and theobromine.

The properties of the cyclic peptides according to the invention, especially the cyclic peptides according to formulae I, Ia, Ib, Ic, Id and/or Ie should likewise be regarded as positive for use in foods or as food supplements or as functional foods. The further explanations given for foods also apply correspondingly to food supplements and functional foods.

The foods which can be enriched with one or more of the cyclic peptides according to the invention, especially one or more of the cyclic peptides according to formulae I, Ia, Ib, Ic, Id and/or Ie, include all materials which are suitable for consumption by animals or consumption by humans, for example vitamins and provitamins thereof, fats, minerals or amino acids. (The foods may be solid, but also liquid, i.e. in the form of a beverage).

The present invention accordingly furthermore relates to the use one or more of the cyclic peptides according to the invention, especially one or more of the cyclic peptides according to formulae I, Ia, Ib, Ic, Id and/or Ie, as food additive for human or animal nutrition, and to compositions which are foods or food supplements and comprise corresponding carriers.

Foods which can be enriched with one or more of the cyclic peptides according to the invention, especially one or more of the cyclic peptides according to formulae I, Ia, Ib, Ic, Id and/or Ie, are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more of the cyclic peptides according to the invention, especially one or more of the cyclic peptides according to formulae I, Ia, Ib, Ic, Id and/or Ie, are corn or cereals from a single plant species and materials produced from plant species of this type, such as, for example, cereal syrup, rye flour, wheat flour or oat bran. Mixtures of foods of this type are also suitable for being enriched with one or more of the cyclic peptides according to the invention, especially one or more of the cyclic peptides according to formulae I, Ia, Ib, Ic, Id and/or Ie, for example multivitamin preparations, mineral mixtures or sweetened juice. As further examples of foods which can be enriched with one or more of the cyclic peptides according to the invention, especially one or more of the cyclic peptides according to formulae I, Ia, Ib, Ic, Id and/or Ie, mention may be made of food compositions, for example prepared cereals, biscuits, mixed drinks, foods prepared especially for children, such as yoghurt, diet foods, low-calorie foods or animal feeds.

The foods which can be enriched with one or more of the cyclic peptides according to the invention, especially one or more of the cyclic peptides according to formulae I, Ia, Ib, Ic, Id and/or Ie, thus include all edible combinations of carbohydrates, lipids, proteins, inorganic elements, trace elements, vitamins, water or active metabolites of plants and animals.

The foods which can be enriched with one or more of the cyclic peptides according to the invention, especially one or more of the cyclic peptides according to formulae I, Ia, Ib, Ic, Id and/or Ie, are preferably administered orally, for example in the form of meals, pills, tablets, capsules, powders, syrup, solutions or suspensions.

The foods according to the invention enriched with one or more of the cyclic peptides according to the invention, especially one or more of the cyclic peptides according to formulae I, Ia, Ib, Ic, Id and/or Ie, can be prepared with the aid of techniques which are well known to the person skilled in the art.

Due to their action, the cyclic peptides according to the invention, especially the cyclic peptides according to formulae I, Ia, Ib, Ic, Id and/or Ie, are preferable also suitable as medicament ingredients. Cyclic peptides according to the invention, especially cyclic peptides according to formulae I, la, Ib, Ic, Id and/or Ie, can be used, for example, for preventative treatment of inflammation and allergies of the skin and in certain cases for preventing certain types of cancer. Cyclic peptides according to the invention, especially cyclic peptides according to formulae I, Ia, Ib, Ic, Id and/or Ie, are particularly suitable for the preparation of a medicament for the treatment of inflammation, allergies and irritation, in particular of the skin. It is furthermore possible to prepare medicaments which act as a vein tonic, as cuperose inhibitor, as chemical, physical or actinic erythema inhibitor, as agent for the treatment of sensitive skin, as decongestant, as desiccant, as slimming agent, as anti-wrinkle agent, as stimulator for the synthesis of components of the extracellular matrix, as strengthening agent for improving skin elasticity, and as anti-ageing agent. Furthermore, cyclic peptides according to the invention, especially cyclic peptides according to formulae I, Ia, Ib, Ic, Id and/or Ie, which are preferred in this connection exhibit antiallergic and anti-inflammatory and antiirritative actions. They are therefore suitable for the preparation of medicaments for the treatment of inflammation or allergic reactions.

Especially preferred according to the invention are subjects as described herein, wherein the characteristics of two or more preferred, more preferred and/or especially preferred embodiments, aspects and/or subjects are combined into one embodiment, aspect and/or subject.

The agents, compositions and/or formulations described herein may include or comprise, essentially consist of or consist of the said necessary and/or optional constituents. All compounds or components which can be used in the agents, compositions and/or formulations are either known and commercially available or can be synthesised by known processes.

The invention is explained in greater detail below by means of examples. The invention can be carried out throughout the range claimed and is not restricted to the examples given here.

Moreover, the following examples are given in order to assist the skilled artisan to better understand the present invention by way of exemplification. The examples are not intended to limit the scope of protection conferred by the claims. The features, properties and advantages exemplified for the compounds, compositions and/or uses defined in the examples may be assigned to other compounds, compositions and/or uses not specifically described and/or defined in the examples, but falling under the scope of what is defined in the claims.

EXPERIMENTAL

All temperatures stated above and below are in ° C. In the examples below, "customary working up" means: water is added if necessary, the mixture is neutralized and subjected to extraction with ether or dichloromethane, the phases are separated, the organic phase is dried over sodium sulfate, filtered and concentrated by evaporation and the residue is purified by chromatography on silica gel and/or crystallization. RT=retention time (minutes). Analysis was by HPLC on Lichrosorb® RP select B (7 µm)-250×4 mm column, Eluent A: 0.3% TFA in water; Eluent B: 0.3% TFA in 2-propanol/water (8:2) gradient 1-99% B in 50 minutes at 1 ml/min flow rate and detection at 215 nm. M+=molecular peak in the mass spectrum obtained by the "Fast Atom Bombardment" (FAB) method.

Example 1

A solution of 1.1 g of H-Arg(Mtr)-Gly-Asp(OBut)-D-Phe-hPro-ONa [obtainable, for example, from Fmoc-NMe-Arg(Mtr)-Gly-Asp(OBut)-D-Phe-hPro-O-Wang, -O-Wang being the radical of a 4-oxymethyl-phenoxymethyl-polystyrene resin used in the modified Merrifield techniques, by removal of the Fmoc group with piperidine/DMF and elimination of the resin with TFA/CH$_2$Cl$_2$(1:1)] in 15 ml of DMF is diluted with 85 ml of dichloromethane, and 50 mg of NaHCO$_3$ are added. After cooling in a dry ice/acetone mixture, 40 µl of diphenylphosphoryl azide are added. After standing at room temperature for 16 hours, the solution is concentrated. The concentrate is gel-filtered (Sephadex 010 column in isopropanol/water 8:2) and then purified by HPLC in the customary manner. Treatment with TFA/H$_2$O (98:2) gives cyclo-(Arg-Gly-Asp-D-Phe-hPro); RT=18.5; FAB-MS (M+H): 587.

The following are obtained analogously by cyclization of the corresponding linear peptides and removal of the protecting groups:
cyclo-(Arg-Gly-Asp-DPhe-Nle);RT=25.3;FAB-MS(M+H): 589;
cyclo-(Arg-Gly-Asp-Phe-Ahds);RT=35.1;FAB-MS(M+H): 730;
cyclo-(Arg-Gly-Asp-DPhe-Ahds);RT=35.4;FAB-MS(M+H):730;
cyclo-(Arg-Gly-Asp-Phe-DAhds);RT=35.7;FAB-MS(M+H):730;
cyclo-(Arg-Gly-Asp-DPhe-Aos);
cyclo-(Arg-Gly-Asp-DPhe-DAos);
cyclo-(Arg-Gly-Asp-Phe-DAos);
cyclo-(Arg-Gly-Asp-DPhe-Nhdg);RT=36.7;FAB-MS(M+H):758;
cyclo-(Arg-Gly-Asp-Phe-Nhdg);RT=36.5;FAB-MS(M+H): 758;
cyclo-(Arg-Gly-Asp-DPhe-DNhdg);FAB-MS(M+H):758;
cyclo-(Arg-Gly-Asp-Phe-DNhdg);FAB-MS(M+H):758;
cyclo-(Arg-Gly-Asp-DPhg-Nhdg);
cyclo-(Arg-Gly-Asp-Phg-Nhdg);
cyclo-(Arg-Gly-Asp-DPhg-DNhdg);
cyclo-(Arg-Gly-Asp-Phg-DNhdg);
cyclo-(Arg-Gly-Asp-DPhe-Acha);RT=25.2;FAB-MS(M+H):601;
cyclo-(Arg-Gly-Asp-Phe-Acha);FAB-MS(M+H):601;
cyclo-(Arg-Gly-Asp-DPhe-DAcha);FAB-MS(M+H):601;
cyclo-(Arg-Gly-Asp-Phe-DAcha);FAB-MS(M+H):601;
cyclo-(Arg-Gly-Asp-DPhe-Aib);FAB-MS(M+H):575;
cyclo-(Arg-Gly-Asp-Phe-Aib); RT=36.5;FAB-MS(M+H): 575;
cyclo-(Arg-Gly-Asp-DPhe-DAib);FAB-MS(M+H):575;
cyclo-(Arg-Gly-Asp-Phe-DAib);FAB-MS(M+H):575;
cyclo-(Arg-Gly-Asp-DPhe-Acpa);RT=17.1;FAB-MS(M+H):587;
cyclo-(Arg-Gly-Asp-Phe-Acpa);FAB-MS(M+H):587;
cyclo-(Arg-Gly-Asp-DPhe-DAcpa);FAB-MS(M+H):587;
cyclo-(Arg-Gly-Asp-Phe-DAcpa);FAB-MS(M+H):587;
cyclo-(Arg-Gly-Asp-DPhe-Tle);RT=19.1;FAB-MS(M+H): 589;
cyclo-(Arg-Gly-Asp-Phe-Tle);FAB-MS(M+H):589;
cyclo-(Arg-Gly-Asp-DPhe-DTle);FAB-MS(M+H):589;
cyclo-(Arg-Gly-Asp-Phe-DTle);FAB-MS(M+H):589;
cyclo-(Arg-Gly-Asp-Dphe(4-Cl)-Tle);RT=23.2;FAB-MS (M+H):623;
cyclo-(Arg-Gly-Asp-Phe(4-Cl)-Tle);FAB-MS(M+H):623;
cyclo-(Arg-Gly-Asp-DPhe(4-Cl)-DTle);FAB-MS(M+H): 623;
cyclo-(Arg-Gly-Asp-Phe(4-Cl)-DTle);FAB-MS(M+H):623;
cyclo-(Arg-Gly-Asp-Dphe(4-F)-Tle);RT=20.2;FAB-MS (M+H):607;
cyclo-(Arg-Gly-Asp-Phe(4-F)-Tle);FAB-MS(M+H):607;
cyclo-(Arg-Gly-Asp-DPhe(4-F)-DTle);FAB-MS(M+H): 607;
cyclo-(Arg-Gly-Asp-Phe(4-F)-DTle);FAB-MS(M+H):607.

Example 2

A solution of 0.28 g of cyclo-(Arg(Mtr)-Gly-Asp-DPhe-DhPro)[obtainable by cyclization according to Ex. 1] in 8.4 ml of TFA, 1.7 ml of dichloromethane and 0.9 ml of thiophenol is allowed to stand at room temperature for 4 hours, then concentrated, and the residue is diluted with water and then freeze-dried. Gel filtration on Sephadex G 10 (acetic acid/water 1:1) and subsequent purification by preparative HPLC under the conditions indicated give cyclo-(Arg-Gly-Asp-DPhe-DhPro); FAB-MS (M+H): 587.

The following are obtained analogously:
from cyclo-(Arg(Mtr)-Gly-Asp-Phe-DhPro):
  cyclo-(Arg-Gly-Asp-Phe-DhPro);
  FAB-MS (M+H): 587;
from cyclo-(Arg(Mtr)-Gly-Asp(OBut)-DPhg-Tle):
  cyclo-(D-Arg-NMeGly-Asp-DPhg-Tle);
from cyclo-(Arg(Mtr)-Gly-Asp(OEt)-DPhg-hPro):
  cyclo-(Arg-Gly-Asp-DPhg-h Pro);
from cyclo-(Arg(Mtr)-Gly-Asp-Phg-DAhds):
  cyclo-(Arg-Gly-Asp-Phg-DAhds);
from cyclo-(Arg(Mtr)-Gly-Asp-DPhg-Acpa):
  cyclo-(Arg-Gly-Asp-DPhg-Acpa);
from cyclo-(Arg(Mtr)-Gly-Asp-DPhg-Aos):
  cyclo-(Arg-Gly-Asp-DPhg-Aos).

Example 3

80 mg of cyclo-(Arg-Gly-Asp-DPhe-hPro) [obtainable according to Ex. 1] are dissolved in 0.01 m HCl five to six times and freeze-dried after each dissolving operation. Subsequent purification by HPLC gives cyclo-(Arg-Gly-Asp-DPhe-hPro)×HCl.

The following are obtained analogously:
from cyclo-(Arg-Gly-Asp-DPhe-Nle):
  cyclo-(NMeArg-Gly-Asp-DPhe-Nle)×HCl;
from cyclo-(Arg-Gly-Asp-DPhe-Ahds):
  cyclo-(Arg-Gly-Asp-DPhe-Ahds)×HCl;
from cyclo-(Arg-Gly-Asp-DPhe-Ahds):
  cyclo-(Arg-Gly-Asp-DPhe-Ahds)×HCl.

Example 4

To prepare affinity phases, 0.9 g of N-maleimido-(CH$_2$)$_5$—CO—NH—(CH$_2$)$_3$ polymer [obtainable by condensation of N-maleimido-(CH$_2$)$_5$—COOH with H$_2$N—(CH$_2$)$_3$ polymer] is suspended in 10 ml of 0.1 M sodium phosphate buffer at a pH of 7, and one equivalent cyclo-(Arg-Gly-Asp-DPhe(4-N—CO(CH$_2$)$_2$SH)-hPro) [obtainable by cyclization of H-Dphe(4-NH-BOC)-hPro-Arg(Mtr)-Gly-Asp-OH, removal of the protecting groups and acylation with, for example, Cl—CO(CH$_2$)$_2$SH] is added at 4°. The reaction mixture is stirred for 4 hours with simultaneous warming to room temperature, and the solid residue is filtered off and washed twice with 10 ml each of buffer solution (pH 7) and then three times with 10 ml each time of water. Cyclo-(Arg-Gly-Asp-DPhe(4-N—CO(CH$_2$)$_2$S-3-(N-maleimido-(CH$_2$)$_5$—CONH—(CH$_2$)$_3$-polymer)-hPro)) is obtained.

Example 5

Analogously to Example 4, condensation of polymer-O—(CH$_2$)$_3$—NH$_2$ [commercially available] and cyclo-(Arg-Gly-Asp-DPhe(4-N—CO(CH$_2$)$_4$—COOH)=hPro) [obtainable by condensing adipic acid with cyclo-(Arg(Mtr)-Gly-Asp-DPhe-(4-NH-BOC)-hPro) under the conditions stated in Ex. 4] gives the following polymeric phase: cyclo-(Arg-Gly-Asp-DPhe(4-N—CO—(CH$_2$)$_4$—CO—NH—(CH$_2$)$_3$—O-polymer)-hPro.

In the examples below, "customary working up" means: water is added if necessary, the mixture is neutralized and subjected to extraction with ether or dichloroethane, the phases are separated, the organic phase is dried over sodium sulfate, filtered and concentrated by evaporation and the residue is purified by chromatography on silica gel and/or crystallization. RT=retention time (minutes). Analysis was by HPLC on Lichrosorb® RP select B (7 μm)-250×4 mm column, Eluent A: 0.3% TFA in water; Eluent B: 0.3% TFA in 2-propanol/water (8:2) gradient 1-99% B in 50 minutes at 1 ml/min flow rate and detection at 215 nm. M+=molecular peak in the mass spectrum obtained by the "Fast Atom Bombardment" (FAB) method.

Example 6

A solution of 0.6 g of H-NMe-Arg(Mtr)-Gly-Asp(OBut)-D-Phe-Val-ONa [obtainable for example from Fmoc-NMe-Arg(Mtr)-Gly-Asp(OBut)-D-Phe-Val-O-Wang, -O-Wang being the radical of a 4-hydroxymethyl-phenoxymethyl-polystyrene resin used in the modified Merrifield techniques, by removal of the Fmoc group with piperidine/DMF and elimination of the resin with TFA/CH$_2$Cl$_2$ (1:1)] in 15 ml of DMF is diluted with 85 ml of dichloromethane, and 50 mg of NaHCO$_3$ are added. After cooling in a dry ice/acetone mixture, 40 III of diphenylphosphoryl azide are added. After standing at room temperature for 16 hours, the solution is concentrated. The concentrate is gel-filtered (Sephadex 010 column in isopropanol/water 8:2) and then purified by HPLC in the customary manner. Treatment with TFA/H$_2$ 0 (98:2) gives cyclo-(NMe-Arg-Gly-Asp-D-Phe-Val); RT=18.1; FAB-MS (M+H): 589.

The following are obtained analogously by cyclization of the corresponding linear peptides and elimination of the protecting groups:
cyclo-(Arg-NMeGly-Asp-DPhe-Val); RT=17.9; FAB-MS (M+H): 589;
cyclo-(Arg-Gly-NMeAsp-DPhe-Val); RT=18.3; FAB-MS (M+H): 589;
cyclo-(Arg-Gly-NMeAsp-DPhe-Val)×TFA; RT=15.4; FAB-MS(M+H): 589;
cyclo-(Arg-Gly-Asp-NMeDPhe-Val); RT=18.9; FAB-MS (M+H): 589;
cyclo-(Arg-Gly-Asp-DPhe-NMeVal); RT=19.5; FAB-MS (M+H): 589;
cyclo-(Arg-Gly-Asp-DPhe-NMeLys); RT=11.1; FAB-MS (M+H): 618;
cyclo-(Arg-Gly-Asp-DPhe-NMeLys(benzyloxycarbonyl)×TFA=23.4; FAB-MS (M+H): 752;
cyclo-(NEtArg-Gly-Asp-DPhe-Val); FAB-MS (M+H): 603;
cyclo-(Arg-NEtGly-Asp-DPhe-Val); FAB-MS (M+H): 603;
cyclo-(Arg-Gly-NEtAsp-DPhe-Val); FAB-MS (M+H): 603;
cyclo-(Arg-Gly-Asp-NEtDPhe-Val); FAB-MS (M+H): 603;
cyclo-(Arg-Gly-Asp-DPhe-NEtVal); FAB-MS (M+H): 603;
cyclo-(Arg-Gly-Asp-DPhe(4-I)-NMeVal); RT=23.5; FAB-MS(M+H): 715;
cyclo-(NPrArg-Gly-Asp-DPhe-Val); FAB-MS (M+H): 617;
cyclo-(Arg-NPrGly-Asp-DPhe-Val); FAB-MS (M+H): 617;
cyclo-(Arg-Gly-NPrAsp-DPhe-Val); FAB-MS (M+H): 617;
cyclo-(Arg-Gly-Asp-NPrDPhe-Val); FAB-MS (M+H): 617;
cyclo-(Arg-Gly-Asp-DPhe-NPrVal); FAB-MS (M+H): 617;
cyclo-(NBzlArg-Gly-Asp-DPhe-Val); FAB-MS (M+H): 665;
cyclo-(Arg-NBzlGly-Asp-DPhe-Val); FAB-MS (M+H): 665;
cyclo-(Arg-Gly-NBzlAsp-DPhe-Val); FAB-MS (M+H): 665;
cyclo-(Arg-Gly-Asp-NBzlDPhe-Val); FAB-MS (M+H): 665;
cyclo-(Arg-Gly-Asp-DPhe-NBzlVal); FAB-MS (M+H): 665;
cyclo-(Arg-Gly-Asp-Phe-DNMeVal)×TFA; RT=18.2; FAB-MS(M+H): 589;
cyclo-(NMeArg-Gly-Asp-DPhe-Leu); FAB-MS (M+H): 603;
cyclo-(Arg-NMeGly-Asp-DPhe-Leu); FAB-MS (M+H): 603;
cyclo-(Arg-Gly-NMeAsp-DPhe-Leu); FAB-MS (M+H): 603;
cyclo-(Arg-Gly-Asp-NMeDPhe-Leu); FAB-MS (M+H): 603;
cyclo-(Arg-Gly-Asp-DPhe-NMeLeu); FAB-MS (M+H): 603;
cyclo-(NEtArg-Gly-Asp-DPhe-Leu); FAB-MS (M+H): 617;
cyclo-(Arg-NEtGly-Asp-DPhe-Leu); FAB-MS (M+H): 617;
cyclo-(Arg-Gly-NEtAsp-DPhe-Leu); FAB-MS (M+H): 617;
cyclo-(Arg-Gly-Asp-NEtDPhe-Leu); FAB-MS (M+H): 617;
cyclo-(Arg-Gly-Asp-DPhe-NEtLeu); FAB-MS (M+H): 617;
cyclo-(NPrArg-Gly-Asp-DPhe-Leu); FAB-MS (M+H): 631;
cyclo-(Arg-NPrGly-Asp-DPhe-Leu); FAB-MS (M+H): 631;
cyclo-(Arg-Gly-NPrAsp-DPhe-Leu); FAB-MS (M+H): 631;
cyclo-(Arg-Gly-Asp-NPrDPhe-Leu); FAB-MS (M+H): 631;
cyclo-(Arg-Gly-Asp-DPhe-NPrLeu); FAB-MS (M+H): 631;
cyclo-(NBzlArg-Gly-Asp-DPhe-Leu); FAB-MS (M+H): 679;
cyclo-(Arg-NBzlGly-Asp-DPhe-Leu); FAB-MS (M+H): 679;
cyclo-(Arg-Gly-NBzlAsp-DPhe-Leu); FAB-MS (M+H): 679;
cyclo-(Arg-Gly-Asp-NBzlDPhe-Leu); FAB-MS (M+H): 679;
cyclo-(Arg-Gly-Asp-DPhe-NBzlLeu); FAB-MS (M+H): 679;
cyclo-(NMeArg-Gly-Asp-DPhe-Ala);
cyclo-(Arg-NMeGly-Asp-DPhe-Ala);
cyclo-(Arg-Gly-NMeAsp-DPhe-Ala);
cyclo-(Arg-Gly-Asp-NMeDPhe-Ala);
cyclo-(Arg-Gly-Asp-DPhe-NMeAla); RT=16.2; FAB-MS (M+H): 561;
cyclo-(NEtArg-Gly-Asp-DPhe-Ala);
cyclo-(Arg-NEtGly-Asp-DPhe-Ala);
cyclo-(Arg-Gly-NEtAsp-DPhe-Ala);
cyclo-(Arg-Gly-Asp-N EtD Phe-Ala);
cyclo-(Arg-Gly-Asp-DPhe-NEtAla);
cyclo-(N PrArg-Gly-Asp-DPhe-Ala);
cyclo-(Arg-N PrGly-Asp-DPhe-Ala);
cyclo-(Arg-Gly-NPrAsp-DPhe-Ala);
cyclo-(Arg-Gly-Asp-NPrDPhe-Ala);
cyclo-(Arg-Gly-Asp-DPhe-N PrAla);
cyclo-(NBzlArg-Gly-Asp-DPhe-Ala);
cyclo-(Arg-NBzlGly-Asp-DPhe-Ala);
cyclo-(Arg-Gly-NBzlAsp-DPhe-Ala);
cyclo-(Arg-Gly-Asp-NBzlDPhe-Ala);
cyclo-(Arg-Gly-Asp-DPhe-NBzlAla);
cyclo-(NMeArg-Gly-Asp-DPhe-Gly);
cyclo-(Arg-NMeGly-Asp-DPhe-Gly);
cyclo-(Arg-Gly-NMeAsp-DPhe-Gly);
cyclo-(Arg-Gly-Asp-NMeDPhe-Gly);
cyclo-(Arg-Gly-Asp-DPhe-NMeGly); RT=14.3; FAB-MS (M+H): 547;
Cyclo-(DArg-Gly-Asp-DPhe-NMeVal)×TFA; RT=18.7; FAB-MS(M+H): 589;
cyclo-(NEtArg-Gly-Asp-DPhe-Gly);
cyclo-(Arg-NEtGly-Asp-DPhe-Gly);
cyclo-(Arg-Gly-NEtAsp-DPhe-Gly);
cyclo-(Arg-Gly-Asp-NEtDPhe-Gly);

cyclo-(Arg-Gly-Asp-DPhe-NEtGly);
cyclo-(NPrArg-Gly-Asp-DPhe-Gly);
cyclo-(Arg-NPrGly-Asp-DPhe-Gly);
cyclo-(Arg-Gly-NPrAsp-DPhe-Gly);
cyclo-(Arg-Gly-Asp-NPrDPhe-Gly);
cyclo-(Arg-Gly-Asp-DPhe-NPrGly);
cyclo-(NBzlArg-Gly-Asp-DPhe-Gly);
cyclo-(Arg-NBzlGly-Asp-DPhe-Gly);
cyclo-(Arg-Gly-NBzlAsp-DPhe-Gly);
cyclo-(Arg-Gly-Asp-NBzlDPhe-Gly);
cyclo-(Arg-Gly-Asp-DPhe-NBzlGly);
cyclo-(NMeArg-Gly-Asp-Phg-Val) (SEQ ID NO: 1);
cyclo-(Arg-NMeGly-Asp-Phg-Val) (SEQ ID NO: 2);
cyclo-(Arg-Gly-NMeAsp-Phg-Val) (SEQ ID NO: 3);
cyclo-(Arg-Gly-Asp-NMePhg-Val) (SEQ ID NO: 4);
cyclo-(Arg-Gly-Asp-Phg-NMeVal) (SEQ ID NO: 5);
cyclo-(NEtArg-Gly-Asp-Phg-Val) (SEQ ID NO: 6);
cyclo-(Arg-NEtGly-Asp-Phg-Val) (SEQ ID NO: 7);
cyclo-(Arg-Gly-NEtAsp-Phg-Val) (SEQ ID NO: 8);
cyclo-(Arg-Gly-Asp-NEtPhg-Val) (SEQ ID NO: 9);
cyclo-(Arg-Gly-Asp-Phg-NEtVal) (SEQ ID NO: 10);
cyclo-(NPrArg-Gly-Asp-Phg-Val) (SEQ ID NO: 11);
cyclo-(Arg-NPrGly-Asp-Phg-Val) (SEQ ID NO: 12);
cyclo-(Arg-Gly-NPrAsp-Phg-Val) (SEQ ID NO: 13);
cyclo-(Arg-Gly-Asp-NPrPhg-Val) (SEQ ID NO: 14);
cyclo-(Arg-Gly-Asp-Phg-NPrVal) (SEQ ID NO: 15);
cyclo-(NBzlArg-Gly-Asp-Phg-Val) (SEQ ID NO: 16);
cyclo-(Arg-NBzlGly-Asp-Phg-Val) (SEQ ID NO: 17);
cyclo-(Arg-Gly-NBzlAsp-Phg-Val) (SEQ ID NO: 18);
cyclo-(Arg-Gly-Asp-NBzlPhg-Val) (SEQ ID NO: 19);
cyclo-(Arg-Gly-Asp-Phg-NBzlVal) (SEQ ID NO: 20);
cyclo-(NMeArg-Gly-Asp-Trp-Val) (SEQ ID NO: 21);
cyclo-(Arg-NMeGly-Asp-Trp-Val) (SEQ ID NO: 22);
cyclo-(Arg-Gly-NMeAsp-Trp-Val) (SEQ ID NO: 23);
cyclo-(Arg-Gly-Asp-NMeTrp-Val) (SEQ ID NO: 24);
cyclo-(Arg-Gly-Asp-Trp-NMeVal) (SEQ ID NO: 25);
cyclo-(NEtArg-Gly-Asp-Trp-Val) (SEQ ID NO: 26);
cyclo-(Arg-NEtGly-Asp-Trp-Val) (SEQ ID NO: 27);
cyclo-(Arg-Gly-NEtAsp-Trp-Val) (SEQ ID NO: 28);
cyclo-(Arg-Gly-Asp-NEtTrp-Val) (SEQ ID NO: 29);
cyclo-(Arg-Gly-Asp-Trp-NEtVal) (SEQ ID NO: 30);
cyclo-(NPrArg-Gly-Asp-Trp-Val) (SEQ ID NO: 31);
cyclo-(Arg-NPrGly-Asp-Trp-Val) (SEQ ID NO: 32);
cyclo-(Arg-Gly-NPrAsp-Trp-Val) (SEQ ID NO: 33);
cyclo-(Arg-Gly-Asp-NPrTrp-Val) (SEQ ID NO: 34);
cyclo-(Arg-Gly-Asp-Trp-NPrVal) (SEQ ID NO: 35);
cyclo-(NBzlArg-Gly-Asp-Trp-Val) (SEQ ID NO: 36);
cyclo-(Arg-NBzGlyy-Asp-Trp-Val) (SEQ ID NO: 37);
cyclo-(Arg-Gly-NBzlAsp-Trp-Val) (SEQ ID NO: 38);
cyclo-(Arg-Gly-Asp-NBzlTrp-Val) (SEQ ID NO: 39);
cyclo-(Arg-Gly-Asp-Trp-NBzlVal) (SEQ ID NO: 40).

Example 7

A solution of 0.28 g of cyclo-(Arg(Mtr)-Gly-Asp-NMePhe-Dval) [obtainable by cyclization according to Ex. 1] in 8.4 ml of TFA, 1.7 ml of dichloromethane and 0.9 ml of thiophenol is allowed to stand at room temperature for 4 hours, then concentrated, and the residue is diluted with water and then freeze-dried. Gel filtration on Sephadex G 10 (acetic acid/water 1:1) and subsequent purification by preparative HPLC under the conditions indicated give cyclo-(Arg-Gly-Asp-NMePhe-DVal); FAB-MS (M+H): 589.

The following are obtained analogously:
from cyclo-(Arg(Mtr)-Gly-NMeAsp-DPhe-Ile): cyclo-(Arg-Gly-NMeAsp-DPhe-Ile); FAB-MS (M+H): 603;

from cyclo-(D-Arg(Mtr)-NMeGly-Asp(OBut)-DPhe-Nle): cyclo-(D-Arg-NMeGly-Asp-DPhe-Nle);
from cyclo-(NMeArg(Mtr)-Gly-D-Asp(OEt)-DPhe-Ile): cyclo-(NMeArg-Gly-D-Asp-DPhe-Ile);
from cyclo-(NMeArg(Mtr)-Gly-Asp-Phe-DIle): cyclo-(NMeArg-Gly-Asp-Phe-DIle);
from cyclo-(Arg(Mtr)-Gly-NMeAsp-Phe-DLeu): cyclo-(Arg-Gly-NMeAsp-Phe-DLeu);
from cyclo-(Arg(Mtr)-NMeGly-Asp-Phe-DSer): cyclo-(Arg-NMeGly-Asp-Phe-DSer);
from cyclo-(Arg(Mtr)-NMeGly-Asp-DNal-Leu): cyclo-(Arg-NMeGly-Asp-DNal-Leu);
from cyclo-(NMeArg(Mtr)-Gly-Asp-Nal-DIle): cyclo-(NMeArg-Gly-Asp-Nal-DIle);
from cyclo-(Arg(Mtr)-Gly-Asp-NMePhg-DVal): cyclo-(Arg-Gly-Asp-NMePhg-DVal);
from cyclo-(Arg(Mtr)-Gly-NMeAsp-Trp-DVal): cyclo-(Arg-Gly-NMeAsp-Trp-DVal).

Example 8

80 mg of cyclo-(Arg-Gly-Asp-DPhe-NMeVal) are dissolved in 0.01 m HCl five to six times and freeze-dried after each dissolving operation. Subsequent purification by HPLC gives cyclo-(Arg-Gly-Asp-DPhe-NMeVal)×HCl; FAB-MS (M+H): 589.

The following are obtained analogously:
from cyclo-(NMeArg-Gly-Asp-DPhe-Val): cyclo-(NMeArg-Gly-Asp-DPhe-Val)×HCl;
from cyclo-(Arg-NMeGly-Asp-DPhe-Val): cyclo-(Arg-NMeGly-Asp-DPhe-Val)×HCl; FAB-MS (M+H): 589;
from cyclo-(Arg-Gly-NMeAsp-DPhe-Val): cyclo-(Arg-Gly-NMeAsp-DPhe-Val)×HCl;
from cyclo-(Arg-Gly-Asp-NMeDPhe-Val): cyclo-(Arg-Gly-Asp-NMeDPhe-Val)×HCl;
from cyclo-(Arg-Gly-Asp-Phe-DNMeVal): cyclo-(Arg-Gly-Asp-Phe-DNMeVal)×HCl; RT=18.2; FAB-MS(M+H): 589.
Analogously the following is obtained by the treatment with acetic acid (AcOH):
from cyclo-(Arg-Gly-NMeAsp-DPhe-Val): cyclo-(Arg-Gly-NMeAsp-DPhe-Val)×AcOH; RT=15.4; FAB-MS(M+H): 589.
Analogously the following is obtained by the treatment with methane sulfonic acid (MeSO$_3$H):
from cyclo-(Arg-Gly-Asp-DPhe-NMeVal): cyclo-(Arg-Gly-Asp-DPhe-NMeVal)×MeSO$_3$H; RT=17.8; FAB-MS(M+H): 589;

Example 9

To prepare affinity phases, 0.9 g of N-maleimido-(CH$_2$)$_5$—CO—NH—(CH$_2$)$_3$ polymer [obtainable by condensation of N-maleimido-(CH$_2$)$_5$—COOH with H$_2$N—(CH$_2$)$_3$ polymer] is suspended in 10 ml of 0.1 M sodium phosphate buffer at a pH of 7, and one equivalent cyclo-(Arg-Gly-Asp-DPhe-NMeLys(CO(CH$_2$)$_2$SH) is added at 4°. The reaction mixture is stirred for 4 hours with simultaneous warming to room temperature, and the solid residue is filtered off and washed twice with 10 ml each of buffer solution (pH 7) and then three times with 10 ml each time of water. Cyclo-(Arg-Gly-Asp-DPhe-NMeLys(CO(CH$_2$)$_2$S-3-(N-maleimido-(CH$_2$)$_5$—CONH—(CH$_2$)$_3$ polymer)) is obtained.

Example 10

Analogously to Example 9, condensation of polymer-O—(CH$_2$)$_3$—NH$_2$ [commercially available] and cyclo-(Arg- Gly-Asp-NMe-DPhe-Lys(CO(CH$_2$)$_4$COOH) [obtainable by condensing adipic acid with cyclo-(Arg-Gly-Asp-NMe-DPhe-Lys) under the stated conditions] gives the following polymeric phase: cyclo-(Arg-Gly-Asp-NMe-DPhe-Lys-(C0-(CH$_2$)$_4$—CO—NH—(CH$_2$)$_3$—O-polymer)

The following is obtained analogously by condensation of:
cyclo-(NMe-Arg-Gly-Asp-DPhe-Lys-(CO—(CH$_2$)$_5$—NH$_2$)) with HOOC—CH$_2$—O-polymer:
cyclo-(NMe-Arg-Gly-Asp-DPhe-Lys-(C0-(CH$_2$)$_5$—NH—CO—CH$_2$—O-polymer)).

Example 11

Biological Activities
i) Isolated Integrin-Ligand Binding Assay

The production of recombinant human integrin is known in the literature. The inhibitory activity of the substances given above are tested in a ligand inhibition assay, using immobilized integrin as the target, and biotinylated human serum vitronectin for a$_V$β$_3$ as ligand. In brief, 96-well ELISA plates are coated by adsorption from neutral aqueous buffers of 1 microg/ml integrin. After blocking residual sites on the plate with BSA, biotinylated ligands (1 microg/ml) are added in the presence or absence of serial dilutions of inhibitor, and after incubation and washing, bound biotin is detected with peroxidase-coupled anti-biotin antibody and TMB substrate. IC$_{50}$, the concentration of inhibitor needed to inhibit ligand binding in the absence of inhibitor by 50%, is established by curve fitting, and the values presented are usually the mean of three or more such independent determinations.
Cyclo-(Arg-Gly-Asp-DPhe-(NMe)Ala)=cyclo(RGDf(NMe)A):
IC$_{50}$ on integrin α$_V$β$_3$ is 24 nM
Cyclo-(Arg-Gly-Asp-DPhe-(NMe)Val)=cyclo(RGDf(NMe)V): IC$_{50}$ on integrin α$_V$β$_3$ is 3 nM
ii) Receptor Inhibition Assay Purified human integrin α$_V$β$_3$ from term placenta is adsorbed to microtitre wells and challenged with biotinylated complementary ligands—vitronectin (VN) for α$_V$β$_3$ in the presence of increasing amounts of test compounds.

Method: 1 µg ml$^{-1}$ biotin-ligand is incubated with 1 µg ml$^{-1}$ coated receptor in the presence of serially diluted peptides. After 3 h at 30° C. bound ligand was measures by anti-biotin—alkaline phosphatase detection.

Literature: Charo, I. F., Nannizzi, L., Smith, J. W. and Cheresh, D. A., J. Cell. Biol. 111, 2795-2800 (1990).

IC$_{50}$ values for binding of biotinylated ligands to human placental α$_V$β$_3$

| Sequence | IC$_{50}$ [nM] VN: α$_v$β$_3$ |
|---|---|
| Cyclo-(Arg-Gly-Asp-DPhe-Aib) | 20 |
| Cyclo-(Arg-Gly-Asp-DPhe-Acpa) | 9 |
| Cyclo-(Arg-Gly-Asp-DPhe-hPro) | 170 |
| Cyclo-(Arg-Gly-Asp-Phe-Nhdg) | 8 |
| Cyclo-(Arg-Gly-Asp-DPhe-Acha) | 2 |
| Cyclo-(Arg-Gly-Asp-DPhe-Tle) | 6 |
| Cyclo-(Arg-Gly-Asp-DPhe(4-Cl)-Tle) | 1.5 |
| Cyclo-(Arg-Gly-Asp-DPhe(4-F)-Tle) | 3 |
| Cyclo(Arg-Gly-Asp-Phe-Gly) | 400 | iii) Pentapeptides as Inhibitors of α$_V$β$_3$ (Immobilized)

Preparation and Characterization of Integrin α$_V$β$_3$: Integrin α$_V$β$_3$ is purified from human placental extracts by affinity chromatography on GRGDSPK peptide. Extraction and chromatography follows previously published protocols except that Triton X-100 is replaced by 25 mM octyl-P-D-glucopyranoside. Bound integrin is eluted with 10 mM EDTA into 1.5-ml vials containing 25 pl of 1 M MgCl, and concentrated in Centricon 100 microconcentrators. They are stored at 4° C. in neutral buffer containing 25 mM octyl glucoside, and 0.05% sodium azide. Protein concentrations were determined by a micro BCA assay (Pierce). The purified integrin is characterized by SDS-gel electrophoresis followed by protein staining and by immunoblotting, which demonstrates the purity and identity of the two subunits.

Solid-phase inhibition assays are established for the inhibition of binding of the vitronectin receptor a$_V$β$_3$ to their corresponding protein ligands by the cyclic peptides. Inhibitory activities (IC$_{50}$) of cyclic RGD containing peptides for the binding of vitronectin (VN). Integrins are used as immobilized ligands.

| Sequence | IC$_{50}$ [µM] VN: α$_v$β$_3$ |
|---|---|
| Cyclo-(DArg-Gly-Asp-Phe-Val) (=cyclo(rGDFV)) | 72 |
| Cyclo-(Arg-DAla-Asp-Phe-Val) (=cyclo(RaDFV)) | >240 |
| Cyclo-(Arg-Gly-DAsp-Phe-Val) (=cyclo(RGdFV)) | 152 |
| Cyclo-(Arg-Gly-Asp-DPhe-Val) (=cyclo(RGDfV)) | 0.049 |
| Cyclo-(Arg-Ala-Asp-DPhe-Val) (=cyclo(RADfV)) | 4 |
| Cyclo-(Arg-Gly-Asp-Phe-DVal) (=cyclo(RGDFv)) | 11 | iv) Integrin Inhibitor Characterisation

The biological activities of the following RGD peptides Cyclo-(Arg-Gly-Asp-DPhe-(NMe)Val), Cyclo-(Arg-Gly-Asp-DPhe-Val), Gly-Arg-Gly-Asp-Ser-Pro-Lys-OH and Cyclo-(Arg-Gly-Asp-DPhe-Acha) were compared in an isolated integrin binding assay as detailed elsewhere. Briefly, in receptor studies, recombinant human αvβ$_3$ integrin is adsorbed onto 96-well plates, and biotinylated human native ligand (plasma vitronectin) is added in the presence of serially diluted RGD peptides. After 3 hours at 37° C., bound ligand is detected using alkaline-phosphatase labelled anti-biotin MAbs (Sigma, St. Louis, Mo.).
Gly-Arg-Gly-Asp-Ser-Pro-Lys-OH: IC$_{50}$=120 nM
Cyclo-(Arg-Gly-Asp-DPhe-Val): IC$_{50}$=1.5 nM
Cyclo-(Arg-Gly-Asp-DPhe-(NMe)Val): IC$_{50}$=5.1 nM
Cyclo-(Arg-Gly-Asp-DPhe-Acha): IC$_{50}$=2.1 nM Example 12: cDNA-Microarray Studies cDNA-Microarray Studies The following is a study to determine the gene expression profiles of Cyclo-(Arg-Gly-Asp-DPhe-Acha) (=CPPC 1) treated human skin.

For the analysis of deregulated gene expression induced by substance CPPC 1, treated and control samples from a human skin model are analyzed as follows:

A full thickness skin model (human primary epidermal keratinocytes and human fibroblasts), such as the Phenion® FTSM, commercially available from Phenion GmbH & Co. KG, Düsseldorf, Germany, is used. Cells are not pooled or genetically modified.

Gene expression analysis is carried out with PIQOR™-skin cDNA microarrays, which contains 1312 genes that are involved in target pathways related to stress, inflammation, pigmentation and depigmentation, moisturization, anti-ageing and hair follicle development in humans. For instance, cell cycle, apoptosis, DNA repair, oxidative metabolism, angiogenesis, cell adhesion cell-matrix interactions and signaling. Genes are represented with four replicate spots.

Treatment with CPPC 1 is performed in 0.5 μM concentration (4 days incubation, n=3 per condition). Buffer-treated skin equivalents serve as controls.

Selection of genes is based on statistical methods (p<0.05, at least 1.5-fold deregulation).

345 deregulated genes are selected for 0.5 μM.

Profiling of Gene Expression—Input Genes

A ratio (log 2) value of zero indicates no regulation, whereas positive (log 2) values indicate an upregulation and negative (log 2) values a downregulation of the relevant gene.

The deregulated genes for skin samples treated with 0.5 μM concentration is used for further analysis.

06), extracellular matrix organization and biogenesis (p-value: 1.1147e-06), extracellular structure organization (p-value: 1.8748e-06), regulation of epithelial cell proliferation (p-value: 5.9339e-06) and cell-matrix adhesion (p-value: 1.3430e-05).

Example 1, Positive Regulation of Cell Proliferation

Positive regulation of cell proliferation is any process that activates or increases the rate or extent of cell proliferation.

The GO/biological process categories are over-representative under the up- and downregulated genes after treatment with the substance CPPC 1. Following up- and downregulated genes play an important role in positive regulation of cell proliferation (Table 1).

TABLE 1

Process: positive regulation of cell proliferation. Signal: the ratio as log2 value. Upregulated and downregulated genes.
Process(es) genes - Positive regulation of cell proliferation

| # | Gene Symbol | Protein | Protein name | Signal | P_value |
|---|---|---|---|---|---|
| 263 | TIMP1 | TIMP1_HUMAN | Metalloproteinase inhibitor 1 | 0.7312 | 0.0000029 |
| 138 | IL6 | IL6_HUMAN | Interleukin-6 | 0.4854 | 0.00013 |
| 208 | PTGS2 | PGH2_HUMAN | Prostaglandin G/H synthase 2 | 0.4222 | 0.021 |
| 256 | TGFB1 | TGFB1_HUMAN | Transforming growth factor beta-1 | 0.3674 | 0.014 |
| 85 | FGF7 | FGF7_HUMAN | Keratinocyte growth factor | 0.3561 | 0.0012 |
| 60 | DDR2 | DDR2_HUMAN | Discoidin domain-containing receptor 2 | 0.2869 | 0.0086 |
| 15 | BCL2L1 | BCLX_HUMAN | Apoptosis regulator Bcl-X | 0.263 | 0.017 |
| 20 | C19orf10 | CS010_HUMAN | UPF0556 protein C19orf10 | 0.263 | 0.0022 |
| 32 | CD81 | CD81_HUMAN | CD81 antigen | 0.251 | 0.002 |
| 39 | CDK2 | CDK2_HUMAN | Cell division protein kinase 2 | 0.2265 | 0.0046 |
| 200 | PGF | PLGF_HUMAN | Placenta growth factor | 0.2141 | 0.0058 |
| 40 | CDK4 | CDK4_HUMAN | Cell division protein kinase 4 | 0.1375 | 0.034 |
| 245 | STAT5B | STA5B_HUMAN | Signal transducer and activator of transcription 5B | −0.1844 | 0.011 |
| 71 | EGF | EGF_HUMAN | Pro-epidermal growth factor | −0.2345 | 0.044 |
| 269 | TNFSF13B | TN13B_HUMAN | Tumor necrosis factor ligand superfamily member 13B | −0.2688 | 0.0097 |
| 140 | IL7 | IL7_HUMAN | Interleukin-7 | −0.3585 | 0.0051 |
| 67 | E2F3 | E2F3_HUMAN | Transcription factor E2F3 | −0.3959 | 0.0031 |
| 148 | JUN | JUN_HUMAN | Transcription factor AP-1 | −0.5778 | 0.00000026 |

The experiment contains all up- and downregulated genes with the specified threshold.

Data Analysis

GeneGO's Metacore (Pathways and Maps) software.
Experiments Analyses, Automatically Calculated Using GeneGO Experiment analysis consists of matching gene IDs for the sets of the uploaded files with gene IDs in functional ontologies in MetaCore. The ontologies include canonical pathway maps, GeneGo cellular processes, GO cellular processes and diseases categories. The degree of "relevance" to different categories for the uploaded datasets is defined by p-values, so that the lower p-value gets higher priority.

Effects of CPPC 1 on Gene Expression Profile in Human Primary Epidermal Keratinocytes and Human Fibroblasts
Cellular Process The cDNA microarray analysis reveales top ranked cellular and molecular processes in our interest as follows: anatomical structure development (p-value: 1.1217e-20), response to external stimulus (p-value: 7.9497e-20), positive regulation of cell proliferation (p-value 1.8286e-10), response to wounding (p-value: 4.1539e-14), cell proliferation (p-value: 1.1825e-08), regulation of cell proliferation (p-value: 1.4041e-13), response to extracellular stimulus (p-value: 2.4436e-09), skin development (p-value: 1.5864e-

The Results of the Most Relevant Networks and Pathways Maps

The cDNA microarray analysis of treated skin with CPPC 1 results many deregulated genes related to cell organization and communication, also mediated by integrins. The most relevant network objects based on network analysis and pathways maps (the top scored networks and maps) are the cell adhesion cell-matrix interactions (p-value: 4.204e-18), integrin-mediated cell adhesion and migration (p-Value: 1.697e-07), cell adhesion extracellular matrix remodeling map (p-value: 4.076e-16). The adhesion of cells to the extracellular matrix (ECM) is a dynamic process, mediated by a series of matrix-associated and cell-surface molecules that interact with each other in a spatially and temporally regulated manner. These interactions play a major role in tissue formation, cellular migration and the induction of adhesion-mediated transmembrane signals.

The extra cellular matrix (ECM) is the extracellular part of tissue that usually provides structural support to the cells in addition to performing various important functions. Formation of the ECM is essential for processes like growth, wound healing, and fibrosis. The extracellular matrix is the defining feature of connective tissue. The ECM and cell adhesion and migration processes in fact plays at least three important roles relevant in cosmetics:

i) Mechanical: tensile and compressive strength and elasticity.
ii) Protection: buffering against extracellular change and retention of water.
iii) Organization: control of cell behavior by binding of growth factors and interaction will cell-surface receptors.

The ECM's main components are various glycoproteins like collagens, fibrin, elastin, fibronectins, laminins, and nidogens and other molecular compounds like proteoglycans and hyaluronic acid.

Results for Cosmetic Applications

The results of CPPC 1 in gene level gives insights into the potential action of the compound CPPC 1 as an integrin ligand in a variety of skin/hair regeneration, skin/hair care and/or disorders. Interactions with integrins and thus promotion of extracellular matrix proteins and a consecutive increased of matrix organization capacity, is believed to cause anti-wrinkle, anti-inflammation and promotion of hair growth in hair cycles and regarding to the hair follicle development.

Thus, the outcome of cDNA data analysis is listed in Table 2 and 3 and is divided in two categories in cosmetics applications as follows:
1. Anti-wrinkles/Anti-ageing and anti-inflammation,
2. Hair growth/re-growth—follicle development.

Examples, Description of a Couple of the Deregulated Genes Obtained after the Treatment of Skin with CPPC 1

S100 calcium binding protein A7, S100 calcium binding protein A8 and S100 calcium binding protein A9 (S100A7, S100A8 and S100A9) are downregulated genes after treatment of skin cells with CPPC 1.

S100A7A is believed to be involved in epidermal differentiation and inflammation and thus is believed to be important for the pathogenesis of psoriasis and other diseases. The S100A7 protein, also known as psoriasin, has important functions as a mediator and regulator in skin differentiation and disease (psoriasis), in breast cancer, and as a chemotactic factor for inflammatory cells (Kulski et al., Journal of Molecular Evolution (2003), 56(4), 397-406).

In addition, Lener et al. investigate genes involved in the natural aging process of the human skin. They found that in total 105 genes change their expression over 1.7-fold during the aging process in the human skin.

S100A7 and S100A9 have been described as genes upregulated in old skin (T. Lener et al., Experimental Gerontology 41 (2006), 387-397).

S100 proteins are the largest subgroup of $Ca^{2+}$ binding proteins with the EF-hand structural motif. A unique feature of this protein family is that individual members are localized in specific cellular compartments. For example, various S100 proteins are expressed in very restricted regions of the hair follicle (Kizawa K et al., Methods Mol Biol. (2005).

Extracellular proteases are crucial regulators of cell function. The family of matrix metalloproteinases (MMPs) has classically been described in the context of extracellular matrix (ECM) remodeling, which occurs throughout life in diverse processes that range from tissue morphogenesis to wound healing. Recent evidence has implicated MMPs in the regulation of other functions, including survival, angiogenesis, inflammation and signaling.

MMPs are secreted from keratinocytes and fibroblasts and break down collagen and other proteins that comprise the dermal extracellular matrix. Imperfect repair of the dermal damage impairs the functional and structural integrity of the extracellular matrix. Repeated sun exposure causes accumulation of dermal damage that eventually results in characteristic wrinkling of photodamaged skin (Gary J. Fisher et al., ARCH DERMATOL, vol. 138 (2002). In the skin, the primary role of MMP enzymes is to recycle skin matrix, particularly the structural proteins collagen and elastin. Reduces MMP activities degrade skin connective tissue and prevents loss of procollagen expression.

Decreasing the expression or activity of matrix metalloproteases has an effect on the biological collagen catabolic process towards skin treatment of aging and psoriasis.

The downregulated MMP genes after treatment of skin cells with CPPC 1 are MMP7, 13, 16, 23, 25. It is likely that downregulation of MMPs results in increase of collagen fibrils. Also laminin-alpha3, laminin-alpha4, lamninin-beta1, laminin-gamma1, collagen-alpha I (XV), collagen-alpha I (IV), and collagen-alpha II(IV) are significantly upregulated.

Laminin is thought to mediate the attachment, migration, and organization of cells into tissues during embryonic development by interacting with other extracellular matrix components.

Tissue inhibitor of metalloproteinases (TIMP-1) is strongly up-regulated after treatment of skin cells with CPPC 1. TIMP1 has been described as a cell survival factor. TIMP-1 is one representative of the natural MMP inhibitor family, encompassing four members. Its expression is decreased with fibroblast senescence, both ex vivo and in vivo, thus contributing to increased catabolic activity within dermis. TIMP-1 displays multiple biological functions. It inhibits most MMPs. Thus, CPPC 1 activates upregulation dermal fibroblast collagen production and downregulation of collagen degradation.

Integrin-mediated cell adhesion and signaling events are essential for the proper development and homeostasis of most epithelial tissues.

Ultraviolet (UV) irradiation from the sun reduces production of type I procollagen (COLI), the major structural protein in human skin. Photo-aging is the most common form of skin damage and is associated with skin carcinoma. UV irradiation inhibits TGF-beta1-induced type I procollagen gene expression in cultured human skin fibroblasts (Quan et al., AJP (2004), 165, No. 3, 741-751). TGF-beta is multifunctional protein that control proliferation, differentiation, and other functions in many cell types. TGF-beta/Smad pathway is the major regulator of type I procollagen synthesis in human skin.

In the present gene expression experiment, TGF-beta1, TGF-beta3, and LTBP1 (latent TGF-beta binding protein) genes are upregulated after treatment of skin cells with CPPC 1.

LTBP1 is one of the naturally occurring RGD ligands for αv-integrins. Its role in activation and release of active TGF-beta has been described (Sheppard, Cancer and Metastasis Reviews 24 (2005), 395-402).

Also, CTGF (connective tissue growth factor) is produced by skin fibroblasts after activation with TGF-beta.

In addition, superoxide dismutase (SOD2), which catalyzes the dismution of superoxide into oxygen and hydrogen peroxide, is significantly upregulated. SOD is an important anti-oxidant defense in nearly all cells exposed to oxygen (skin/hair).

Integrins are heterodimeric adhesion receptors composed of an alpha and beta subunits. Most integrins recognize several proteins of ECM, including laminin, fibronectin, and collagen (types I, II, and IV), elastin, fibulin, osteonectin, hyaluronic acid, and nidogen (Lee J W et al., Molecules and Cells (2004), 17(2):188-202). CPPC 1 is a highly active av-beta3/5 ligand and low active av-beta6 ligand (in vitro studies).

It promotes cell proliferation, cell adhesion and extracellular structure organization by outcoming of cDNA microarray data and the published references.

In skin and hair follicle biology, beta1 integrins and their ligands are of particular interest (Kloepper, J. E. Experimental Cell Research (2008). Integrin beta1 (ITGB1) shows a significant upregulation in our study.

Integrin alpha5 and alpha3 (fibronectin receptor alpha, ITGA5 and ITGA3) are also upregulated in the skin treated by CPPC 1. It is known that integrin alpha5/beta1 mediates fibronectin-induced epithelial cell proliferation through activation of the EGFR. Fibronectins are proteins that connect cells with collagen fibers in the ECM, allowing cells to move through the ECM.

TGF-beta superfamily of signaling molecules are involved in the regulation of many developmental processes that contain the interaction between mesenchymal and epithelial tissues. Smad7 is a potent inhibitor of many members of the TGF-beta family, notably TGF-beta and activin. Klopcic B et al. has reported that TGF-beta superfamily signaling is essential for development of hair, tooth, and T-cells as well as differentiation and proliferation control in adult tissues (Eur J, Cell Biol. (2007), 86(11-12):781-99).

It is known that the inhibition of BMP signaling affects growth and differentiation in the anagen hair follicle. BMP stimulate differentiation of epidermal and hair follicle keratinocytes, inhibit initiation of hair growth, promote melanocyte proliferation and modulate melanogenesis, as well as an increase in calcitonin gene-related peptide expression in sensory neurons innervating skin. Downregulation of BMP-2 retards the entry in catagen phase in hair follicle cycling. Inhibition of BMP signaling also results in the generation of new intestinal stem cell proliferation (noggin is the natural inhibitor of BMP signaling—L. M. Hogan et al., The EMBO Journal (2000)).

BMP-2 suppresses proliferative activity and support diffentiation, while FGF-7 (fibroblast growth factor-7) induces anagen phase of hair follicle growth (Paus R., Physiol Rev (2001), 81:449-494).

In the treated skin with CPPC 1, BMP-1, -2, -3, -7, and -10 are downregulated, while FGF-7 is significantly upregulated.

Treatment with FGF-7 at concentrations of 10 ng/ml or greater significantly stimulates hair fiber elongation in human scalp hair follicle organ cultures (Iino M et al., Journal of Investigative Dermatology (2007)). Thus, stimulating of fibroblast growth factor-7 gene expression is believed stimulate hair growth.

Fibulin-1 and -2 are extracellular matrix proteins, which belongs to the RGD class of proteins with unique structural features. A locally restricted expression pattern of fibulin-1 and fibulin-2 mRNA and protein at sites of epithelial-mesenchymal interactions was detected in two tissues, the developing tooth and hair follicles (Hang H Y et al., Dev Dyn (1996), 205(3):348-64).

CPPC 1 is believed to bind at the integrin RGD site like fibulin and thus is believed promote the upregulation of fibulin and other extracellular matrix-RGD-proteins like fibronectin, procollagen, laminin, etc.

DNA topoisomerase (TOP) are a family of enzymes that are involved in DNA replication and metabolism. The enzymes tie or untie DNA knots so that the DNA can replicate effectively. They regulate the helical structure of the double-stranded DNA by breaking one (topoisomerase type I) or both (topoisomerase type II) strands of the DNA helix (Wang J., Adv. Pharmacol. (1994), 29A:1-19). TOP-2 belongs to the genes, which are downregulated in the human anagen hair follicle bulge (Manabu Ohyama et al., J. Clin. Invest. (2006), 116:249-260). Hair loss is known as the side effect of topoismerase inhibitors.

From the gene expression analysis and due to the literature (Ludbrook S B et al., Biochemical Journal (2003)), it is known that integrins regulates TGF superfamily signaling, in our study both, TGF-beta1 and TGF-beta3 are upregulated. TGF-beta1 and -beta3 is believed to lead via different transcription factors (SP1, SMADs, AP-1, Wnt, SR1, OASIS, etc.) to the regulation of targets like bone morphogenic proteins (BMPs: downregulated), nidogen (NID: upregulated), fibulins (upregulated), antigen Ki-67 (upregulated), and TOP2A (upregulated). In addition TGF-beta/BMP signaling pathway is known for the regulation of hair follicle development and cycling (Kobielak, K. et al., J. Cell Biol. (2003), 163:609-623)

APPENDIX, TABLE 2 AND 3

TABLE 2

Anti-ageing and anti-inflammation related deregulated genes by treated skin with CPPC 1.

| Gene ID | Gene-Name | UniProt | RefSeq | Compound vs. Control, ratio Log(2) value | P-value |
|---|---|---|---|---|---|
| 5 | IL2 | P60568 P01585 Q13169 | NM_000586 | −0.577766999 | 0.051 |
| 16 | IL7 | P13232 | NM_000880 | −0.358453971 | 0.0051 |
| 32 | TXLN | Q66K62 Q86T54 Q86T85 Q86T86 Q86Y86 Q86YW3 P40222 Q8N2Y3 | NM_175852 | −0.836501268 | 0.049 |
| 37 | IL17A | Q16552 | NM_002190 | −0.666576266 | 0.00097 |
| 41 | TNF | P01375 O43647 Q9P1Q2 Q9UIV3 | NM_000594 | −0.304006187 | 0.06 |
| 83 | TNFSF13B | Q9Y275 | NM_006573 | −0.268816758 | 0.0097 |
| 99 | TNFSF10 | P50591 | NM_003810 | −0.268816758 | 0.012 |
| 105 | TNFRSF25 | Q93038 Q93036 Q93037 Q92983 P78515 Q99831 Q99722 P78507 Q99830 O | NM_003790 NM_148965 NM_148966 NM_148967 NM_148970 | −0.268816758 | 0.00065 |

TABLE 2-continued

Anti-ageing and anti-inflammation related deregulated genes by treated skin with CPPC 1.

| Gene ID | Gene-Name | UniProt | RefSeq | Compound vs. Control, ratio Log(2) value | P-value |
|---|---|---|---|---|---|
| 251 | TNFRSF1B | P20333 Q6YI29 Q16042 Q9UIH1 | NM_001066 | −0.358453971 | 0.036 |
| 2344 | TIMP1 | P01033 Q14252 Q9UCU1 | NM_003254 | 0.731183242 | 0.0000029 |
| 4085 | SOCS1 | O15524 O15097 Q9NSA7 | NM_003745 | 0.333423734 | 0.000095 |
| 7972 | S100A8 | P05109 Q9UC92 Q9UCJ0 | NM_002964 | −0.49410907 | 0.000037 |
| 7975 | S100A9 | P06702 Q9NYM0 Q9UCJ1 | NM_002965 | −0.415037499 | 0.0000036 |
| 9156 | S100A7 | P31151 Q9H1E2 | NM_002963 | −0.514573173 | 0.00004 |
| 37885 | TNFC | Q06643 P78370 Q99761 | NM_002341 NM_009588 | −0.340075442 | 0.02 |
| 18 | IL8 | Q9C077 P10145 Q6FGF6 Q6LAE6 Q96RG6 | NM_000584 | 0.321928095 | 0.019 |
| 55 | TUBB | P07437 | NM_178014 | 0.659924558 | 0.0005 |
| 499 | ITGB1 | P05556 P78466 P78467 Q13089 Q14647 Q13090 Q13212 Q13091 Q14622 | NM_002211 NM_033666 NM_033667 NM_033668 NM_033669 NM_133376 | 0.378511623 | 0.0014 |
| 552 | ITGA3 | P26006 | NM_002204 NM_005501 | 0.344828497 | 0.0013 |
| 556 | ITGA5 | P08648 Q96HA5 | NM_002205 | 0.378511623 | 0.000067 |
| 1221 | KI67 | P46013 Q5VWH2 | NM_002417 | 0.310340121 | 0.011 |
| 2275 | COL15A1 | P39059 Q5T6J4 Q9Y4W4 | NM_001855 | 0.367371066 | 0.011 |
| 2289 | COL4A1 | P02462 Q9NYC5 | NM_001845 | 0.50589093 | 0.0000005 |
| 2305 | COL4A2 | P08572 | NM_001846 | 0.321928095 | 0.00022 |
| 2344 | TIMP1 | P01033 Q14252 Q9UCU1 | NM_003254 | 0.731183242 | 0.0000029 |
| 2364 | LAMA3 | Q96TG0 Q16787 Q13679 Q13680 | NM_000227 NM_198129 | 0.298658316 | 0.045 |
| 2366 | LAMA4 | Q9UE18 Q9UJN9 Q16363 Q15335 Q14735 Q14731 Q4LE44 Q5SZG8 | NM_002290 | 0.604071324 | 0.00000058 |
| 2370 | LAMB1 | P07942 | NM_002291 | 0.321928095 | 0.0036 |
| 2377 | LAMG1 | P11047 | NM_002293 | 0.321928095 | 0.00007 |
| 2493 | MMP13 | P45452 | NM_002427 | −0.473931188 | 0.0089 |
| 2505 | MMP7 | P09237 Q9BTK9 | NM_002423 | −0.395928676 | 0.001 |
| 2533 | SPARC | P09486 | NM_003118 | 0.367371066 | 0.025 |
| 4749 | ELA2 | P08246 P09649 Q6B0D9 Q6LDP5 | NM_001972 | −0.234465254 | 0.073 |
| 5239 | MMP23A-MMP23B | Q9UBR9 O75900 O75894 O75895 Q5QPQ8 Q76P96 Q7LDM6 Q7LDM7 Q9UJK8 O | NM_006983 NR_002946 | −0.64385619 | 0.00000059 |
| 6926 | LCN2 | P80188 P30150 Q92683 | NM_005564 | −0.556393349 | 0.0000004 |
| 7972 | S100A8 | P05109 Q9UC92 Q9UCJ0 | NM_002964 | −0.49410907 | 0.000037 |
| 7975 | S100A9 | P06702 Q9NYM0 Q9UCJ1 | NM_002965 | −0.415037499 | 0.0000036 |
| 9156 | S100A7 | P31151 Q9H1E2 | NM_002963 | −0.514573173 | 0.00004 |
| 11207 | KRT9 | P35527 O00109 Q14665 | NM_000226 | −0.268816758 | 0.012 |
| 20743 | MMP25 | Q9NPA2 Q9H3Q0 | NM_022468 NM_022718 | −0.268816758 | 0.093 |
| 30439 | TGFB1 | P01137 Q9UCG4 | NM_000660 | 0.367371066 | 0.014 |
| 30442 | TGFB3 | P10600 | NM_003239 | 0.321928095 | 0.027 |
| 35735 | MMP16_2 | P51512 Q14824 Q52H48 | NM_022564 | −0.340075442 | 0.036 |
| 38095 | SPRR1A | P35321 Q9UDG4 | NM_005987 | −0.304006187 | 0.00069 |
| 38182 | SOD2 | P04179 P78434 Q16792 Q96EE6 Q9P2Z3 Q5TCM1 | NM_000636 NM_001024465 NM_001024466 | 0.298658316 | 0.005 |

TABLE 3

Hair relevant deregulated genes by treated skin with CPPC 1

| Gene ID | Gene-Name | UniProt | RefSeq | Compound vs. Control, ratio Log(2) value | P-value |
|---|---|---|---|---|---|
| 2356 | BMP7 | Q9NTQ7 Q9H512 P18075 | NM_001719 | −0.888968688 | 0.0019 |
| 9302 | BMP10 | O95393 | NM_014482 | −0.415037499 | 0.015 |
| 38095 | SPRR1A | P35321 Q9UDG4 | NM_005987 | −0.304006187 | 0.00069 |
| 3151 | ASC | Q9HBD0 Q9NXJ8 Q9BSZ5 Q9ULZ3 Q96D12 | NM_145183 | −0.304006187 | 0.012 |
| 35633 | CASP8 | Q14790 O14676 Q14791 Q14792 Q14793 Q14794 Q14795 Q14796 Q15780 Q | NM_001228 NM_033355 NM_033356 NM_033358 | −0.304006187 | 0.016 |
| 2104 | GDF10 | Q9UCX6 P55107 | NM_004962 | −0.286304185 | 0.044 |
| 7969 | S100A12 | P80511 P83219 | NM_005621 | −0.251538767 | 0.019 |
| 1282 | BMP2 | P12643 | NM_001200 | −0.251538767 | 0.0072 |
| 35624 | BMP1_2 | P13497 Q13292 Q13872 Q14874 Q99421 Q99422 Q99423 Q9UL38 P46721 Q | NM_001199 NM_006128 NM_006129 | −0.234465254 | 0.098 |
| 1221 | KI67 | P46013 Q5VWH2 | NM_002417 | 0.310340121 | 0.011 |
| 4091 | STAT1 | P42224 | NM_007315 NM_139266 | 0.310340121 | 0.0014 |
| 30442 | TGFB3 | P10600 | NM_003239 | 0.321928095 | 0.027 |
| 11184 | KRT19 | P08727 Q5XG83 Q6NW33 Q7L5M9 Q96A53 Q96FV1 Q9BYF9 Q9P1Y4 | NM_002276 | 0.333423734 | 0.032 |
| 552 | ITGA3 | P26006 | NM_002204 NM_005501 | 0.344828497 | 0.0013 |
| 5203 | FGF7 | P21781 | NM_002009 | 0.35614381 | 0.0012 |
| 30439 | TGFB1 | P01137 Q9UCG4 | NM_000660 | 0.367371066 | 0.014 |
| 281 | MCL1 | Q07820 Q9UNJ1 Q9NRQ3 Q9NRQ4 Q9HD91 Q9UHR7 Q9UHR8 Q9UHR9 | NM_021960 NM_182763 | 0.367371066 | 0.0069 |
| 2533 | SPARC | P09486 | NM_003118 | 0.367371066 | 0.025 |
| 499 | ITGB1 | P05556 P78466 P78467 Q13089 Q14647 Q13090 Q13212 Q13091 Q14622 | NM_002211 NM_033666 NM_033667 NM_033668 NM_033669 NM_133376 | 0.378511623 | 0.0014 |
| 556 | ITGA5 | P08648 Q96HA5 | NM_002205 | 0.378511623 | 0.000067 |
| 2457 | FBLN2 | P98095 | NM_001004019 NM_001998 | 0.378511623 | 0.00029 |
| 1613 | SDCBP | O00173 O00560 O43391 | NM_005625 | 0.389566812 | 0.000026 |
| 11190 | KRT2A | P35908 | NM_000423 | 0.40053793 | 0.072 |
| 2437 | QSOX1 | O00391 Q13876 Q59G29 Q5T2X0 Q8WVP4 Q8TDL6 | NM_001004128 NM_002826 | 0.432959407 | 0.0015 |
| 7586 | CLU | P10909 P11380 P11381 Q7Z5B9 | NM_001831 NM_203339 | 0.443606651 | 0.0048 |
| 11154 | FLOT2 | Q14254 | NM_004475 | 0.454175893 | 0.0052 |
| 118 | CCNB2 | O95067 | NM_004701 | 0.464668267 | 0.000027 |
| 2515 | NIDOGEN: (NID) | P14543 Q14942 Q59FL2 Q5TAF2 Q5TAF3 Q86XD7 | NM_002508 | 0.475084883 | 0.000093 |
| 2483 | ADAM9 | Q8NFM6 Q10718 Q13443 | NM_001005845 NM_003816 | 0.485426827 | 0.0051 |
| 17158 | IGFBP4 | P22692 | NM_001552 | 0.485426827 | 0.00089 |
| 5177 | FGF1 | P05230 P07502 | NM_000800 NM_033136 NM_033137 | 0.50589093 | 0.0016 |
| 21796 | FBLN1_4 | Q8TBH8 Q9HBQ5 Q9UH41 P23142 P23143 P23144 P37888 Q9UGR4 Q5TIC4 Q | NM_001996 NM_006485 NM_006486 NM_006487 | 0.516015147 | 0.000016 |
| 10509 | SEPRASE | Q12884 O00199 Q86Z29 Q99998 Q9UID4 | NM_004460 | 0.545968369 | 0.00000071 |

TABLE 3-continued

Hair relevant deregulated genes by treated skin with CPPC 1

| Gene ID | Gene-Name | UniProt | RefSeq | Compound vs. Control, ratio Log(2) value | P-value |
|---|---|---|---|---|---|
| 2465 | LTBP1 | P22064 Q14766 Q8TD95 | NM_000627 NM_206943 | 0.555816155 | 0.000065 |
| 9410 | TOP2A | Q9UP44 Q9UQP9 P11388 Q9HB24 Q9HB25 Q9HB26 Q71UN1 Q71UQ5 | NM_001067 | 0.622930351 | 0.000024 |

Example 13: Compositions

Formulations for compositions, preferably preferably non-therapeutic compositions, cosmetic compositions and/or topical compositions, comprising compounds selected from the cyclic peptides according to the invention are shown by way of example below. The INCI names of the commercially available compounds are also shown.

UV-Pearl, OMC stands for the composition having the INCI name: Water (for EU: Aqua), Ethylhexyl Methoxycinnamate, Silica, PVP, Chlorphenesin, BHT; this composition is commercially available under the name Eusolex®UV Pearl™ OMC from Merck KGaA, Darmstadt.

The other UV Pearl products indicated in the tables are each of analogous composition with OMC replaced by the UV filter indicated.

TABLE 1a

W/O emulsions (data in % by weight)

| | 1-1 | 1-2 | 1-3 | 1-4 | 1-5 | 1-6 | 1-7 | 1-8 | 1-9 | 1-10 |
|---|---|---|---|---|---|---|---|---|---|---|
| Titanium Dioxide | | 2 | 5 | | | | | | | 3 |
| Cyclo-(Arg-Gly-Asp-DPhe-Acha) | 0.01 | 0.005 | 0.001 | 0.0005 | 0.005 | | | | 0.005 | 0.005 |
| Cyclo-(Arg-Gly-Asp-DPhe-(NMe)Val) | | | | | | 0.0005 | 0.01 | 0.005 | | |
| Zinc Oxide | | | | | | | | | 5 | 2 |
| UV-Pearl, OMC | 30 | 15 | 15 | 15 | 15 | 15 | 15 | 15 | 15 | 15 |
| Polyglyceryl-3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

TABLE 1b

| | 1-11 | 1-12 | 1-13 | 1-14 | 1-15 | 1-16 | 1-17 | 1-18 |
|---|---|---|---|---|---|---|---|---|
| Titanium Dioxide | 3 | | 2 | | 3 | | 2 | 5 |
| Benzylidene Malonate Polysiloxane | | 1 | | | | | 0.5 | |
| Methylene Bis-benzotriazolyl Tetramethylbutylphenol | 1 | 1 | | | | | 0.5 | |
| Cyclo-(Arg-Gly-Asp-DPhe-Acha) | 0.01 | 0.005 | 0.001 | 0.0005 | 0.005 | | | |
| Cyclo-(Arg-Gly-Asp-DPhe-(NMe)Val) | | | | | | 0.0005 | 0.01 | 0.005 |
| Polyglyceryl-3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |

TABLE 1b-continued

|  | 1-11 | 1-12 | 1-13 | 1-14 | 1-15 | 1-16 | 1-17 | 1-18 |
|---|---|---|---|---|---|---|---|---|
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate |  |  |  |  | 6 | 6 | 6 | 6 |
| PEG-7 Hydrogenated Castor Oil |  |  |  |  | 1 | 1 | 1 | 1 |
| Zinc Stearate |  |  |  |  | 2 | 2 | 2 | 2 |
| Oleyl Erucate |  |  |  |  | 6 | 6 | 6 | 6 |
| Decyl Oleate |  |  |  |  | 6 | 6 | 6 | 6 |
| Dimethicone |  |  |  |  | 5 | 5 | 5 | 5 |
| Tromethamine |  |  |  |  | 1 | 1 | 1 | 1 |
| Glycerine |  |  |  |  | 5 | 5 | 5 | 5 |
| Allantoin |  |  |  |  | 0.2 | 0.2 | 0.2 | 0.2 |
| Water | to 100 | to 100 | to 100 | to 100 | to 100 | to 100 | to 100 | to 100 |

TABLE 1c

|  | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium Dioxide |  | 2 | 5 |  |  |  |  |  |  | 3 | 3 |
| Benzylidene Malonate Polysiloxane |  |  |  | 1 |  |  |  |  | 1 | 1 |  |
| Cyclo-(Arg-Gly-Asp-DPhe-Acha) | 0.01 | 0.005 | 0.001 | 0.0005 | 0.005 |  |  |  | 0.005 | 0.001 | 0.0005 |
| Cyclo-(Arg-Gly-Asp-DPhe-(NMe)Val) |  |  |  |  |  | 0.0005 | 0.01 | 0.005 |  |  |  |
| Zinc Oxide |  |  |  |  |  |  | 5 | 2 |  |  |  |
| UV-Pearl, OCR |  | 10 |  |  |  |  |  |  |  |  | 5 |
| UV-Pearl, EthylhexylDimethylPABA |  |  | 10 |  |  |  |  |  |  |  |  |
| UV-Pearl, Homosalate |  |  |  | 10 |  |  |  |  |  |  |  |
| UV-Pearl, Ethylhexyl Salicylate |  |  |  |  | 10 |  |  |  |  |  |  |
| UV-Pearl, OMC. BP-3 |  |  |  |  |  | 10 |  |  |  |  |  |
| UV-Pearl, OCR. BP-3 |  |  |  |  |  |  | 10 |  |  |  |  |
| UV-Pearl, Ethylhexyl Dimethyl PABA, BP-3 |  |  |  |  |  |  |  | 10 |  |  |  |
| UV-Pearl, Homosalate, BP-3 |  |  |  |  |  |  |  |  | 10 |  |  |
| UV-Pearl, Ethylhexyl Salicylate, BP-3 |  |  |  |  |  |  |  |  |  | 10 |  |
| BMDBM |  |  |  |  |  |  |  |  |  |  | 2 |
| UV-Pearl, OMC, 4-Methylbenzylidene Camphor | 25 |  |  |  |  |  |  |  |  |  |  |
| Polyglyceryl-3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 | 0.15 |
| Water |  |  |  |  |  | to 100 |  |  |  |  |  |

TABLE 2a

| O/W emulsions, data in % by weight | | | | | | | | | | |
|---|---|---|---|---|---|---|---|---|---|---|
|  | 2-1 | 2-2 | 2-3 | 2-4 | 2-5 | 2-6 | 2-7 | 2-8 | 2-9 | 2-10 |
| Titanium Dioxide |  | 2 | 5 |  |  |  |  |  |  | 3 |
| Methylene Bis-benzotriazolyl Tetramethylbutylphenol |  |  |  | 1 |  |  | 2 | 1 |  |  |
| Cyclo-(Arg-Gly-Asp-DPhe-Acha) | 0.01 | 0.005 | 0.001 | 0.0005 | 0.005 |  |  |  | 0.005 | 0.001 |
| Cyclo-(Arg-Gly-Asp-DPhe-(NMe)Val) |  |  |  |  |  | 0.0005 | 0.01 | 0.005 |  |  |
| Ectoine |  | 1 |  | 3 |  | 5 |  | 1 |  | 2 |
| 4-Methylbenzylidene Camphor | 2 |  | 3 |  | 4 |  | 3 |  | 2 |  |
| BMDBM | 1 | 3 |  | 3 | 3 |  | 3 | 3 | 3 |  |

TABLE 2a-continued

O/W emulsions, data in % by weight

|  | 2-1 | 2-2 | 2-3 | 2-4 | 2-5 | 2-6 | 2-7 | 2-8 | 2-9 | 2-10 |
|---|---|---|---|---|---|---|---|---|---|---|
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE |  |  |  |  |  |  |  |  |  |  |
| Stearic Acid |  |  |  |  |  |  |  |  |  |  |
| *Persea Gratissima* |  |  |  |  |  |  |  |  |  |  |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine |  |  | 1.8 |  |  |  |  |  |  |  |
| Glycerine |  |  |  |  |  |  |  |  |  |  |
| Water | to 100 | to 100 | to 100 | to 100 | to 100 | to 100 | to 100 | to 100 | to 100 | to 100 |

TABLE 2b

|  | 2-11 | 2-12 | 2-13 | 2-14 | 2-15 | 2-16 | 2-17 | 2-18 |
|---|---|---|---|---|---|---|---|---|
| Titanium Dioxide | 3 |  | 2 |  |  |  | 2 | 5 |
| Benzylidene Malonate Polysiloxane |  | 1 | 0.5 |  |  |  |  |  |
| Cyclo-(Arg-Gly-Asp-DPhe-Acha) | 0.01 | 0.005 | 0.001 | 0.0005 | 0.005 |  |  |  |
| Cyclo-(Arg-Gly-Asp-DPhe-(NMe)Val) |  |  |  |  |  | 0.0005 | 0.01 | 0.005 |
| Ectoine | 0.5 |  | 1 |  | 3 |  | 1 |  |
| Zinc Oxide |  |  | 2 |  |  |  |  |  |
| UV-Pearl, OMC | 15 | 15 | 15 | 30 | 30 | 30 | 15 | 15 |
| 4-Methylbenzylidene Camphor |  |  |  | 3 |  |  |  |  |
| BMDBM |  |  |  | 1 |  |  |  |  |
| Phenylbenzimidazole Sulfonic Acid |  |  |  |  | 4 |  |  |  |
| Stearyl Alcohol (and) Steareth-7 (and) Steareth-10 | 3 | 3 | 3 | 3 |  |  |  |  |
| Glyceryl Stearate (and) Ceteth-20 | 3 | 3 | 3 | 3 |  |  |  |  |
| Glyceryl Stearate | 3 | 3 | 3 | 3 |  |  |  |  |
| Microwax | 1 | 1 | 1 | 1 |  |  |  |  |
| Cetearyl Octanoate | 11.5 | 11.5 | 11.5 | 11.5 |  |  |  |  |
| Caprylic/Capric Triglyceride | 6 | 6 | 6 | 6 | 14 | 14 | 14 | 14 |
| Oleyl Oleate | 6 | 6 | 6 | 6 |  |  |  |  |
| Propylene Glycol | 4 | 4 | 4 | 4 |  |  |  |  |
| Glyceryl Stearate SE |  |  |  |  | 6 | 6 | 6 | 6 |
| Stearic Acid |  |  |  |  | 2 | 2 | 2 | 2 |
| *Persea Gratissima* |  |  |  |  | 8 | 8 | 8 | 8 |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Tromethamine |  |  |  |  | 1.8 |  |  |  |
| Glycerine |  |  |  |  | 3 | 3 | 3 | 3 |
| Water | to 100 | to 100 | to 100 | to 100 | to 100 | to 100 | to 100 | to 100 |

TABLE 2c

|  | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium Dioxide |  |  |  |  |  |  | 3 | 3 |  | 2 |
| Cyclo-(Arg-Gly-Asp-DPhe-Acha) | 0.01 | 0.005 | 0.001 | 0.0005 | 0.005 |  |  |  | 0.005 | 0.001 |
| Cyclo-(Arg-Gly-Asp-DPhe-(NMe)Val) |  |  |  |  |  | 0.0005 | 0.01 | 0.005 |  |  |
| Zinc Oxide |  |  |  |  | 5 | 2 |  |  |  | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate |  |  |  |  |  |  |  |  |  |  |
| Propylene Glycol |  |  |  |  |  |  |  |  |  |  |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| *Persea Gratissima* | 8 | 8 | 8 | 8 | 8 | 8 | 8 | 8 | 8 | 8 |

TABLE 2c-continued

|  | 2-19 | 2-20 | 2-21 | 2-22 | 2-23 | 2-24 | 2-25 | 2-26 | 2-27 | 2-28 |
|---|---|---|---|---|---|---|---|---|---|---|
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Glyceryl Stearate. Ceteareth-20. Ceteareth-10. Cetearyl Alcohol. Cetyl Palmitate | | | | | | | | | | |
| Ceteareth-30 | | | | | | | | | | |
| Dicaprylyl Ether | | | | | | | | | | |
| Hexyldecanol, Hexyldexyl Laurate | | | | | | | | | | |
| Cocoglycerides | | | | | | | | | | |
| Tromethamine | | | | | | | | | | |
| Glycerine | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

Gels, data in % by weight

|  | 3-1 | 3-2 | 3-3 | 3-4 | 3-5 | 3-6 | 3-7 | 3-8 | 3-9 | 3-10 |
|---|---|---|---|---|---|---|---|---|---|---|
| Titanium Dioxide | | 2 | 5 | | | | | | | 3 |
| Cyclo-(Arg-Gly-Asp-DPhe-Acha) | 0.01 | 0.005 | 0.001 | 0.0005 | 0.005 | | | | 0.005 | 0.001 |
| Cyclo-(Arg-Gly-Asp-DPhe-(NMe)Val) | | | | | | 0.0005 | 0.01 | 0.005 | | |
| Benzylidene Malonate Polysiloxane | | | 1 | 1 | 2 | | | | 1 | 1 |
| Methylene Bis-benzotriazolyl Tetramethylbutylphenol | | 1 | | | | 1 | 2 | 1 | | |
| Zinc Oxide | | | | 2 | | | | | 5 | 2 |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | | 2 | | | | |
| Butylmethoxydibenzoylmethane | | 1 | | | | | | | | |
| Phenylbenzimidazole Sulfonic Acid | | | | 4 | | | | | | |
| *Prunus Dulcis* | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 | a = aqueous gel

TABLE 2d

O/W emulsions, data in % by weight

|  | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium dioxide | | | | | | | 3 | 3 | | 2 |
| Cyclo-(Arg-Gly-Asp-DPhe-Acha) | 0.01 | 0.005 | 0.001 | 0.0005 | 0.005 | | | | 0.005 | 0.001 |
| Cyclo-(Arg-Gly-Asp-DPhe-(NMe)Val) | | | | | | 0.0005 | 0.01 | 0.005 | | |
| Ectoine | | 1 | | 3 | | 5 | | 1 | | 2 |
| Methylene Bis-Benztriazolyl Tetramethylbutylphenol | | | 1 | 2 | 1 | | | 1 | 1 | 0.5 |
| Zinc oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate | | | | | | | | | | |
| Propylene Glycol | | | | | | | | | | |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| *Persea Gratissima* | 8 | 8 | 8 | 8 | 8 | 8 | 8 | 8 | 8 | 8 |

TABLE 2d-continued

O/W emulsions, data in % by weight

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | | | | | | | | | | |
| Ceteareth-30 | | | | | | | | | | |
| Dicaprylyl Ether | | | | | | | | | | |
| Hexyldecanol, Hexyldexyllaurate | | | | | | | | | | |
| Cocoglycerides | | | | | | | | | | |
| Tromethamine | | | | | | | | | | |
| Glycerin | 3 | 3 | 3 | 3 | 3 | 3 | 3 | 3 | 3 | 3 |
| Water | ad 100 | ad 100 | ad 100 | ad 100 | ad 100 | ad 100 | ad 100 | ad 100 | ad 100 | ad 100 |

TABLE 3

Gels, data in % by weight

| | 3-1 | 3-2 | 3-3 | 3-4 | 3-5 | 3-6 | 3-7 | 3-8 | 3-9 | 3-10 |
|---|---|---|---|---|---|---|---|---|---|---|
| Titanium dioxide | | 2 | 5 | | | | | | | 3 |
| Cyclo-(Arg-Gly-Asp-DPhe-Acha) | 0.01 | 0.005 | 0.001 | 0.0005 | 0.005 | | | | 0.005 | 0.001 |
| Cyclo-(Arg-Gly-Asp-DPhe-(NMe)Val) | | | | | | 0.0005 | 0.01 | 0.005 | | |
| Benzylidene malonate polysiloxane | | | 1 | 1 | 2 | | | | 1 | 1 |
| Methylene Bis-Benztriazolyl Tetramethylbutylphenol | | 1 | | | | 1 | 2 | 1 | | |
| Zinc oxide | | | | 2 | | | 5 | 2 | | |
| UV-Pearl, Ethylhexyl Mehtoxycinnamat | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | | 4 | | | | | | |
| *Prunus Dulcis* | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | ad 100 | ad 100 | ad 100 | ad 100 | ad 100 | ad 100 | ad 100 | ad 100 | ad 100 | ad 100 | a = aqueous gel

Example 14: Anti-Cellulite Compositions

| Components | % |
|---|---|
| Composition 1 | |
| *Phase A* | |
| Cetyl alcohol | 2 |
| Glyceryl Stearate | 5 |
| Caprylic/Capric Triglyceride | 8 |
| Isopropyl Palmitate | 9 |
| *Phase B* | |
| Glycerol | 3 |
| Preservatives (Germaben II) | 0.8 |
| Cyclo-(Arg-Gly-Asp-DPhe-Acha) | 0.005 |
| Water, demineralised | ad 100 |
| composition 2 | |
| *Phase A* | |
| Cetyl alcohol | 2 |
| Glyceryl Stearate | 5 |
| Caprylic/Capric Triglyceride | 8 |
| Isopropyl Palmitate | 9 |
| *Phase B* | |
| Glycerol | 3 |
| Preservatives | 0.8 |

| Components | % |
|---|---|
| (Germaben II) | |
| Cyclo-(Arg-Gly-Asp-DPhe-Acha) | 0.0005 |
| Water, demineralised | ad 100 |

Method:

Method: Phases A and B are heated to 65-70° C. Give phase Phase B to Phase A without stirring. Homogenise and allow the mixture to cool to room temperature.

Example 15: Hair Care Formulations

Cyclopeptide or CPPC 1 is Cyclo-(Arg-Gly-Asp-DPhe-Acha);

CPPL 1 and CPPL 2 are liposomes with following composition:

CPPL 1:
CPPC 1 (0.01%)
Ethanol (17.00%)
Lecithin (5.00%)
Water (ad 100)

CPPL 2:
CPPC 1 (0.01%)
Ethanol (17.00%)
Ectoin (5.00%)
Lecithin (5.00%)
Water (ad 100)

1. Conditioning Shampoo

| Ingredients/INCI Declaration (Tradename) | Formula 1 w/w % |
|---|---|
| CPPC 1 | 0.001-0.01 |
| UREA, DISODIUM PHOSPHATE, BIOTIN, CITRIC Acid (RonaCare ® Biotin Plus) | 1.0 |
| NIACINAMIDE | 0.1 |
| HYDROXYPROPYL GUAR | 0.2 |
| SODIUM COCOAMPHOACETATE (Miranol Ultra C-32) | 10 |
| AQUA (WATER), SODIUM LAURETH SULFATE (Texapon NSO) | 32 |
| PANTHENOL | 0.5 |
| SODIUM CHLORIDE | 1.0 |
| PARFUM | q.s. |
| CITRIC ACID | q.s |
| AQUA (WATER) | ad 100 |

2. Anti-Dandruff Shampoo

| Ingredients/INCI Declaration (Tradename) | Formula 1 w/w % |
|---|---|
| CPPC 1 | 0.001-0.01 |
| MICA, CI 77891 (Timiron ® Diamond Cluster MP-149 | 0.05 |
| XANTHAN GUM | 0.7 |
| AQUA, SODIUM LAURETH SULFATE (Texapon NSO) | |
| PIROCTONE OLAMINE | 0.50 |
| COCAMIDOPROPYL BETAINE | 5.00 |
| PROPYLENE GLYCOL, 5-BROMO-5-NITRO-1,3-DIOXANE (Bronidox L) | 0.20 |
| PARFUM | 0.20 |
| AQUA (WATER) | ad 100 |

3. Hair Growth Tonic

| Ingredients/INCI Declaration (Tradename) | Formula 1 w/w % | Formula 2 w/w % | Formula 3 w/w % |
|---|---|---|---|
| CPPC 1 | 0.001-0.01 | — | — |
| CPPL 1 | — | 2.00-10.00 | — |
| CPPL 2 | — | — | 2.00-10.00 |
| CAFFEINE | 0.50 | 0.50 | 0.50 |
| ETHOXYDIGLYCOL, PROPYLENE GLYCOL, BUTYLENE GLYCOL, SODIUM BENZOATE, POTASSIUM SORBATE (Exptapon Birke Spezial) | 3.00 | 3.00 | 3.00 |
| PANTHENOL | 0.40 | 0.40 | 0.40 |
| ALCOHOL | 10.00 | 10.00 | 10.00 |
| TOCOPHERYL ACETATE | 0.30 | 0.30 | 0.30 |
| MENTHOL | 0.10 | 0.10 | 0.10 |
| PEG-40 HYDROGENATED CASTOR OIL | 1.50 | 1.50 | 1.50 |
| AQUA (WATER) | ad 100 | ad 100 | ad 100 |

3. Vitamin Hair Growth Tonic

| Ingredients/INCI Declaration (Tradename) | Formula 1 w/w % | Formula 2 w/w % | Formula 3 w/w % |
|---|---|---|---|
| CPPC 1 | 0.001-0.01 | — | — |
| CPPL 1 | — | 2.00-10.00 | — |
| CPPL 2 | — | — | 2.00-10.00 |
| NIACINAMIDE | 2.00 | 2.00 | 2.00 |
| BIOTIN | 0.02 | 0.02 | 0.02 |
| SALICYLIC ACID | 0.10 | 0.10 | 0.10 |
| ISOPROPYL ALCOHOL | 10.00 | 10.00 | 10.00 |
| PARFUM | 0.05 | 0.05 | 0.05 |
| AQUA (WATER) | ad 100 | ad 100 | ad 100 |

4. Scalp Treatment Emulsion for Hair Growth

| Ingredients/INCI Declaration (Tradename) | Formula 1 w/w % | Formula 2 w/w % | Formula 3 w/w % |
|---|---|---|---|
| CPPC 1 | 0.001-0.01 | — | — |
| CPPL 1 | — | 2.00-10.00 | — |
| CPPL 2 | — | — | 2.00-10.00 |
| ISOQUERCETIN | 0.2 | 0.2 | 0.2 |
| PROPYLENE GLYCOL | 5.00 | 5.00 | 5.00 |
| ACRYLATES/C10-30 ALKYL ACRYLATE, CROSSPOLYMER | 0.20 | 0.20 | 0.20 |
| SUCROSE STEARATE | 1.00 | 1.00 | 1.00 |
| DECYL OLEATE | 3.00 | 3.00 | 3.00 |
| DIMETHICONE | 4.00 | 4.00 | 4.00 |
| SODIUM HYDROXIDE | 0.03 | 0.03 | 0.03 |
| AQUA (WATER) | ad 100 | ad 100 | ad 100 |

5. Scalp Treatment Emulsion

| Ingredients/INCI Declaration (Tradename) | Formula 1 w/w % | Formula 2 w/w % | Formula 3 w/w % |
|---|---|---|---|
| CPPC 1 | 0.001-0.01 | — | — |
| CPPL 1 | — | 2.00-10.00 | — |
| CPPL 2 | — | — | 2.00-10.00 |
| CETEARYL ALCOHOL | 2.50 | 2.50 | 2.50 |
| CETEARETH-20 | 1.00 | 1.00 | 1.00 |
| DISODIUM RUTINYL DISULPHATE | 1.00 | 1.00 | 1.00 |
| OLEYL ERUCATE | 1.00 | 1.00 | 1.00 |
| PROPYLPARABEN | 0.05 | 0.05 | 0.05 |
| METHYLPARABEN | 0.15 | 0.15 | 0.15 |
| AQUA (WATER) | ad 100 | ad 100 | ad 100 |

6. Hair Conditioner

| Ingredients/INCI Declaration (Tradename) | Formula 1 w/w % | Formula 2 w/w % | Formula 3 w/w % |
|---|---|---|---|
| CPPC 1 | 0.001-0.01 | — | — |
| CPPL 1 | — | 2.00-10.00 | — |
| CPPL 2 | — | — | 2.00-10.00 |
| CETEARYL ALCOHOL, BEHENTRIMONIUM CHLORIDE (Incroquat Behenyl TMC) | 4.50 | 4.50 | 4.50 |
| CYCLOPENTASILOXANE, CYCLOHEXASILOXANE | 4.00 | 4.00 | 4.00 |
| PROPYLENE GLYCOL, DIAZOLIDINYL UREA, METHYLPARABEN, PROPYLPARABEN (Germaben II) | 0.70 | 0.70 | 0.70 |
| AQUA (WATER) | ad 100 | ad 100 | ad 100 |

7. Hair Spray, Aerosol

| Ingredients/INCI Declaration (Tradename) | Formula 1 w/w % |
|---|---|
| CPPC 1 | 0.001-0.01 |
| Ectoin | 1.00 |
| BENZOPHENONE -3 | 0.50 |
| PVP/VA/VINYL PROPIONATE COPOLYMER | 5.00 |
| PROPANE/BUTANE (40:60) | 30.00 |
| AQUA (WATER) | 10.00 |
| ETHANOL | ad 100 |

8. Hair Styling Gel with UV Protection

| Ingredients/INCI Declaration (Tradename) | Formula 1 w/w % | Formula 2 w/w % | Formula 3 w/w % |
|---|---|---|---|
| CPPC 1 | 0.001-0.01 | — | — |
| CPPL 1 | — | 2.00-10.00 | — |
| CPPL 2 | — | — | 2.00-10.00 |
| ACRYLATES/C10-30 ALKYL ACRYLATE, CROSSPOLYMER (Carbopol Ultrez 21) | 0.50 | 0.50 | 0.50 |
| ISOPROPYL ALCOHOL | 15.00 | 15.00 | 15.00 |
| PVP | 1.50 | 1.50 | 1.50 |
| PROPYLENE GLYCOL, DIAZOLIDINYL UREA, METHYLPARABEN, PROPYLPARABEN | 0.20 | 0.20 | 0.20 |
| AQUA, CETRIMONIUM CHLORIDE | 0.30 | 0.30 | 0.30 |
| AQUA (WATER), ETHYLHEXYL, METHOXYCINNAMATE, SILICA, PVP, CHLORPHENESIN, BHT (Eusolex UV-Pearls 2292) | 10.00 | 10.00 | 10.00 |
| AQUA (WATER) | ad 100 | ad 100 | ad 100 |

9. Cold Wave Solution

| Ingredients/INCI Declaration (Tradename) | Formula 1 w/w % |
|---|---|
| CPPC 1 | 0.001-0.01 |
| AMMONIUM THIOGLYCOLATE, AQUA | 16.00 |
| AMMONIUM BICARBONATE | 0.50 |
| PVP | 2.00 |
| POTASSIUM COCOYL HYDROLYZED COLLAGEN | 1.00 |
| NONOXYNOL-14 | 5.60 |
| TOCOPHERYL ACETATE | 1.00 |
| AQUA (WATER) | ad 100 |

Example 16: Improvement of Skin Smoothness and Reduction of Wrinkle Depth In Vivo Goal of the Study:

Determination of the effect of Cyclopeptide Cyclo-(Arg-Gly-Asp-DPhe-Acha) (=CPPC 1) on skin topography in vivo by means of Primos. The topical application of test products occurs on a defined area on the inner forearm as well as the crows' feet (eye area).

Design of the Study:

| Subjects: | Number of individuals.: | 20 (+1 reserve subject) |
| | Sex: | female |
| | Age range: | 37-63 years (average: 44.8) |
| Test Area: | Inner sides of forearms | |
| | Crows' feet | |
| Test Parameters: | 1. Determination of skin roughness by means of PRIMOS ® 5.6 (GFMeβtechnik GmbH, Teltow, Germany) | |
| | 2. Determination of wrinkle depth by means of PRIMOS ® 5.6 (GFMeβtechnik GmbH, Teltow, Germany) | |
| Design of study: | Day 0 | |
| | Determination of the parameters in the test areas | |
| | First test product application | |
| | Day 14 | |
| | Determination of the parameters 8-12 hours following the last daily test product application | |
| | Day 28 | |
| | Determination of the parameters 8-12 hours following the last daily test product application | |

Measurement of Skin Roughness:

PRIMOS (Phase-Shifting rapid in vivo measurement of skin) is a non-contact measurement device, which allows for real-time three-dimensional in vivo measurement of the micro topography of human skin based on the technology of active image triangulation. The measurement head consist of a digital micromirror device as projection unit and a CCD-camera as recording unit, mounted onto an adjustable rack. For active image triangulation an intensity encoded point M is projected onto the surface under investigation. Its image on the surface is recorded by the CCD-camera from a specific angle. The point M is a function of parameters like intensity, triangulation angle between projection system and camera and some other inner respectively outer coordinates of the camera and projection plane. The height information of the structured surface is coded in the distorted intensity pattern, which is recorded. The resolution and accuracy depends on the optical and topographical characteristics of the measured surface and on the noise characteristics of the measurement system. For accurate in vivo measurement of human skin, depending on the measured part of the human body (inner forearm, forehead, eye zone), different parameters of effective wavelength and amplification factor should be used.

To regard the differences of human skin and avoid undesired distortions by movements, the fast phase-shift technique was used for the measurement (phase width: 16 & 64 pixels). For each measurement, a minimum of 3 recordings were made and the clearest image without movement distortions or artefacts was selected for further processing.

At the end of the study, distortions due to body hairs were digitally removed and the macro structure (calculated by polynomial approximation), i.e. the curvature of the entire test area, subtracted to allow a proper analysis of the microstructure, i.e. surface roughness.

Skin roughness was then assessed by means of the parameter $R_z$ (mean depth of roughness). To mitigate potential directional effects, the evaluation was conducted using the arithmetic average of $R_Z$ from 32 radial cuts. The mean depth of roughness is defined as:

$$R_Z = \frac{1}{n}\sum_{i=1}^{n} R_{Zi}$$

where n is the number of equal segments into which the scan length I has been divided into an $R_D$ is the maximum peak to valley depth within each of the segments. In accordance with the German Standard Din 4768/1, $R_Z$ was calculated using 5 segments of equal length.

Measurement of Wrinkle Depth

The crows' feet area is recorded as 3D topography using the PRIMOS system as outlined above. To accurately detect deeper structures different settings for the fast-shift were used (phase width: 16, 64 & 128 pixels). For each measurement, a minimum of 3 recordings were made and the clearest image without movement distortions or artefacts was selected for further processing. On follow-up visits, the original captured data was projected onto the skin of the volunteers to help in the relocation process of the test area. At the end of the study, distortions due to body hairs were digitally removed and the macro structure (calculated by polynomial approximation), i.e. the curvature of the entire test area, subtracted to allow a proper analysis of the microstructure, i.e. wrinkles and surface roughness. Wrinkle depth was then assessed by means of the parameter $R_{Max}$ that is defined as the maximum vertical distance from the highest peak to the lowest valley of five segments of equal length. To mitigate locational effects, the evaluation was conducted using the arithmetic average of $R_{max}$ from 50 parallel cuts.

Performance of Test

The subjects of this study were between 37-63 years of age (average 44.8). The subjects were instructed not to use any topical preparations on the test areas starting from seven days prior to testing and until the end of the test. For cleansing, water or a mild syndet was allowed only (whole study inclusive the run-in phase).

Prior the first application of the test products, measurements were taken at clearly defined sites of the inner sides of the forearms (skin hydration, biomechanical properties, skin roughness) and in the crows' feet region (wrinkle depth). One area on the inner side of the forearms remained untreated and served as control. Further measurement was performed after 14 and 28 days of application 8-12 hours following the last daily application (adaptation time: 30 min, room temperature: 21±1° C., relative humidity: 50±5%). The subjects used the test products (approximately 2 mg/cm$^2$) twice daily (in the morning and the evening) and in a manner corresponding as largely as possible to that to be practised by the future customer.

TABLE 01

Composition of the liposome raw material (Liposome RM)

| Ingredient | Amount [%] |
| --- | --- |
| Ectoin | 5.00 |
| Ethanol, denat. | 17.2 |
| Lecithin | 5.00 |
| Water | ad 100 |

TABLE 02

Composition of the liposome raw material incl. CPPC 1 (Liposome RM containing 100 ppm/1000 ppm CPPC 1)

| Ingredient | Amount [%] |
| --- | --- |
| Ectoin | 5.00 |
| Ethanol, denat. | 17.2 |
| Lecithin | 5.00 |
| CPPC 1 | 100 ppm or 1000 ppm |
| Water | ad 100 |

TABLE 03

Composition of the test formulations

| | Raw material | INCI | % w/w | Placebo g | RM-0 g | RM-100 g | RM-1000 g |
| --- | --- | --- | --- | --- | --- | --- | --- |
| A | Montanov 202 | Arachidyl Alcohol (and) Behenyl Alcohol (and) Arachidylglucoside) | 3.00 | 30 | 30 | 30 | 30 |
| | Tegosoft DEC | Diethylhexyl Carbonate | 4.00 | 40 | 40 | 40 | 40 |
| | Cetiol A | Hexyl Laurate | 8.00 | 80 | 80 | 80 | 80 |
| B | Water | Aqua | 76.00 | 800 | 760 | 760 | 760 |
| | 1,2-Propanediol | Propylen Glycol | 3.00 | 30 | 30 | 30 | 30 |
| C | Sepigel 305 | Polyacrylamide (and) C-13-14 Isoparaffine (and) Laureth-7 | 1.00 | 10 | 10 | 10 | 10 |
| D | Liposome RM-0 (without CPPC 1) | Aqua (Water), Alcohol denat., Lecithin, Ectoin | 4.00 | — | 40 | — | — |
| | Liposome RM-100 (containing 100 ppm CPPC 1) | Aqua (Water), Alcohol denat., Lecithin, Ectoin | 4.00 | — | — | 40 | — |
| | Liposome RM-1000 (containing 1000 ppm CPPC 1) | Aqua (Water), Alcohol denat., Lecithin, Ectoin | 4.0 | — | — | — | 40 |

TABLE 03-continued

Composition of the test formulations

| Raw material | INCI | % w/w | Name of testproduct | | | |
| --- | --- | --- | --- | --- | --- | --- |
| | | | Placebo g | RM-0 g | RM-100 g | RM-1000 g |
| Germaben II | Propylene Glycol (and) Diazolidinyl Urea (and) Methylparaben (and) Propylparaben | 1.00 | 10 | 10 | 10 | 10 |
| | | 100.0000 | 1000.0000 | 1000.0000 | 1000.0000 | 1000.0000 |

Manufacture of Liposomal Compositions:
Phases A and B are separately heated to 80° C.;
Phase A is stirred into Phase B (1-2 min (200 Upm))
Phase C is added at 60° C. (500-600 Upm)
Homogenisation at 50° C./2 Min 3000 Upm (U-Turax T-50)
Phase D is then added (stirred in) at <40° C.
optionally, pH is measured and adjusted to pH 6, if necessary (10% citric acid)
Skin Roughness ($R_Z$)

Evaluated are the changes in the parameter $R_Z$ in the test product treated areas in comparison to the changes in the area treated with the placebo (A) and to the changes in the untreated control area. The absolute changes by area and time point are shown below in figure one. A decrease in $R_Z$ corresponds to an increase in skin smoothness.

FIG. 1 illustrates that the testproduct with 4% RM-0 significantly improves skin smoothness compared to the untreated control. This increase is further boosted by incorporating the Cyclopeptide Cyclo-(Arg-Gly-Asp-DPhe-Acha) (=CPPC 1) inside the liposomes (FIG. 01, testproduct 4% RM-100).

Wrinkle Depth

Evaluated is the parameter $R_{Max}$ in comparison to the initial condition in the respective test area and between the test product and placebo treated areas. The absolute changes by area and time point are shown in figure two. A decrease in $R_{Max}$ corresponds to a decrease in wrinkle depth.

FIG. 2 illustrates that the wrinkle depth has been reduced after application of the placebo as well as the basic formulation containing 4% RM-1000 (containing 0.004% of the cyclopeptide Cyclo-(Arg-Gly-Asp-DPhe-Acha) (=CPPC 1). After 4 weeks treatment the depth is further decreased by RM-1000, containing 0.004% Cyclopeptide (=CPPC 1) compared to the placebo and significantly with respect to the beginning (FIG. 02).

The reduction of the wrinkle volume has been visualized in FIG. 03.

FIG. 3 illustrates the topography of skin surface. (A.) Colorization of wrinkle depth in mm (B.) Surface before treatment, t=0 (C.) Surface after 4 weeks treatment with 4% RM-1000 (containing 0.004% CPPC 1).

Example 18: Formulations/Dosageforms

A: Vials
A solution of 100 g of a cyclopeptide of the formula I and 5 g of disodium hydrogen phosphate in 3 l of double-distilled water is adjusted to a pH of 6.5 with 2 N hydrochloric acid, subjected to sterile filtration, dispensed into injection vials and lyophilized under sterile conditions, and the vials are sealed in a sterile manner. Each injection vial contains 5 mg of active principle.

B: Suppositories
A mixture of 20 g of a cyclopeptide of the formula I is melted with 100 g of soya lecithin and 1400 g of cocoa butter, and the mixture is poured into moulds and allowed to cool. Each suppository contains 20 mg of active principle.

C: Solution
A solution is prepared from 1 g of a cyclopeptide of the formula I, 9.38 g of $NaH_2PO_4 \times 2\ H_2O$, 28.48 g of $Na_2HPO_4 \times 12\ H_2O$ and 0.1 g of benzalkonium chloride in 940 ml of double-distilled water. The pH is adjusted to 6.8, the solution is made up to 1 l and is sterilized by irradiation. This solution can be used in the form of e.g. eye drops.

D: Ointment
500 mg of a cyclopeptide of the formula I are mixed with 99.5 g of petroleum jelly under aseptic conditions.

E: Tablets
A mixture of 100 g of a cyclopeptide of the formula I, 1 kg of lactose, 600 g of microcrystalline cellulose, 600 g of maize starch, 100 g of polyvinylpyrrolidone, 80 g of talc and 10 g of magnesium stearate is pressed to give tablets in a customary manner, such that each tablet contains 10 mg of active principle.

F: Coated Tablets
Tablets are pressed as stated in Example E and are then coated in a customary manner with a coating of sucrose, maize starch, talc, tragacanth and colourant.

G: Capsules
Hard gelatine capsules are filled in a customary manner with an a cyclopeptide of the formula I such that each capsule contains 5 mg of active principle.

H: Spray
14 g of a cyclopeptide of the formula I are dissolved in 10 l of isotonic NaCl solution, and the solution is used to fill commercially available spray canisters having a pump mechanism. The solution can be sprayed into the mouth or nose. One spray burst (about 0.1 ml) corresponds to a dose of about 0.14 mg.

Figure 1:
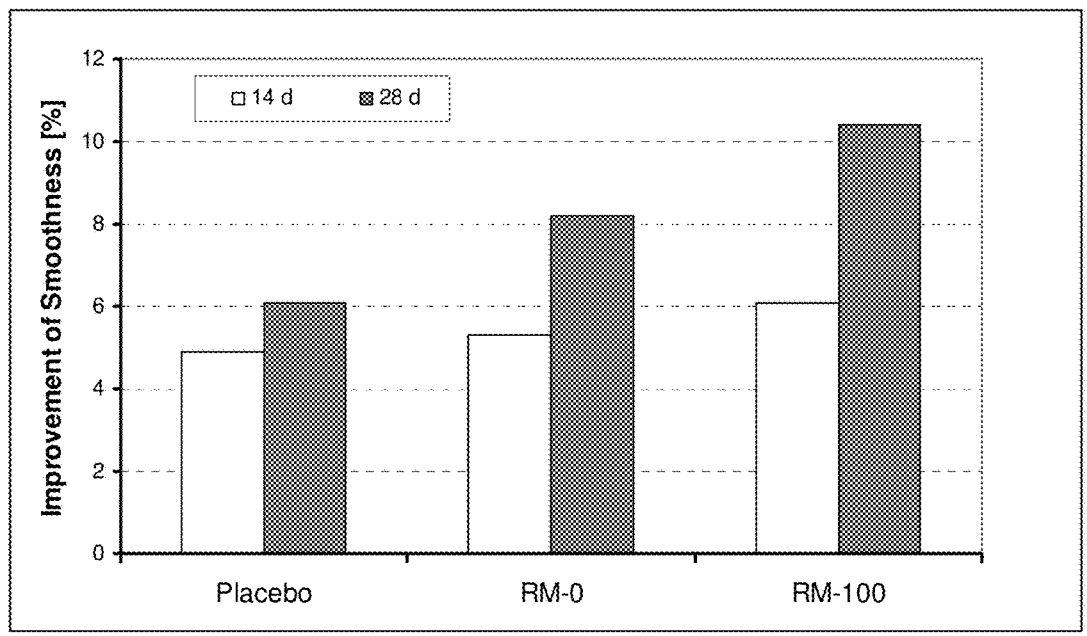
FIG. 1 illustrates that the testproduct with 4% RM-0 significantly improves skin smoothness compared to the untreated control, which increase is further boosted by incorporating the Cyclopeptide Cyclo-(Arg-Gly-Asp-DPhe-Acha) (=CPPC 1) inside the liposomes.
Figure 2:
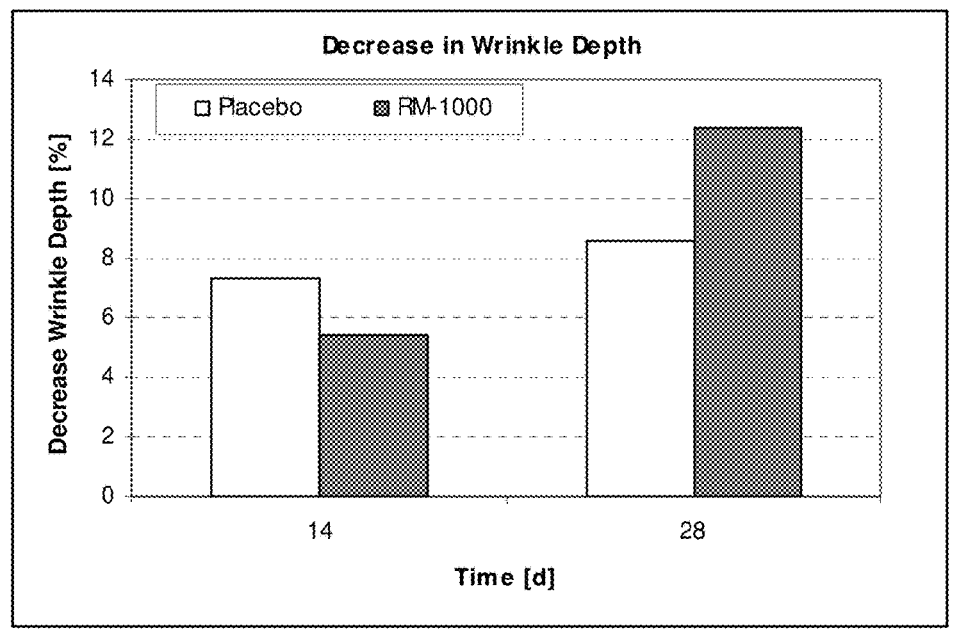
FIG. 2 illustrates that the wrinkle depth has been reduced after application of the placebo as well as the basic formulation containing 4% RM-1000 (containing 0.004% of the cyclopeptide Cyclo-(Arg-Gly-Asp-DPhe-Acha) (=CPPC 1), and after 4 weeks treatment the depth is further decreased by RM-1000, containing 0.004% Cyclopeptide (=CPPC 1) compared to the placebo and significantly with respect to the beginning.
Figure 3:
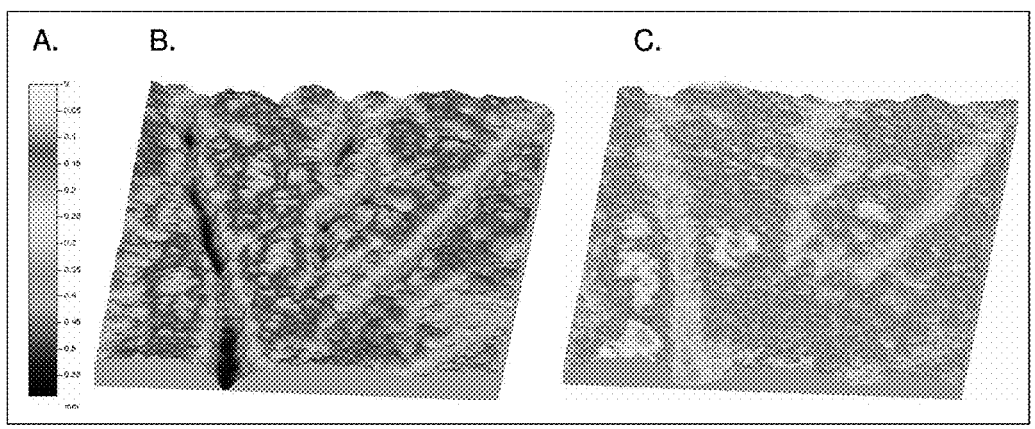
FIG. 3 illustrates the topography of skin surface, (A.) Colorization of wrinkle depth in mm (B.) Surface before treatment, t=0 (C.), and the surface after 4 weeks treatment with 4% RM-1000 (containing 0.004% CPPC 1).

The invention claimed is:

1. A method for reducing the visible signs of ageing of the skin in humans, wherein said visible signs of ageing of the skin are selected from the group consisting of stretch marks of the skin, wrinkles, skin lines, roughness of the skin, loss of skin elasticity, loss of skin firmness, loss of skin tightness, and slack tissue, comprising administering to a portion of the skin of said human showing said visible signs of ageing a composition for topical use and/or a cosmetic composition, said composition being a liposome composition comprising
    i) 0.001 to 1% by weight of cyclo-(Arg-Gly-Asp-DPhe-Acha) and/or a salt thereof, wherein at least 10% of the Cyclo-(Arg-Gly-Asp-DPhe-Acha) and/or the salt thereof is entrapped in liposomes,
    ii) 0.01 to 20% by weight of one or more lipids,
    iii) 60 to 99.99% by weight of one or more physiologically acceptable solvents, and optionally
    iv) 0.0001 to 20% by weight of one or more further ingredients, selected from the group consisting of
        α) further active compounds having a skin-care, hair-care and/or inflammation-inhibiting action, and
        β) further cosmetically acceptable excipients.

2. The method according to claim 1, wherein in the liposome composition, the lipids comprise one or more of the following:
    a) phospholipids,
    b) glycosphingolipids,
    c) lecithin,
    d) spingomyelin,
    e) dipalmitoyl lecithin,
    f) distearoylphosphatidylcholine,
    g) phosphatidylcholine,
    h) saturated phosphatidylcholine,
    i) unsaturated phosphatidylcholine,
    j) polystyrene,
    k) octyldodecanol, optionally in combination with Silica,
    l) octyldodecanol, optionally in combination with phospholipids, cholesterol and/or glycospingolipids,
and/or one or more salts thereof.

3. The method according to claim 1, wherein in the liposome composition, the one or more physiologically acceptable solvents comprise:
    water, and/or
    an alcohol having 2 to 5 carbon atoms, which is ethanol, isopropanol, glycerin, 1,2-propylene glycol, 1,4-butanediol, pentylene glycol, sorbitol or a mixture thereof.

4. The method according to claim 1, wherein the liposome composition comprises
    i) 0.001 to 1% by weight of cyclo-(Arg-Gly-Asp-DPhe-Acha), and/or a salt thereof,
    ii) 0.01 to 20% by weight of one or more lipids,
    iii) 70 to 99% by weight of one or more physiologically acceptable solvents, and optionally
    iv) 0.001 to 10% by weight of one or more further ingredients, selected from the group consisting of
        α) further active compounds having a skin-care, hair-care and/or inflammation-inhibiting action, and
        β) further cosmetically acceptable excipients.

5. The method according to claim 1, wherein in the liposome composition, the further active compounds having a skin-care, hair-care and/or inflammation-inhibiting action comprises ectoin in an amount of 0.1 to 1% by weight.

6. The method according to claim 1, wherein in the liposome composition, the further active compounds having a skin-care, hair-care and/or inflammation-inhibiting action comprises ectoin in an amount of 1% by weight.

7. The method according to claim 1, wherein in the liposome composition, the further active compounds having a skin-care, hair-care and/or inflammation-inhibiting action comprises ectoin in an amount of up to 3% by weight.

8. The method according to claim 1, wherein in the liposome composition, at least 20% of the Cyclo-(Arg-Gly-Asp-DPhe-Acha) and/or the salts thereof is entrapped in liposomes.

9. The method according to claim 1, wherein in the liposome composition, at least 50% of the Cyclo-(Arg-Gly-Asp-DPhe-Acha) and/or the salts thereof is entrapped in liposomes.

10. The method according to claim 1, wherein in the liposome composition, at least 75% of the Cyclo-(Arg-Gly-Asp-DPhe-Acha) and/or the salts thereof is entrapped in liposomes.

11. The method according to claim 1, wherein in the liposome composition, at least 95% of the Cyclo-(Arg-Gly-Asp-DPhe-Acha) and/or the salts thereof is entrapped in liposomes.

12. The method according to claim 1, wherein in the liposome composition, the one or more lipids are selected from the group consisting of lecithin, spingomyelin, dipalmitoyl lecithin, distearoylphosphatidylcholine, phosphatidylcholine, saturated phosphatidylcholine and unsaturated phosphatidylcholine, or is a mixture thereof or is a salt thereof.

13. The method according to claim 1, wherein the liposome composition comprises 0.05 to 0.5% by weight of cyclo-(Arg-Gly-Asp-DPhe-Acha), and/or a salt thereof.

14. The method according to claim 1, wherein the liposome composition comprises 2 to 10% by weight of one or more lipids.

15. The method according to claim 1, wherein the liposome composition comprises 0.0001 to 20% by weight of one or more further ingredients, which are selected from the group consisting of
    α) further active compounds having a skin-care, hair-care and/or inflammation-inhibiting action, and
    β) further cosmetically acceptable excipients.

16. The method according to claim 1, wherein said visible signs of ageing of the skin is stretch marks of the skin.

17. The method according to claim 1, wherein said visible signs of ageing of the skin is wrinkles.

18. The method according to claim 1, wherein said visible signs of ageing of the skin is skin lines.

19. The method according to claim 1, wherein said visible signs of ageing of the skin is roughness of the skin.

20. The method according to claim 1, wherein said visible signs of ageing of the skin is loss of skin elasticity.

21. The method according to claim 1, wherein said visible signs of ageing of the skin is loss of skin firmness.

22. The method according to claim 1, wherein said visible signs of ageing of the skin is loss of skin tightness.

23. The method according to claim 1, wherein said visible signs of ageing of the skin is slack tissue.

* * * * *